US012806280B2

(12) United States Patent
Lundgren Åkerlund et al.

(10) Patent No.: US 12,806,280 B2
(45) **Date of Patent: *Nov. 24, 2026**

(54) DETECTION AND TREATMENT OF MALIGNANT TUMOURS IN THE CNS

(71) Applicant: Targinta AB, Lund (SE)

(72) Inventors: Evy Lundgren Åkerlund, Bjärred (SE); Ramiro Gisler, Lund (SE); Jan Talts, Staffanstorp (SE)

(73) Assignee: Targinta AB, Lund (SE)

( * ) Notice: Subject to any disclaimer, the term of this patent is extended or adjusted under 35 U.S.C. 154(b) by 1295 days.

This patent is subject to a terminal disclaimer.

(21) Appl. No.: 17/220,012

(22) Filed: Apr. 1, 2021

(65) Prior Publication Data

US 2021/0316005 A1 Oct. 14, 2021

Related U.S. Application Data

(62) Division of application No. 15/550,837, filed as application No. PCT/SE2016/050116 on Feb. 16, 2016, now Pat. No. 10,994,022.

(30) Foreign Application Priority Data

Feb. 16, 2015 (SE) .................................. 1550168-7

(51) Int. Cl.

| | |
|---|---|
| ***A61K 39/395*** | (2006.01) |
| ***A61K 47/68*** | (2017.01) |
| ***A61K 51/10*** | (2006.01) |
| ***A61P 35/00*** | (2006.01) |
| ***C07K 16/28*** | (2006.01) |
| ***C12Q 1/6886*** | (2018.01) |
| ***G01N 33/575*** | (2026.01) |

(52) U.S. Cl.

CPC ...... *A61K 47/6849* (2017.08); *A61K 47/6825* (2017.08); *A61K 51/1045* (2013.01); *A61P 35/00* (2018.01); *C07K 16/2845* (2013.01); *C12Q 1/6886* (2013.01); *G01N 33/57557* (2026.01); *C07K 2317/73* (2013.01); *C07K 2317/76* (2013.01); *C12Q 2600/156* (2013.01); *C12Q 2600/158* (2013.01); *G01N 2333/70546* (2013.01)

(58) Field of Classification Search

None

See application file for complete search history.

(56) References Cited

U.S. PATENT DOCUMENTS

| | | | |
|---|---|---|---|
| 2006/0127398 | A1 | 6/2006 | Lundgren-Akerlund et al. |
| 2007/0048325 | A1 | 3/2007 | Van Epps et al. |
| 2008/0008707 | A1 | 1/2008 | Freimark et al. |

FOREIGN PATENT DOCUMENTS

| | | | |
|---|---|---|---|
| WO | 9951639 | A1 | 10/1999 |
| WO | 03101497 | A1 | 12/2003 |
| WO | 03106492 | A1 | 12/2003 |
| WO | 2004016758 | A1 | 2/2004 |
| WO | 2004089990 | A1 | 10/2004 |
| WO | 2005026334 | A2 | 3/2005 |
| WO | 2007107774 | A2 | 9/2007 |
| WO | 2007107774 | A3 | 4/2008 |
| WO | 2011026026 | A1 | 3/2011 |
| WO | 2011141153 | | 4/2012 |

OTHER PUBLICATIONS

Agarwal et al., "Site-Specific Antibody—Drug Conjugates: The Nexus of Bioorthogonal Chemistry, Protein Engineering, and Drug Development," Bioconjugate Chem. 2015, 26, pp. 176-192.

Almagro et al., "Humanization of antibodies", Frontiers in Bioscience 2008, 13, pp. 1619-1633 (2008).

Ansell et al., "Cellular Composition of the Tumor Microenvironment," Am Soc Clin Oncol Educ Book pp. e91-e97 (2013).

Bengtsson et al., "Loss of a10B1 integrin expression leads to moderate dysfunction of growth plate chondrocytes," Journal of Cell Science 118, pp. 929-936 (2005).

Bidard et al., "Trends in cancer-targeted antibody-drug conjugates," Targ Oncol (2014) 9:1-8.

Bingle et al., "The role of tumour-associated macrophages in tumour progression: implications for new anticancer therapies," J Pathol 2002; 196: 254-265.

Brown et al., "Regulatory effect of nerve growth factor in α9β1 integrin-dependent progression of glioblastoma," Neuro-Oncology, pp. 968-980, Dec. 2008.

Camper et al., "Distribution of the collagen-binding integrin α10β1 during mouse development," Cell Tissue Res (2001) 306:107-116.

Camper et al., "Isolation, Cloning, and Sequence Analysis of the Integrin Subunit α10, a β1-associated Collagen Binding Integrin Expressed on Chondrocytes," vol. 273, No. 32, pp. 20383-20389, Aug. 7, 1998.

Communication pursuant to Article 94(3) EPC, received in European Patent Application No. EP 16725735.7, dated Feb. 13, 2020 (4 pages).

Corrected International Search Report and Written Opinion received in corresponding International Application No. PCT/SE2016/050116, issued Aug. 26, 2016 (18 pages).

David et al., "The 2007 WHO Classification of Tumours of the Central Nervous System", 114(2), pp. 97-109 (Jul. 6, 2007).

Degenst et al., "Antibody repertoire development in camelids", Dev Comp Immunol 2006, 30, pp. 187-198 (2006).

Dunn et al, "Emerging insights into the molecular and cellular basis of glioblastoma," Genes & Development 26:756-784 (2012).

(Continued)

*Primary Examiner* — Meera Natarajan
(74) *Attorney, Agent, or Firm* — Weston R. Gould; DINSMORE & SHOHL LLP

(57) ABSTRACT

The present invention concerns methods of diagnosing and treating a malignant neoplasm of the CNS by detecting mammalian tissue expressing integrin alpha 10 subunit or a fragment or variant thereof, and administering a drug specific for integrin alpha 10 subunit.

13 Claims, 13 Drawing Sheets

Specification includes a Sequence Listing.

(56) References Cited

OTHER PUBLICATIONS

Engel et al., “Expression of integrin alpha 10 is transcriptionally activated by pRb in mouse osteoblasts and is downregulated in multiple solid tumors,” Cell Death and Disease (2013) 4, e938.
Gan et al., “The epidermal growth factor receptor variant III (EGFRvIII): where wild things are altered,” FEBS Journal 280 (2013) 5350-5370.
Hanahan et al. “Hallmarks of Cancer: The Next Generation,” Cell 144, Mar. 4, 2011, pp. 646-674.
Kleihues et al., “The WHO Classification of Tumors of the Nervous System,” Journal of Neuropathology and Experimental Neurology, vol. 61, No. 3, pp. 215-225, Mar. 2002.
Leboit, P.E. et al., “Pathology and Genetics of Skin Tumours,” World Health Organization Classification of Tumours, International Agency for Research on Cancer, 2006 (8 pages).
Lorger et al., “Tumor Microenvironment in the Brain,” Cancers 2012, 4, 218-243.
Louis et al., “The 2016 World Health Organization Classification of Tumors of the Central Nervous System: a summary,” Acta Neuropathol (2016) 131:803-820.
Lundgren-Akerlund et al., “Integrin α10β1: A Collagen Receptor Critical in Skeletal Development,” Advances in Experimental Medicine and Biology, 819, pp. 61-71 (2014).
Response to Communication Pursuant to Rules 70(2) and 70a(2) EPC dated Mar. 5, 2019, filed on Sep. 16, 2019, in European Patent Application No. 16752735.7 (7 pages).
Schmieder et al., “Differentiation and gene expression profile of tumor-associated macrophages,” Seminars in Cancer Biology 22 (2012) 289-297.
Supplementary Figures with figure legends as provided to European Patent Office in corresponding European Patent Application No. 16752735.7 (3 pages) (2020).
Thoren et al., “Integrin alpha10, a Novel Therapeutic Target in Glioblastoma, Regulates Cell Migration, Proliferation, and Survival”, Cancers, 11, 587, 24 pages (2019).
Varas et al., α10 Integrin Expression Is Up-Regulated on Fibroblast Growth Factor-2-Treated Mesenchymal Stem Cells with Improved Chondrogenic Differentiation Potential, Stem Cells and Development 16:965-978 (2007).
Verhaak et al., “An integrated genomic analysis identifies clinically relevant subtypes of glioblastoma characterized by abnormalities in PDGFRA, IDH1, EGFR and NF1,” Cancer Cell, Jan. 19, 2010 (25 pages).
Wenke et al., “Expression of integrin alpha10 is induced in malignant melanoma,” Cellular Oncology 29 (2007) 373-386.
Yoshinaga et al., “Ig L-chain Shuffling for Affinity Maturation of Phage Library-derived Human Anti-human MCP-1 Antibody Blocking its Chemotactic Activity”, J. Biochem 2008, 143, pp. 593-601 (2008).
Young et al., “Antibody-Cytokine Fusion Proteins for Treatment of Cancer: Engineering Cytokines for Improved Efficacy and Safety”, Semin Oncol. 41(5): 623-636 (2014).
Zhou et al., p. 691, “Melanoma”, Modern Neurosurgery, Fudan University Press (Jan. 31, 2015) (with English translation attached).
Official Action in Chinese Application No. 201680014302.1, mailed Feb. 7, 2021 (with English Translation attached) (21 pages).
Protein Atlas “ITGA10—Integrin subunit alpha 10”, (Sep. 13, 2019), retrieved from https://www.proteinatlas.org/ENSG00000143127-ITGA10/tissue (2 pages).
Vogel & Marcotte, “Insights into the regulation of protein abundance from proteomic and transcriptomic analyses”, Nat Rev Genet., 13(4), pp. 227-232 (2012).
Notification of Reexamination from CN 2016800143021 issued by CNIPA on May 25, 2025, English translation only, 15 pages.

A

B

A

B

C
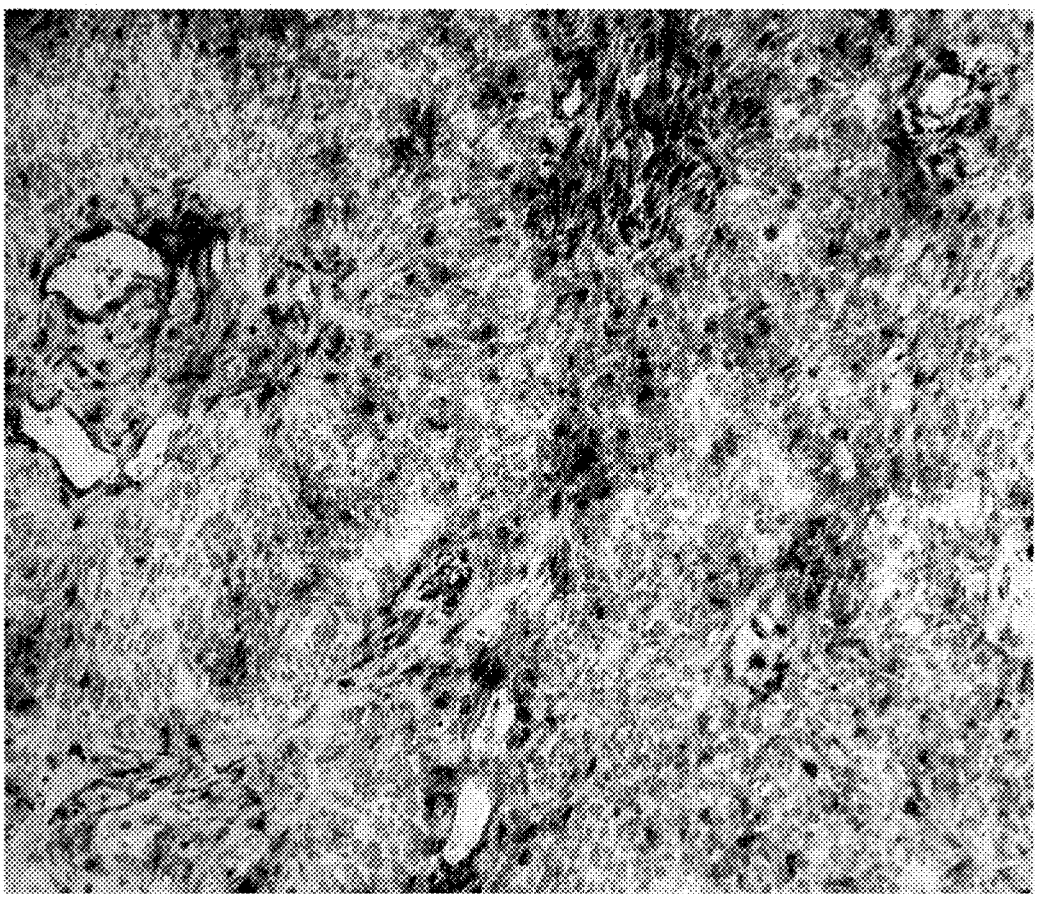
D
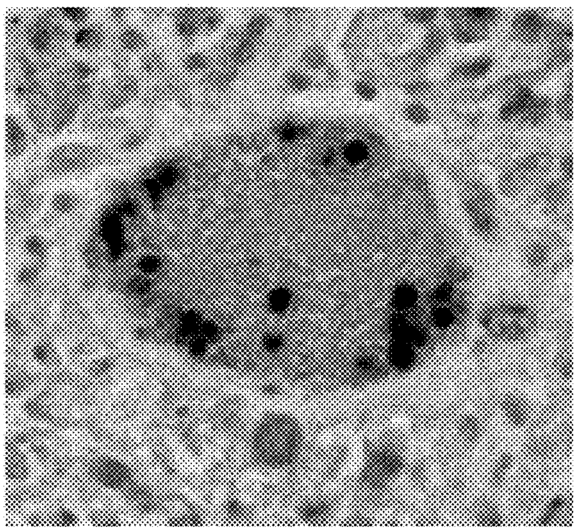
Fig. 5, cont.

A

B

A B C

C E F

DETECTION AND TREATMENT OF MALIGNANT TUMOURS IN THE CNS

CROSS REFERENCE TO RELATED APPLICATIONS

This application is a divisional of U.S. application Ser. No. 15/550,837, filed on Aug. 14, 2017, which is a non-provisional application filed under 35 U.S.C. § 371 based on International Application No. PCT/SE2016/050116, filed on Feb. 16, 2016, which claims priority to Swedish Application No. SE 1550168-7, filed on Feb. 16, 2015, all of which are incorporated by reference in their entirety.

FIELD OF INVENTION

The present invention relates to methods for detecting and treatment of malignant tumours in the central nervous system based on integrin alpha 10 subunit expression.

BACKGROUND OF INVENTION

Primary brain tumours originate within brain tissue. There are several types of primary brain tumours. The most common type of diagnosed malignant primary brain tumours belong to the group of gliomas. Gliomas can develop from several types of glial cells, for example astrocytes, oligodendrocytes, and ependymal cells. The gliomas are graded from low-grade (I) to high-grade (IV) reflecting the growth potential and aggressiveness of the tumour.

Glioblastoma (also known as Glioblastoma multiforme, GBM) belongs to the group of gliomas and is graded as a high-grade glioma. It is the most common and the most aggressive type of primary brain tumour. As described by the World Health Organization classification, glioblastoma tumours are characterized by the presence of small areas of necrotizing tissue that is surrounded by anaplastic cells. This characteristic, as well as the presence of hyperplastic blood vessels, differentiates the tumour from Grade III astrocytomas, which do not have these features. Emerging classification schemes not solely based on morphology are likely to incorporate molecular differences that further distinguish these tumours. Glioblastomas can therefore additionally be characterized in four distinct subtypes depending on their molecular expression patterns (Verhaak et al, 2010; Dunn et al, 2012). Classical, mesenchymal, proneural, and neural subtypes are defined by their aberrations and gene expression of epidermal growth factor receptor (EGFR), neurofibromatosis (NF1), platelet derived growth factor receptor A (PDGFRA) and isocitrate dehydrogenase (IDH1).

Glioblastoma is a highly heterogeneous tumour containing different types of cells and there is a great variation in cell content between patients. Cell types occurring are for example astrocytes, oligodendrocytes and fibroblasts. The tumour cells spread and infiltrate the adjacent tissue very quickly and they exhibit a high resistance to both radiation and chemotherapy. About 28 000 new cases of this disease are diagnosed each year in the U.S. and the EU (source: U.S. National Cancer Registry). Glioblastoma is the most lethal brain tumour. Without treatment the medium survival time is 4 months and with available treatment about 15 months. Many patients do not survive longer than 6 months from diagnosis and most die within 2 years. Only a few survive for as long as 5 years.

As of today, no specific pre-surgical laboratory studies are helpful in diagnosing GBM. Imaging studies of the brain are essential for making the diagnosis, including computed tomography, magnetic resonance imaging, with and without contrast, positron emission tomography, and magnetic resonance spectroscopy. To make sure of the diagnosis, a pathological exam of brain tissue has to be made. Tumour genetics are useful for predicting response to adjuvant therapy. However, today there is no difference in treatment regimens between the different types of glioblastomas.

Glioblastomas are the most common and the most aggressive malignant neoplasm of the CNS. The incidence is 2-3 cases/100 000 individuals. Treatment today involves surgery, chemotherapy and radiation. Standard treatment consists of maximal surgical resection to lessen pressure on the brain, radiotherapy, and concomitant and adjuvant chemotherapy with temozolomide. Without treatment the mean survival time is 4.5 months and with current treatments available this can be extended to 15 month. Because of the severity of the disease, it has been attempted to find new drugs to treat glioblastomas and other malignant neoplasms of the brain. However, neither these nor traditional therapies have resulted in any significant improvement for glioblastoma patients or increase in the survival rate.

There is thus an urgent need to find more effective methods for detection, diagnosis and treatment of malignant neoplasms of the CNS, including gliomas.

SUMMARY OF INVENTION

The present inventors have found that the protein integrin alpha 10 beta 1 is expressed in tissue obtained from malignant neoplasms of the CNS. Based on this finding the inventors have developed methods and tools for detecting an integrin alpha 10 subunit with the aim of diagnosing and treating malignant neoplasms of the CNS.

It is thus an object of the present invention to provide a method for determining the presence of malignant neoplasms in the CNS of a patient and to treat these.

In one aspect the present invention concerns a composition for use in the treatment of a malignant neoplasm in the central nervous system, said composition comprising an antibody specifically binding to an integrin alpha 10 subunit.

In another aspect the invention concerns a method of treatment of a malignant neoplasm in the central nervous system of a subject in need thereof, said method comprising administering to said subject an antibody specifically binding to an integrin alpha 10 subunit.

In yet another aspect the invention concerns a method of treating a subject suffering from a malignant neoplasm in the central nervous system, said method comprising:

a) determining if a subject is suffering from a malignant neoplasm of the central nervous system according to the methods described herein; and
b) administering to a subject diagnosed with a malignant neoplasm of the central nervous system, a therapeutically effective amount of an antibody specifically binding to an integrin alpha 10 subunit to said subject as defined in any one of the preceding embodiments.

In another aspect the invention concerns the use of a composition comprising an antibody specifically binding to an integrin alpha 10 subunit for the manufacture of a medicament for the treatment of a malignant neoplasm in the central nervous system.

In another aspect the invention concerns a method of inhibiting tumour associated vascularization in a mammal, the method comprising administering to said mammal a therapeutically effective amount of an anti-integrin alpha 10 subunit antibody according to any one of the preceding claims.

In another aspect the invention concerns an antibody-drug conjugate comprising an integrin-alpha 10 specific antibody covalently linked to a radioactive tracer or a cytotoxic moiety.

In another aspect the invention concerns a nanoparticle comprising an integrin alpha-10 specific antibody and a radioactive tracer.

In another aspect the invention concerns a kit for detecting a malignant neoplasm of the central nervous system, such as a glioma, in vitro, in situ or in vivo, the kit comprising an antibody specific for an integrin alpha 10 subunit, a peptide capable of binding specifically to an integrin alpha 10 subunit antigen, or a polynucleotide probe capable of hybridizing specifically to an integrin alpha 10 subunit transcript or its complement, and optionally, instructions for use.

It is a further object of the present invention to provide products, which can be used in the detection, diagnosis and successful and targeted treatment of malignant neoplasms of the CNS such as gliomas.

In a first aspect the present invention concerns a method for detecting a malignant neoplasm in the central nervous system of a mammal, said method comprising analysing in an isolated sample, the presence or absence of:

i) an antigen comprising an integrin alpha 10 subunit polypeptide, or ii) a polynucleotide transcript which encodes an integrin alpha 10 subunit polypeptide or a fragment or variant thereof, wherein presence of the antigen of a) or the polynucleotide transcript of b) is indicative of a malignant neoplasm in the central nervous system of said mammal.

In another aspect the present invention concerns a method for detecting a malignant neoplasm in the central nervous system of a mammal, said method comprising the steps of:

a) administering to a subject a molecular probe capable of binding specifically to an integrin alpha 10 subunit polypeptide, or to an integrin alpha 10 subunit polynucleotide transcript, said probe being covalently bound to a moiety capable of emitting photons, b) detecting photons emitted from said moiety and forming an image of the central nervous system or part thereof, wherein localised emission of photons from said moiety is indicative of a malignant neoplasm in the central nervous system of said mammal.

In another aspect the invention concerns an in vitro diagnostic method to diagnose a malignant neoplasm in the central nervous system of a mammal, said method comprising the steps of:

a) contacting an in vitro sample with a molecular probe capable of binding specifically to an integrin alpha 10 subunit polypeptide, or to an integrin alpha 10 subunit polynucleotide transcript, said probe being covalently bound to a moiety capable of emitting photons, b) detecting photons emitted from said moiety and forming an image of the sample, wherein localised emission of photons from said moiety is indicative of a malignant neoplasm in the central nervous system of said mammal.

In another aspect the present invention concerns an in vitro method for the detection of an integrin alpha 10 subunit in an isolated sample, said method comprising analysing in said isolated sample, the presence or absence of:

a) an antigen comprising an integrin alpha 10 subunit polypeptide, or b) a polynucleotide transcript which encodes an integrin alpha 10 subunit polypeptide or a fragment or variant thereof, wherein presence of the antigen of a), or the polynucleotide transcript of b) is indicative of a malignant neoplasm in said isolated sample.

In another aspect the present invention concerns use of an anti-integrin alpha 10 subunit-specific antibody which binds specifically to integrin alpha 10 subunit to detect a malignant neoplasm of the central nervous system in a biological sample in vitro, in situ or in vivo.

In another aspect the present invention concerns use of an integrin alpha 10 subunit nucleic acid probe which binds to an integrin alpha 10 subunit mRNA or cDNA in a hybridizing reaction to detect a malignant neoplasm of the central nervous system in a biological sample in vitro, in situ or in vivo.

In another aspect the present invention concerns use of an integrin alpha 10 subunit nucleic acid probe compound in the preparation of a kit for diagnosing a malignant neoplasm of the central nervous system.

In another aspect the present invention concerns use of an anti-integrin alpha 10 subunit-specific antibody which binds to an integrin alpha 10 subunit, in the preparation of a kit for diagnosing a malignant neoplasm of the central nervous system.

In another aspect the present invention concerns use of an integrin alpha 10 subunit nucleic acid probe compound, for the manufacture of a diagnostic agent for diagnosing, monitoring or determining if a subject has a malignant neoplasm of the central nervous system, wherein said diagnostic agent is manufactured to measure presence of an integrin alpha 10 subunit polynucleotide in a biological sample, wherein presence of said integrin alpha 10 subunit polynucleotide in said sample is indicative of a malignant neoplasm of the central nervous system of said subject.

In another aspect the present invention concerns use of an anti-integrin alpha 10 subunit-specific antibody which binds to an integrin alpha 10 subunit, for the manufacture of a diagnostic agent for diagnosing, monitoring or determining if a mammal has a malignant neoplasm of the central nervous system, wherein said diagnostic agent is manufactured to measure presence of an integrin alpha 10 subunit polypeptide in a sample, wherein presence of said integrin alpha 10 subunit polypeptide in said sample is indicative of a malignant neoplasm of the central nervous system of said mammal.

DESCRIPTION OF DRAWINGS

FIG. 4A shows a part of the patient sample with a typical brain morphology while FIG. 4B shows another part of the same sample with malignant brain tissue (glioblastoma multiforme). Using a polyclonal antibody directed against an integrin alpha 10 subunit (Camper et al (1998) J Biol Chem. 273(32):20383-9) it was shown that the integrin alpha 10 subunit is specifically and strongly expressed on glioblastoma cells, whereas negligible expression of the integrin alpha 10 subunit was seen in morphologically unaffected brain tissue.

FIG. 8A shows confocal microscopy imaging of brain tumour glioblastoma tissue labeled for DNA with DAPI. FIG. 8B shows microscopy imaging of tissue visualized by phase contrast microscopy. FIG. 8C shows confocal microscopy imaging of CD 163 expression in the tumour tissue using anti-CD 163 antibody. FIG. 8D shows confocal microscopy imaging of integrin alpha 10 subunit expression in the tumour tissue using an anti-integrin alpha 10 subunit antibody. FIG. 8E shows confocal microscopy imaging of CD 206 expression in the tumour tissue using an anti-CD 206 antibody in tissue. FIG. 8F shows a composite of FIGS. 8A-E and demonstrates co-localisation of CD163, integrin alpha 10 subunit and CD206.

FIG. 9A shows confocal microscopy imaging of brain tumour glioblastoma tissue labeled for DNA with DAPI. FIG. 9B shows microscopy imaging of tissue visualized by phase contrast microscopy. FIG. 9C shows confocal microscopy imaging of EGFRvIII expression in the tumour tissue using an anti-EGFRvIII antibody. FIG. 9D shows confocal microscopy imaging of integrin alpha 10 subunit expression in the tumour tissue using an anti-integrin alpha 10 subunit antibody. FIG. 9E shows a composite of FIGS. 9A-D and demonstrates co-localisation of EGFRvIII and integrin alpha 10 subunit.

DEFINITIONS

Figure 1:
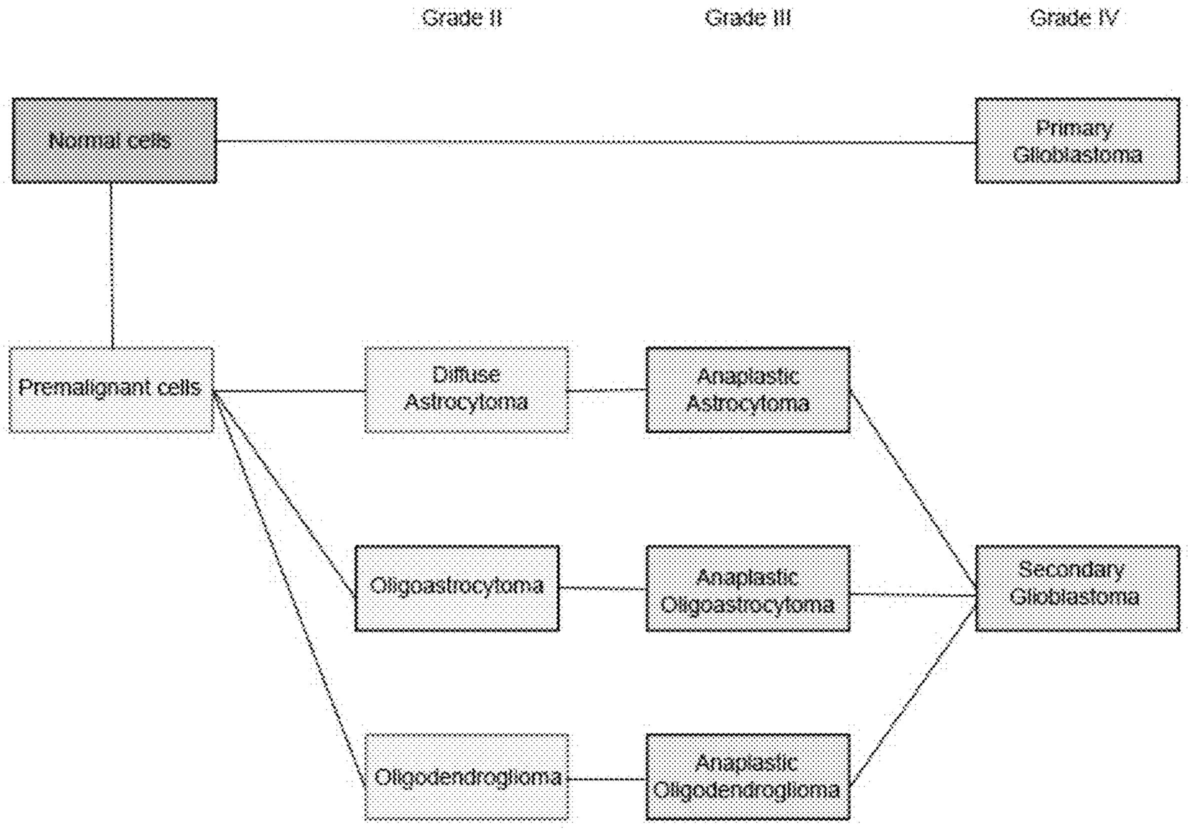
FIG. 1: Overview of malignant neoplasms of the brain, and their progression. Malignant neoplasms are phenotypically classified according to their apparent morphology and graded according to their severity based on histologic features of the tumour. Shown in this figure are major classifications of glioma and putative tumour progression pathways from normal cells to glioblastoma.

"Anti-integrin alpha 10 antibody" or "Anti-integrin alpha 10 subunit antibody" as used herein refers to an antibody capable of recognising and binding to at least the alpha 10 subunit of the heterodimeric protein integrin alpha 10 beta 1. These antibodies may be antibodies that recognizes an epitope of the heterodimeric protein integrin alpha 10 beta 1, wherein the epitope comprises amino acid residues of both the alpha 10 and the beta 1 subunit.

"Integrin alpha 10" or "Integrin alpha 10 subunit" as used herein refers to the alpha 10 subunit of the heterodimeric protein integrin alpha 10 beta 1. This denotation does not exclude the presence of the beta 1 subunit bound to the alpha 10 subunit thus forming the quaternary structure of integrin alpha 10 beta 1 heterodimer.

"Bispecific antibody" as used herein refers to an antibody with two different variable domain binding sites (Fv), each binding to a different antigen.

"Subject" as used herein denotes a mammal, such as a rodent, a feline, a canine, and a primate. Preferably a subject according to the invention is a human.

As used herein, the singular forms "a", "an" and "the" include plural referents unless the context clearly states otherwise. Thus, for example, reference to "an antibody" includes a plurality of such antibodies.

A "biological sample" as used herein encompasses any subject and a variety of sample types obtained from any subject. Examples of biological samples useful in the disclosed methods include but are not limited to a subject, a liquid tissue sample such as blood, or a solid tissue sample such as biopsy material or tissue cultures or cells derived there from and the progeny thereof. For example, biological samples include cells obtained from a tissue sample collected from a subject. Thus biological samples encompass clinical samples, cells in culture, cell supernatants, cell lysates, and tissue samples, e.g. tissue samples from a brain such as an adult brain, tissue samples from CNS including tumour samples from the brain etc.

"Detection", "detect", "detecting" as used herein includes qualitative and/or quantitative detection (measuring levels) with or without reference to a control, and further refers to the identification of the presence, absence or quantity of a given target, specifically the target of an integrin alpha 10 subunit.

"Analyzing" as used herein includes qualitative and/or quantitative detection (measuring levels) with or without reference to a control, and further refers to the identification of the presence, absence or quantity of a given target, specifically the target of an integrin alpha 10 subunit.

A "radioactive tracer", or "radioactive label", is a chemical compound in which one or more atoms have been replaced by a radioisotope so by virtue of its radioactive decay it can be used to explore the mechanism of chemical reactions by tracing the path that the radioisotope follows from reactants to products.

Radioisotopes of hydrogen, carbon, phosphorus, sulphur, and iodine have been used extensively to trace the path of biochemical reactions. A radioactive tracer can also be used to track the distribution of a substance within a natural system such as a cell or tissue. Radioactive tracers form the basis of a variety of imaging systems, such as, PET scans, SPECT scans and technetium scans. The term "radioactive tracer" includes radioactive isotopes that emit therapeutic dosages of radiation such as $^{131}$Iodine.

DETAILED DESCRIPTION

The present inventors have surprisingly found that the integrin alpha 10 subunit (Uniprot: 075578) encoded by the gene ITGA10 is expressed in tissue obtained from biopsies of CNS tissue in particular from malignant neoplasms of the brain. Based on this finding the inventors have developed methods and tools for detecting an integrin alpha 10 subunit and demonstrated that it is possible to diagnose and/or treat malignant neoplasms of the CNS, and subtypes such as glioma.

I. Treatment of Malignant Neoplasms of the Central Nervous System

In one aspect, the present invention concerns treatment of one or more malignant neoplasms of the CNS. In a preferred embodiment the treatment is conducted using a specific anti-integrin alpha 10 subunit antibody as described herein. The antibody is preferably prepared to be comprised in a pharmaceutical composition as outlined below.

Pharmaceutical Compositions and Administration Thereof

In one embodiment the present invention relates to pharmaceutical compositions comprising the antibodies and functional equivalents thereof according to the invention. The invention furthermore relates to medicaments for treatment of a clinical condition comprising the antibody, methods of treatment of malignant neoplasms of the CNS comprising administration of said antibody or use of said antibody for preparation of a medicament for treatment of a clinical condition.

The clinical condition may be any of the conditions mentioned herein. The individual in need of administration of anti-integrin alpha 10 subunit antibodies may be any individual suffering from said condition or at risk of acquiring said clinical condition. Preferably, the individual is a human being.

Treatment may be curative, palliative, ameliorating and/or prophylactic treatment. The pharmaceutical compositions of the present invention preferably comprise a pharmaceutical effective amount of at least one antibody or functional equivalent thereof specifically recognising an epitope within the extracellular domain of an integrin alpha 10 subunit (herein above and below designated "anti-integrin alpha 10 antibody" or "anti-integrin alpha 10 subunit antibody"). For in vitro purposes, e.g. for detecting integrin alpha 10 beta 1 in blood or tissue samples antibodies capable of recognising the cytoplasmic domain of integrin alpha 10 beta 1 may also be used.

A pharmaceutically effective amount as referred to herein is typically an amount of anti-integrin alpha 10 subunit antibody, which induces the desired response in an individual receiving said pharmaceutical composition.

The pharmaceutically effective amount of the anti-integrin alpha 10 subunit antibody depends on the individual to which it should be administered, in particular on the size of said individual as well as the clinical condition and the specific mode of administration. In general however, in the range of 1 mg to 5000 mg, preferably in the range of 10 mg to 3000 mg, more preferably in the range of 50 mg to 1000 mg, for example in the range of 100 mg to 750 mg, such as in the range of 150 mg to 500 mg, for example in the range of 200 mg to 400 mg, such as in the range of 250 mg to 350 mg, for example around 300 mg integrin alpha 10 subunit antibody should be administered to an adult human being per dose.

The composition of the present invention may be a pharmaceutical composition suitable for parenteral administration. Such compositions preferably include aqueous and non-aqueous sterile injection solutions which may contain wetting or emulsifying reagents, anti-oxidants, pH buffering agents, bacteriostatic compounds and solutes which render the formulation isotonic with the body fluid, preferably the blood, of the individual; and aqueous and non-aqueous sterile suspensions which may include suspending agents or thickening agents. The pharmaceutical composition may be presented in unit-dose or multi-dose containers, for example, sealed ampoules and vials and may be stored in a freeze-dried condition requiring only the addition of the sterile liquid carrier immediately prior to use.

Preferably, the composition of the present invention comprises one or more suitable pharmaceutical excipients, which could be non-sterile or sterile, for use with cells, tissues or organisms, such as pharmaceutical excipients suitable for administration to an individual. Such excipients may include, but are not limited to, saline, buffered saline, dextrose, water, glycerol, ethanol and combinations of these excipients in various amounts. The formulation should suit the mode of administration. The invention further relates to a pharmaceutical kit of parts comprising one or more containers filled with one or more of the ingredients of the aforementioned compositions of the invention. Examples of non-aqueous excipients are propylene glycol, polyethylene glycol, vegetable oils such as olive oil, and injectable organic esters such as ethyl oleate.

Preferably, the pharmaceutical compositions of the present invention are prepared in a form which is injectable, either as liquid solutions or suspensions; furthermore solid forms suitable for solution in or suspension in liquid prior to injection are also within the scope of the present invention. The preparation may be also be emulsified or encapsulated in liposomes.

The anti-integrin alpha 10 subunit antibody may be administered alone or in combination with other compounds, either simultaneously or sequentially in any order.

Administration could for example be parenteral via injection or infusion. Parenteral injection could for example be intraventricular, intratumoural, intravenous, intramuscular, intradermal or subcutanous injection. Preferably, said administration is parenterally by injection or infusion.

The anti-integrin alpha 10 subunit antibody should be administered as often as required, hence the anti-integrin alpha 10 subunit antibody may be administered more than once, such as at least two times, for example at least 3 times, such as at least 4 times, for example at least 5 times, such as in the range of 1 to 100 times, for example in the range of 1 to 50 times, such as in the range of 1 to 25 times, for example in the range of 1 to 10 times.

Preferably, there is at least 1 day between 2 administrations, such as at least 2 days, for example at least 3 days, such as at least 5 days, for example at least one week, such as at least 2 weeks, for example at least one month, such as at least 6 months, for example at least 1 year, such at least 2 years, for example at least 3 years, such as at least 5 years, for example at least 10 years.

Chemotherapeutic agents can be targeted to malignant neoplasms of the CNS, such as glioma, using integrin alpha-10 binding proteins, such as anti-integrin alpha-10 antibodies. In other embodiments, malignant neoplasms of the CNS such as glioma can be treated with anti-integrin alpha 10 subunit antibodies with appropriate effector function such as the ability to activate complement.

In one aspect the present invention concerns a composition for use in the treatment of a malignant neoplasm in the central nervous system, said composition comprising an antibody specifically binding to integrin alpha 10 subunit.

In one embodiment the antibody specifically binds to a polypeptide comprising or consisting of SEQ ID NO: 2 (the extracellular domain of integrin alpha10), and in another embodiment the antibody specifically binds to a polypeptide comprising or consisting of SEQ ID NO: 3 (the extracellular I-domain of integrin alpha10).

In one embodiment the antibody is selected from the group consisting of a monoclonal antibody, a polyclonal antibody and an antibody fragment, such as an antibody fragment selected from the group consisting of a Fab-fragment, a Fab' fragment, a $F(ab')_2$ fragment and an Fv fragment, such as a single-chain variable fragment (scFv) and a single-domain antibody.

Antibodies used for therapeutic applications are preferably chimeric, humanized or fully human antibodies, preferably with a human constant region.

In one embodiment the antibody is a non-human antibody, a chimeric antibody, a humanised antibody, a human antibody or a heterospecific antibody such as a bispecific antibody.

The antibody may have an isotype selected from the group consisting of IgA, IgD, IgG and IgM. IgG isotypes may e.g. be selected from the group consisting of IgG1, IgG2, IgG3 and IgG4.

In a specific embodiment the antibody is:

a. a monoclonal antibody produced by the hybridoma deposited at the Deutsche Sammlung von Microorganismen und Zellkulturen GmbH under the accession number DSM ACC2583 or an antigen-binding fragment thereof, wherein the antibody or antigen-binding fragment specifically binds to the extracellular I-domain of the integrin alpha10 chain; or
b. an antibody which competes for binding to the same epitope as the epitope bound by the monoclonal antibody produced by the hybridoma deposited at the Deutsche Sammlung von Microorganismen und Zellkulturen GmbH under the accession number DSM ACC2583; or
c. a fragment of a) or b), wherein said fragment is capable of binding specifically to the extracellular I-domain of the integrin alpha 10 subunit chain.

In one embodiment the anti-alpha10 antibody of the invention is an antibody capable of blocking cellular function via the integrin alpha 10 beta 1.

The antibody may be covalently bound to cytotoxic moiety, such as a cytotoxic moiety selected from a toxin, a chemotherapeutic agent and a radioactive agent.

In one embodiment the toxin is a ribosome inactivating protein, such as a ribosome inactivating protein selected from the group consisting of trichosanthin and luffin; type II ribosome inactivating proteins, such as ricin, agglutinin and abrin; and saporin.

In one embodiment the toxin is saporin. Saporin is a plant enzyme, a 30 kDa protein, with N-glycosidase activity that depurinates a specific nucleotide in 28S ribosomal RNA, irreversibly blocking protein synthesis. It belongs to the well characterized family of Ribosome Inactivating Proteins (RIP). Targeted SAP conjugates are powerful and specific lesioning agents used in the technique known as Molecular Surgery. Saporin (from the seeds of the plant, *Saponaria officinalis*) may be bound to a targeting agent, in this case an anti-integrin alpha antibody and administered to cells (in vitro or in vivo). The targeting agent seeks out and binds to its target on the cell surface. The conjugate is internalized, saporin breaks away from the targeting agent, and inactivates the ribosomes which causes protein inhibition and, ultimately, cell death. Cells that do not have the cell surface marker are not affected.

In one embodiment, a chemotherapeutic agent is covalently bound to the antibody. In other embodiments, a chemotherapeutic agent is encapsulated in a nanoparticle such as a liposome and the particle is targeted to the glioma by having anti-integrin alpha 10 subunit antibodies bound to their surface.

Antibody-Drug Conjugates (ADCs) such as an anti-integrin alpha 10 subunit antibody conjugated to saporin may be prepared by those of skill in the art e.g. as exemplified in Bidard and Tredan (2014) Targ Oncol 9:1-8 or Agarwal and Bertozzi (2015) Bioconjugate Chem. 26:176-192.

In one embodiment the composition for use in the treatment of a malignant neoplasm of the CNS comprises an antibody which is covalently bound to a biological response modifier, such as a cytokine, e.g. a cytokine selected from a lymphokine and an interferon.

The composition for use in the treatment may comprise further active ingredients such as one or more chemotherapeutic agents and optionally a pharmaceutically acceptable diluent, carrier or excipient.

The antibody of the invention is in one embodiment designed to be specific for integrin alpha 10 subunit and in another embodiment designed to be specific to a naturally occurring variant of integrin alpha 10 subunit, e.g. an isoform of integrin alpha 10 subunit or a splice variant of an integrin alpha 10 subunit.

In one embodiment the present invention concerns an antibody which binds to both the alpha 10 and the beta 1 subunits of the integrin alpha 10 beta 1 heterodimer.

In another embodiment the present invention concerns an antibody which binds to the alpha 10 but not to the beta 1 subunits of the integrin alpha 10 beta 1 heterodimer.

In one embodiment the antibody is capable of inducing cell death and/or inhibiting the growth and/or proliferation of the cells expressing the integrin alpha 10 subunit.

In one embodiment the antibody is capable of inducing cell death of the cells expressing the integrin alpha 10 subunit. In one embodiment the antibody is capable of inhibiting the growth of the cells expressing the integrin alpha 10 subunit. In one embodiment the antibody is capable of inhibiting the proliferation of the cells expressing the integrin alpha 10. In one embodiment the antibody is capable of inhibiting the migration of the cells expressing the integrin alpha 10.

In one embodiment the cells further express one or more of EGFRvIII, Nestin, PSA-NCAM, GFAP, PDGFRb (CD140b), PECAM-1 (CD31), CD45, CD68, CD163 and/or CD206.

In one embodiment the cells further express EGFRvIII. In one embodiment the cells further express Nestin. In one embodiment the cells further express PSA-NCAM. In one embodiment the cells further express GFAP. In one embodiment the cells further express PDGFRb (CD140b). In one embodiment the cells further express PECAM-1 (CD31). In one embodiment the cells further express CD45. In one embodiment the cells further express CD68. In one embodiment the cells further express CD163. In one embodiment the cells further express CD206.

Thus, in one embodiment the present invention relates to a method for inducing cell death and/or inhibiting the growth and/or proliferation of cells associated with a malignant neoplasm in the central nervous system, wherein the cell expresses an integrin alpha 10 subunit and optionally one or more of EGFRvIII, Nestin, PSA-NCAM, GFAP, PDGFRb (CD140b), PECAM-1 (CD31), CD45, CD68, CD163 and/or CD206.

In one embodiment the cells associated with the malignant neoplasm in the central nervous system are malignant cells or tumour-associated cells.

Examples of malignant cells or tumour-associated cells include glial cells; astrocytes; pericytes; endothelial cells; hematopoietic cells; and microglia.

In one embodiment the cells are glial cells.

The hematopoietic cells may e.g. be selected from the group consisting of hematopoietic stem cells, T-cells, B-cells, plasma cells, NK-cells, dendritic cells, macrophages and monocytes.

In one embodiment the macrophage is a tumour-associated macrophage (TAM).

Clinical Conditions

The clinical condition according to the present invention may be treatment of any one of the malignant neoplasms of the CNS as defined herein, including curative, ameliorating or prophylactic treatment by administration of the anti-integrin alpha 10 subunit antibodies of the invention.

The composition defined herein above is for use in the treatment of a malignant neoplasm selected from the groups consisting of:

a) Tumours of neuroepithelial tissue selected from i) Astrocytic tumours selected from Pilocytic astrocytoma (ICD-O 9421/1, WHO grade I), Pilomyxoid astrocytoma (ICD-O 9425/3, WHO grade II), Subependymal giant cell astrocytoma (ICD-O 9384/1, WHO grade I), Pleomorphic xanthoastrocytoma (ICD-O 9424/3, WHO grade II), Diffuse astrocytoma (ICD-O 9400/3, WHO grade II), Anaplastic astrocytoma (ICD-O 9401/3, WHO grade III), Glioblastoma (ICD-O 9440/3, WHO grade IV), Giant cell glioblastoma (ICD-O 9441/3, WHO grade IV), Gliosarcoma (ICD-O 9442/3, WHO grade IV), Gliomatosis cerebri (ICD-O 9381/3, WHO grade III), and ii) Oligodendroglial tumours selected from Oligodendroglioma (ICD-O 9450/3, WHO grade II) and Anaplastic oligodendroglioma (ICD-O 9451/3, WHO grade III), and iii) Oligoastrocytic tumours selected from Oligoastrocytoma (ICD-O 9382/3, WHO grade II) and Anaplastic oligodendroglioma (ICD-O 9382/3, WHO grade III), and iv) Ependymal tumours selected from Subependymoma (ICD-O 9383/1, WHO grade I), Myxopapillary ependymoma (ICD-O 9394/1, WHO grade I), Ependymoma (ICD-O 9391/3, WHO grade II), Anaplastic ependymoma (ICD-O 9392/3, WHO grade III), and v) Choroid plexus tumours selected from Choroid plexus papilloma (ICD-O 9390/0, WHO grade I), Atypical choroid plexus papilloma (ICD-O 9390/1, WHO grade II), and Choroid plexus carcinoma (ICD-O 9390/3, WHO grade III), and vi) Other neuroepithelial tumours selected from Astroblastoma (ICD-O 9430/3, WHO grade I), Chordoid glioma of the third ventricle (ICD-O 9444/1, WHO grade II), and Angiocentric glioma (ICD-O 9431/1, WHO grade I) and, vii) Neuronal and mixed neuronal-glial tumours selected from Dysplastic gangliocytoma of cerebellum (Lhermitte-Duclos) (ICD-O 9493/0), Desmoplastic infantile astrocytoma/ganglioglioma (ICD-O 9412/1, WHO grade I), Dysembryoplastic neuroepithelial tumour (ICD-O 9413/0, WHO grade I), Gangliocytoma (ICD-O 9492/0, WHO grade I), Ganglioglioma (ICD-O 9505/1, WHO grade I), Anaplastic ganglioglioma (ICD-O 9505/3, WHO grade III), Central neurocytoma (ICD-O 9506/1, WHO grade II), Extraventricular neurocytoma (ICD-O 9506/1, WHO grade II), Cerebellar liponeurocytoma (ICD-O 9506/1, WHO grade II), Papillary glioneuronal tumour (ICD-O 9509/1, WHO grade I), Rosette-forming glioneuronal tumour of the fourth ventricle (ICD-O 9509/1, WHO grade I), and Paraganglioma (ICD-O 8680/1, WHO grade I), and viii) Tumours of the pineal region selected from Pineocytoma (ICD-O 9361/1, WHO grade I), Pineal parenchymal tumour of intermediate differentiation (ICD-O 9362/3, WHO grade II, III), Pineoblastoma (ICD-O 9362/3, WHO grade IV), and Papillary tumours of the pineal region (ICD-O 9395/3, WHO grade II, III), and ix) Embryonal tumours selected from Medulloblastoma (ICD-O 9470/3, WHO grade IV), Medulloblastoma with extensive nodularity (ICD-O 9471/3, WHO grade IV), Anaplastic medulloblastoma (ICD-O 9474/3, WHO grade IV), CNS Primitive neuroectodermal tumour (ICD-O 9473/3, WHO grade IV), CNS Neuroblastoma (ICD-O 9500/3, WHO grade IV), and Atypical teratoid/rhabdoid tumour (ICD-O 9508/3, WHO grade IV), and b) Tumours of cranial and paraspinal nerves selected from
   i) Schwannoma (ICD-O 9560/0, WHO grade I)
   ii) Neurofibroma (ICD-O 9540/0, WHO grade I),
   iii) Perineurioma (ICD-O 9571/0, 9571/3, WHO grade I, II, III), and
   iv) Malignant peripheral nerve sheath tumour (MPNST) (ICD-O 9540/3, WHO grade II, III, IV), and
c) Tumours of the meninges selected from
   i) Tumours of meningothelial cells, selected from Meningioma (ICD-O 9530/0, WHO grade I), Atypical meningioma (ICD-O 9539/1, WHO grade II), Anaplastic meningioma (ICD-O 9530/3, WHO grade III), and
   ii) Mesenchymal tumours selected from Lipoma (ICD-O 8850/0), Angiolipoma (ICD-O 8861/0), Hibernoma (ICD-O 8880/0), Liposarcoma (ICD-O 8850/3), Solitary fibrous tumour (ICD-O 8815/0), Fibrosarcoma (ICD-O 8810/3), Malignant fibrous histiocytoma (ICD-O 8830/3), Leiomyoma (ICD-O 8890/0), Leiomyosarcoma (ICD-O 8890/3), Rhabdomyoma (ICD-O 8900/0), Rhabdomyosarcoma (ICD-O 8900/3), Chondroma (ICD-O 9220/0), Chondrosarcoma (ICD-O 9220/3), Osteoma (ICD-O 9180/0), Osteosarcoma (ICD-O 9180/3), Osteochondroma (ICD-O 9210/0), Haemangioma (ICD-O 9120/0), Epithelioid hemangioendothelioma (ICD-O 9133/1), Haemangiopericytoma (ICD-O 9150/1, WHO grade II), Anaplastic haemangiopericytoma (ICD-O 9150/3, WHO grade III), and Angiosarcoma (ICD-O 9120/3)3.2.22 Kaposi Sarcoma (ICD-O 9140/3), Ewing Sarcoma—PNET (ICD-O 9364/3), and
   iii) Primary melanocytic lesions selected from Diffuse melanocytosis (ICD-O 8728/0), Melanocytoma (ICD-O 8728/1) Malignant melanoma (ICD-O 8720/3), Meningeal melanomatosis (ICD-O 8728/3), and
   iv) Other neoplasms related to the meninges such as Haem-angioblastoma (ICD-O 9161/1, WHO grade I), and
d) Tumours of the haematopoietic system selected from
   i) Malignant Lymphomas (ICD-O 9590/3)4.2 Plasmocytoma (ICD-O 9731/3), and
   ii) Granulocytic sarcoma (ICD-O 9930/3), and
e) Tumours of the sellar region selected from
   i) Craniopharyngioma (ICD-O 9350/1, WHO grade I)
   ii) Granular cell tumour (ICD-O 9582/0, WHO grade I)
   iii) Pituicytoma (ICD-O 9432/1, WHO grade I), and
   iv) Spindle cell oncocytoma of the adenohypophysis (ICD-O 8991/0, WHO grade I)

In one embodiment the malignant neoplasm to be treated by the anti-integrin alpha 10 antibody or composition comprising an anti-integrin alpha 10 antibody of the present invention is a glioma.

In one embodiment the malignant neoplasm to be treated by the anti-integrin alpha 10 antibody or composition comprising an anti-integrin alpha 10 antibody of the present invention is a grade II, III or IV glioma.

In one embodiment the malignant neoplasm to be treated by the anti-integrin alpha 10 antibody or composition comprising an anti-integrin alpha 10 antibody of the present invention is an astrocytoma, such as astrocytoma grade II, astrocytoma grade III or astrocytoma grade IV.

In one embodiment the glioma to be treated by the anti-integrin alpha 10 antibody or composition comprising an anti-integrin alpha 10 antibody of the present invention is a glioblastoma.

In one embodiment the glioma is primary glioblastoma.

In one embodiment the glioma is secondary glioblastoma.

In one embodiment the malignant neoplasm to be treated by the anti-integrin alpha 10 antibody or composition comprising an anti-integrin alpha 10 antibody of the present invention is medulloblastoma.

In one embodiment the malignant neoplasm to be treated by the anti-integrin alpha 10 antibody or composition comprising an anti-integrin alpha 10 antibody of the present invention is neuroblastoma.

In one embodiment the malignant neoplasm to be treated by the composition of the present invention is selected from the group consisting of astrocytomas, anaplastic astrocytomas, hemangiopericytomas of the brain, meningiomas, angiomatous hemangiomas, atypical meningiomas, fibroblastic meningiomas, meningiothelial meningiomas, secretory meningiomas, oligoastrocytomas, anaplastic oligoastrocytomas, oligodendrogliomas, and anaplastic oligodendrogliomas.

In one embodiment the malignant neoplasm to be treated by the composition of the present invention is selected from the group consisting of Astrocytic tumours, Oligodendroglial tumours, Ependymal cell tumours, Mixed gliomas, Neuroepithelial tumours of uncertain origin, Tumours of the choroid plexus, Neuronal and mixed neuronal-glial tumours, Pineal Parenchyma Tumours and Tumours with neuroblastic or glioblastic elements (embryonal tumours), ependymomas, astrocytomas, oligodendrogliomas, oligoastrocytomas, neuroepithelal tumours, and neuronal and mixed neuronal-glial tumours.

In one aspect the invention concerns a method of treatment of a malignant neoplasm in the central nervous system of a subject in need thereof, said method comprising administering to said subject an antibody specifically binding to an integrin alpha 10 subunit. Said treatment may be prophylactic, ameliorative or curative.

The treatment defined herein above may be initiated upon detection of an integrin alpha 10 subunit in said subject.

In one aspect the invention concerns a method of treating a subject suffering from a malignant neoplasm in the central nervous system, said method comprising:

a) determining if a subject is suffering from a malignant neoplasm of the central nervous system by a detection method defined herein; and
b) administering to a subject diagnosed with a malignant neoplasm of the central nervous system, a therapeutically effective amount of an antibody specifically binding to an integrin alpha 10 subunit to said subject.

In one aspect the invention concerns the use of a composition comprising an antibody specifically binding to an integrin alpha 10 subunit for the manufacture of a medicament for the treatment of a malignant neoplasm in the central nervous system.

In another aspect the invention concerns a method of inhibiting tumour associated vascularization in a mammal, the method comprising administering to said mammal a therapeutically effective amount of an anti-integrin alpha 10 subunit antibody.

In one embodiment the present invention relates to a method for inhibiting the growth and/or proliferation of a cell expressing integrin alpha 10 subunit comprising administering an effective amount of an anti-integrin alpha 10 subunit antibody to said cell. The cell may express one or more further markers as defined herein. In a particularly preferred embodiment said cell is a glioma cell. Said method may be performed in vitro or in vivo.

In one embodiment the present invention relates to a method for decreasing the tumorigenic or metastatic potential of a cell expressing integrin alpha 10 subunit comprising administering an effective amount of an anti-integrin alpha 10 subunit antibody to said cell. The cell may express one or more further markers as defined herein. In a particularly preferred embodiment said cell is a glioma cell. Said method may be performed in vitro or in vivo. Data presented herein shows that treatment of glioma (GBM) cells expressing integrin alpha 10 subunit with an anti-integrin alpha 10 subunit antibody significantly decreases sphere formation capacity, thus indicating that treatment with an anti-integrin alpha 10 subunit antibody inhibits or at least decreases the ability of integrin alpha 10 subunit-expressing cells to form tumours.

In further embodiments, methods of therapy involve acquiring an image of the central nervous system to detect the location of the glioma using methods described herein, preferably wherein the location is detected in 3D space and using the information about the location to guide subsequent radiation therapy to treat the glioma.

In still further embodiments, a surgeon can use an integrin alpha 10 subunit specific molecular probe to detect the presence of glioma during surgery.

II. Detection and Diagnosis of Malignant Neoplasms of the Central Nervous System The present invention also concerns a method for detecting a malignant neoplasm in the central nervous system of a mammal, said method comprising analysing in an isolated sample, the presence or absence of:

a) an antigen comprising an integrin alpha 10 subunit polypeptide, or
b) a polynucleotide transcript which encodes an integrin alpha 10 subunit polypeptide or a fragment or variant thereof, wherein presence of the antigen of a) or the polynucleotide transcript of b) is indicative of a malignant neoplasm in the central nervous system of said mammal.

In another aspect the present invention concerns a method for detecting a malignant neoplasm in the central nervous system of a mammal, said method comprising the steps of:

a) administering to a subject a molecular probe capable of binding specifically to an integrin alpha 10 subunit polypeptide, or to an integrin alpha 10 subunit polynucleotide transcript, said probe being covalently bound to a moiety capable of emitting photons,
b) detecting photons emitted from said moiety and forming an image of the central nervous system or part thereof, wherein localised emission of photons from said moiety is indicative of a malignant neoplasm in the central nervous system of said mammal.

In another aspect the invention concerns an in vitro diagnostic method to diagnose a malignant neoplasm in the central nervous system of a mammal, said method comprising the steps of:

a) contacting an in vitro sample with a molecular probe capable of binding specifically to an integrin alpha 10 subunit polypeptide, or to an integrin alpha 10 subunit polynucleotide transcript, said probe being covalently bound to a moiety capable of emitting photons,
b) detecting photons emitted from said moiety and forming an image of the sample, wherein localised emission of photons from said moiety is indicative of a malignant neoplasm in the central nervous system of said mammal.

In another aspect the present invention concerns an in vitro method for the detection of integrin alpha 10 subunit in an isolated sample, said method comprising analysing in said isolated sample, the presence or absence of:

a) an antigen comprising an integrin alpha 10 subunit polypeptide, or
b) a polynucleotide transcript which encodes an integrin alpha 10 subunit polypeptide or a fragment or variant thereof, wherein presence of the antigen of a), or the polynucleotide transcript of b) is indicative of a malignant neoplasm in said isolated sample.

In another aspect, the present invention relates to an agent comprising or consisting of an antibody with specificity for integrin alpha 10 subunit for use in detecting cells associated with a malignant neoplasm of the central nervous system of a mammal, wherein the cells express integrin alpha 10 subunit.

In another aspect the present invention relates to an in vitro diagnostic method to diagnose a malignant neoplasm in the central nervous system of a mammal, said method comprising the steps of:

a) contacting an in vitro sample obtained from said mammal with a molecular probe capable of binding specifically to an integrin alpha 10 subunit polypeptide, or to an integrin alpha 10 subunit polynucleotide transcript, said probe being covalently bound to a moiety capable of emitting photons,
b) detecting photons emitted from said moiety and forming an image of the sample, wherein localised emission of photons from said moiety is indicative of a malignant neoplasm in the central nervous system of said mammal.

In another aspect the present invention relates to an in vitro method for the detection of integrin alpha 10 subunit in an isolated sample obtained from a mammal, said method comprising analysing in said isolated sample, the presence or absence of:

a) an antigen comprising an integrin alpha 10 subunit polypeptide; and/or
b) a polynucleotide transcript which encodes an integrin alpha 10 subunit polypeptide or a fragment or variant thereof, wherein presence of the antigen of a), and/or the polynucleotide transcript of b) is indicative of a malignant neoplasm in the central nervous system of said mammal.

In another aspect the present invention concerns use of an anti-integrin alpha 10 subunit-specific antibody which binds specifically to integrin alpha 10 subunit to detect a malignant neoplasm of the central nervous system in a biological sample in vitro, in situ or in vivo.

In another aspect the present invention concerns use of an integrin alpha 10 subunit nucleic acid probe which binds to an integrin alpha 10 subunit mRNA or cDNA in a hybridizing reaction to detect a malignant neoplasm of the central nervous system in a biological sample in vitro, in situ or in vivo.

In another aspect the present invention concerns use of an integrin alpha 10 subunit nucleic acid probe compound in the preparation of a kit for diagnosing a malignant neoplasm of the central nervous system.

In another aspect the present invention concerns use of an anti-integrin alpha 10 subunit-specific antibody which binds to integrin alpha 10 subunit, in the preparation of a kit for diagnosing a malignant neoplasm of the central nervous system.

In another aspect the present invention concerns use of an integrin alpha 10 subunit nucleic acid probe compound, for the manufacture of a diagnostic agent for diagnosing, monitoring or determining if a subject has a malignant neoplasm of the central nervous system, wherein said diagnostic agent is manufactured to measure presence of an integrin alpha 10 subunit polynucleotide in a biological sample, wherein presence of said integrin alpha 10 subunit polynucleotide in said sample is indicative of a malignant neoplasm of the central nervous system of said subject.

In another aspect the present invention concerns use of an anti-integrin alpha 10 subunit-specific antibody which binds to integrin alpha 10 subunit, for the manufacture of a diagnostic agent for diagnosing, monitoring or determining if a mammal has a malignant neoplasm of the central nervous system, wherein said diagnostic agent is manufactured to measure presence of an integrin alpha 10 subunit polypeptide in a sample, wherein presence of said integrin alpha 10 subunit polypeptide in said sample is indicative of a malignant neoplasm of the central nervous system of said mammal.

In another aspect the present invention concerns a method for detecting a malignant or tumour-associated mammalian cell, said method comprising analysing in an isolated sample, the presence or absence of:

a) a first antigen comprising an integrin alpha 10 subunit polypeptide; and/or
b) a first polynucleotide transcript which encodes an integrin alpha 10 subunit polypeptide or a fragment or variant thereof;

and c) a second antigen comprising a polypeptide selected from the group consisting of EGFRvIII, Nestin, PSA-NCAM, GFAP, PDGFRb (CD140b), PECAM-1 (CD31), CD45, CD68, CD163 and CD206; and/or
d) a second polynucleotide transcript which encodes a polypeptide or a fragment or variant thereof, wherein said polypeptide is selected from the group consisting of EGFRvIII, Nestin, PSA-NCAM, GFAP, PDGFRb (CD140b), PECAM-1 (CD31), CD45, CD68, CD163, and CD206.

The presence of the first antigen of a) and/or the first polynucleotide transcript of b); together with the second antigen of c) and/or the second transcript of d), indicates that said mammalian cell is a malignant cell or a tumour-associated cell.

In another aspect the present invention concerns a method for detecting a malignant or tumour-associated cell of a mammal, said method comprising the steps of:

a) administering to a mammal a first molecular probe capable of binding specifically to an integrin alpha 10 subunit polypeptide; and/or to an integrin alpha 10 subunit polynucleotide transcript, said first probe being covalently bound to a first moiety capable of emitting photons; and
b) administering to a mammal a second molecular probe capable of binding specifically to a polypeptide selected from the group consisting of EGFRvIII, Nestin, PSA-NCAM, GFAP, PDGFRb (CD140b), PECAM-1 (CD31), CD45, CD68, CD163, and CD206; and/or to a polynucleotide transcript encoding a polypeptide selected from the group consisting of EGFRvIII, Nestin, PSA-NCAM, GFAP, PDGFRb (CD140b), PECAM-1 (CD31), CD45, CD68, CD163, and CD206, said second probe being covalently bound to a second moiety capable of emitting photons;
c) detecting photons emitted from said first and said second moieties, thus forming an image of the central nervous system or part thereof.

The localised emission of photons from said first and said second moiety is indicative of a malignant or tumour-associated cell of said mammal.

Malignant Neoplasms of the CNS

Malignant neoplasms are classified in two ways. They are phenotypically classified according to their apparent morphology and they are graded according to their severity. This grading is also based on histologic features of the tumour.

In gliomas for example, malignant neoplasms are named astrocytomas when they morphologically appear to be astrocyte-like and oligodendrogliomas when malignant cells morphologically appear to be oligodendrocyte-like. There are also mixed forms of glioma, in this case named oligoastrocytomas.

Tumour grade is an indicator of how quickly a tumour is likely to grow and spread. If the cells of the tumour and the organization of the tumour's tissue are close to those of normal cells and tissue, the tumour is called well-differentiated (low grade). These tumours tend to grow and spread at a slower rate than tumours that are poorly differentiated or undifferentiated, which have abnormal-looking cells and grow faster (high grade). See FIG. 1 for an example of glioma classification.

The WHO grading of CNS tumours establishes a malignancy scale based on histologic features of the tumour. The histologic grades are as follows: WHO grade I includes lesions with low proliferative potential, a frequently discrete nature, and the possibility of cure following surgical resection alone. WHO grade II includes lesions that are generally infiltrating and low in mitotic activity but recur more frequently than grade I malignant tumours after local therapy. Some tumour types tend to progress to higher grades of malignancy. WHO grade III includes lesions with histologic evidence of malignancy, including nuclear atypia and increased mitotic activity. These lesions have anaplastic histology and infiltrative capacity. They are usually treated with aggressive adjuvant therapy. WHO grade IV includes lesions that are mitotically active, necrosis-prone, and generally associated with a rapid preoperative and postoperative progression and fatal outcomes. The lesions are usually treated with aggressive adjuvant therapy.

For a complete and current classification please see the new World Health Organization (WHO) classification of nervous system tumours, published in 2000, emerged from a 1999 international consensus conference of neuropathologists (Kleihues and Cavanee, Eds., 2000: Pathology and Genetics of Tumours of the Nervous System. Lyon, France: International Agency for Research on Cancer; Kleihues et al. (2002) The WHO Classification of Tumours of the Nervous System. *Journal of Neuropathology & Experimental Neurology* 61:215-225). The actual classification is accompanied by extensive descriptions and illustrations of clinicopathological characteristics of each tumour type, including molecular genetic features, predictive factors, and separate chapters on inherited tumour syndromes.

The present disclosure relates to detection and/or treatment of malignant neoplasms in the CNS characterized by integrin alpha 10 subunit expression. Thus, in one embodiment the malignant neoplasm of the CNS is a selected from the groups consisting of:

a) Tumours of neuroepithelial tissue selected from i) Astrocytic tumours selected from Pilocytic astrocytoma (ICD-O 9421/1, WHO grade I), Pilomyxoid astrocytoma (ICD-O 9425/3, WHO grade II), Subependymal giant cell astrocytoma (ICD-O 9384/1, WHO grade I), Pleomorphic xanthoastrocytoma (ICD-O 9424/3, WHO grade II), Diffuse astrocytoma (ICD-O 9400/3, WHO grade II), Anaplastic astrocytoma (ICD-O 9401/3, WHO grade III), Glioblastoma (ICD-O 9440/3, WHO grade IV), Giant cell glioblastoma (ICD-O 9441/3, WHO grade IV), Gliosarcoma (ICD-O 9442/3, WHO grade IV), Gliomatosis cerebri (ICD-O 9381/3, WHO grade III), and ii) Oligodendroglial tumours selected from Oligodendroglioma (ICD-O 9450/3, WHO grade II) and Anaplastic oligodendroglioma (ICD-O 9451/3, WHO grade III), and iii) Oligoastrocytic tumours selected from Oligoastrocytoma (ICD-O 9382/3, WHO grade II) and Anaplastic oligoastrocytoma (ICD-O 9382/3, WHO grade III), and iv) Ependymal tumours selected from Subependymoma (ICD-O 9383/1, WHO grade I), Myxopapillary ependymoma (ICD-O 9394/1, WHO grade I), Ependymoma (ICD-O 9391/3, WHO grade II), Anaplastic ependymoma (ICD-O 9392/3, WHO grade III), and v) Choroid plexus tumours selected from Choroid plexus papilloma (ICD-O 9390/0, WHO grade I), Atypical choroid plexus papilloma (ICD-O 9390/1, WHO grade II), and Choroid plexus carcinoma (ICD-O 9390/3, WHO grade III), and vi) Other neuroepithelial tumours selected from Astroblastoma (ICD-O 9430/3, WHO grade I), Chordoid glioma of the third ventricle (ICD-O 9444/1, WHO grade II), and Angiocentric glioma (ICD-O 9431/1, WHO grade I) and, vii) Neuronal and mixed neuronal-glial tumours selected from Dysplastic gangliocytoma of cerebellum (Lhermitte-Duclos) (ICD-O 9493/0), Desmoplastic infantile astrocytoma/ganglioglioma (ICD-O 9412/1, WHO grade I), Dysembryoplastic neuroepithelial tumour (ICD-O 9413/0, WHO grade I), Gangliocytoma (ICD-O 9492/0, WHO grade I), Ganglioglioma (ICD-O 9505/1, WHO grade I), Anaplastic ganglioglioma (ICD-O 9505/3, WHO grade III), Central neurocytoma (ICD-O 9506/1, WHO grade II), Extraventricular neurocytoma (ICD-O 9506/1, WHO grade II), Cerebellar liponeurocytoma (ICD-O 9506/1, WHO grade II), Papillary glioneuronal tumour (ICD-O 9509/1, WHO grade I), Rosette-forming glioneuronal tumour of the fourth ventricle (ICD-O 9509/1, WHO grade I), and Paraganglioma (ICD-O 8680/1, WHO grade I), and viii) Tumours of the pineal region selected from Pineocytoma (ICD-O 9361/1, WHO grade I), Pineal parenchymal tumour of intermediate differentiation (ICD-O 9362/3, WHO grade II, III), Pineoblastoma (ICD-O 9362/3, WHO grade IV), and Papillary tumours of the pineal region (ICD-O 9395/3, WHO grade II, III), and ix) Embryonal tumours selected from Medulloblastoma (ICD-O 9470/3, WHO grade IV), Medulloblastoma with extensive nodularity (ICD-O 9471/3, WHO grade IV), Anaplastic medulloblastoma (ICD-O 9474/3, WHO grade IV), CNS Primitive neuroectodermal tumour (ICD-O 9473/3, WHO grade IV), CNS Neuroblastoma (ICD-O 9500/3, WHO grade IV), and Atypical teratoid/rhabdoid tumour (ICD-O 9508/3, WHO grade IV), and b) Tumours of cranial and paraspinal nerves selected from i) Schwannoma (ICD-O 9560/0, WHO grade I)

ii) Neurofibroma (ICD-O 9540/0, WHO grade I), iii) Perineurioma (ICD-O 9571/0, 9571/3, WHO grade I, II, III), and iv) Malignant peripheral nerve sheath tumour (MPNST) (ICD-O 9540/3, WHO grade II, III, IV), and c) Tumours of the meninges selected from i) Tumours of meningothelial cells, selected from Meningioma (ICD-O 9530/0, WHO grade I), Atypical meningioma (ICD-O 9539/1, WHO grade II), Anaplastic meningioma (ICD-O 9530/3, WHO grade III), and ii) Mesenchymal tumours selected from Lipoma (ICD-O 8850/0), (ICD-O 8850/3), Solitary fibrous tumour (ICD-O 8815/0), Fibrosarcoma (ICD-O 8810/3), Malignant fibrous histiocytoma (ICD-O 8830/3), Leiomyoma (ICD-O 8890/0), Leiomyosarcoma (ICD-O 8890/3), Rhabdomyoma (ICD-O 8900/0), Rhabdomyosarcoma (ICD-O 8900/3), Chondroma (ICD-O 9220/0), Chondrosarcoma (ICD-O 9220/3), Osteoma (ICD-O 9180/0), Osteosarcoma (ICD-O 9180/3), Osteo-chondroma (ICD-O 9210/0), Haemangioma (ICD-O 9120/0), Epithelioid hemangioendothelioma (ICD-O 9133/1), Haemangiopericytoma (ICD-O 9150/1, WHO grade II), Anaplastic haemangiopericytoma (ICD-O 9150/3, WHO grade III), and Angiosarcoma (ICD-O 9120/3)3.2.22 Kaposi Sarcoma (ICD-O 9140/3), Ewing Sarcoma—PNET (ICD-O 9364/3), and iii) Primary melanocytic lesions selected from Diffuse melanocytosis (ICD-O 8728/0), Melanocytoma (ICD-O 8728/1) Malignant melanoma (ICD-O 8720/3), Meningeal melanomatosis (ICD-O 8728/3), and iv) Other neoplasms related to the meninges such as Haem-angioblastoma (ICD-O 9161/1, WHO grade I), and d) Tumours of the haematopoietic system selected from i) Malignant Lymphomas (ICD-O 9590/3)4.2 Plasmocytoma (ICD-O 9731/3), and ii) Granulocytic sarcoma (ICD-O 9930/3), and e) Tumours of the sellar region selected from i) Craniopharyngioma (ICD-O 9350/1, WHO grade I)

ii) Granular cell tumour (ICD-O 9582/0, WHO grade I)

iii) Pituicytoma (ICD-O 9432/1, WHO grade I), and iv) Spindle cell oncocytoma of the adenohypophysis (ICD-O 8991/0, WHO grade I).

In one embodiment the malignant neoplasm detected and/or treated by the method of the present invention is a glioma, such as a grade II, III or IV glioma. In another embodiment the malignant neoplasm detected and/or treated by the method of the invention is an astrocytoma.

In certain embodiments the malignant neoplasm is a glioma such as a glioblastoma. The glioblastoma tumours detected by the present invention may also be selected from the group consisting of Astrocytic tumours, Oligodendroglial tumours, Ependymal cell tumours, Mixed gliomas, Neuroepithelial tumours of uncertain origin, Tumours of the choroid plexus, Neuronal and mixed neuronal-glial tumours, Pineal Parenchyma Tumours and Tumours with neuroblastic or glioblastic elements (embryonal tumours), ependymomas, astrocytomas, oligodendrogliomas, oligoastrocytomas, neuroepithelal tumours, and neuronal and mixed neuronal-glial tumours.

III. Integrin Alpha 10 Subunit

Integrins are heterodimers consisting of an alpha and a beta subunit. The integrin alpha 10 beta 1 heterodimer may be detected by anti-integrin alpha 10 subunit-specific antibodies and integrin alpha 10 subunit binding peptides and proteins. Integrin alpha 10 beta 1 is the most abundant collagen-binding integrin in cartilaginous tissues and its expression pattern is distinct from that of other collagen-binding integrins. In vitro and in vivo studies have identified integrin alpha 10 beta 1 as a unique phenotypic marker for chondrocyte differentiation and a crucial mediator of cell-matrix interactions required for proper cartilage development (Lundgren Åkerlund and Aszódi (2014) Adv Exp Med Biol. 819:61-71).

The integrin alpha 10 beta 1 was identified as a collagen type II binding receptor on chondrocytes in 1998 (Camper et al., 1998). Immunohistochemical analysis during development and in adult tissues has demonstrated a restricted localization of the marker to cartilage-containing tissues (Camper et al. 1998, Camper et al., 2001). Knockout mice lacking the marker have disorganized growth plates, decreased collagen in the matrix and shorter long-bones, further supporting its cell structural importance (Bengtsson et al., 2005). The amino acid sequence, variants, isoforms and sequence annotations can be found in Uniprot accession no 075578-ITA10_HUMAN.

Moreover, integrin alpha10 beta 1 is present on mesenchymal stem cells (MSCs) and increase during in vitro chondrogenesis in aggregate cultures. Extensive culture of MSCs down regulate integrin alpha 10 beta 1 while treatment of the cultured mesenchymal stem cells with Fibroblast Growth Factor-2 increase expression of integrin alpha 10 beta 1 together with cartilage specific molecules, such as collagen type II and aggrecan. This demonstrates that alpha 10 beta 1 is a cell surface biomarker of MSCs with chondrogenic potential (Varas et al., 2007).

Several different mouse brain structures, including whole brain, have earlier been analyzed for integrin alpha 10 subunit expression and it has been shown that there is no expression of integrin alpha 10 subunit in any of the healthy brain structures analyzed (WO 99/51639).

Thus the integrin alpha 10 subunit is an excellent biomarker for disease. Accordingly the present invention concerns detection of the antigen integrin alpha 10 subunit polypeptide, e.g. with antibodies directed specifically to SEQ ID NO: 1 (integrin alpha 10 subunit), SEQ ID NO: 2 (the extracellular domain of integrin alpha10) or SEQ ID NO: 3 (the extracellular I-domain of integrin alpha10). Further antigens are antigens being isoforms, splice variants or naturally occurring variants of the integrin alpha 10 subunit.

In one embodiment the malignant neoplasm of the CNS is detected or diagnosed by detecting presence or absence of an antigen being a variant of integrin alpha 10 subunit wherein said variant is at least 70% identical to SEQ ID NOs: 1, 2 or 3, e.g. a variant which is at least 75% identical to SEQ ID NOs: 1, 2 or 3, such as a variant which is at least 80% identical to SEQ ID NOs: 1, 2 or 3, e.g. a variant which is at least 85% identical to SEQ ID NOs: 1, 2 or 3, such as a variant which is at least 90% identical to SEQ ID NOs: 1, 2 or 3, e.g. a variant which is at least 95% identical to SEQ ID NOs: 1, 2 or 3, such as a variant which is at least 96% identical to SEQ ID NOs: 1, 2 or 3, e.g. a variant which is at least 97% identical to SEQ ID NOs: 1, 2 or 3, e.g. a variant which is at least 98% identical to SEQ ID NOs: 1, 2 or 3, e.g. a variant which is at least 99% identical to SEQ ID NOs: 1, 2 or 3, such as a variant which is at least 99.5% identical to SEQ ID NOs: 1, 2 or 3.

In one embodiment the malignant neoplasm of the CNS is detected or diagnosed by detecting presence or absence of an antigen being a fragment of integrin alpha 10 subunit wherein said fragment comprises at least 100 consecutive amino acids of SEQ ID NO: 1, preferably at least 200 consecutive amino acids of SEQ ID NO: 1, preferably at least 300 consecutive amino acids of SEQ ID NO: 1, preferably at least 400 consecutive amino acids of SEQ ID NO: 1, preferably at least 500 consecutive amino acids of SEQ ID NO: 1, preferably at least 600 consecutive amino acids of SEQ ID NO: 1, preferably at least 700 consecutive amino acids of SEQ ID NO: 1, preferably at least 800 consecutive amino acids of SEQ ID NO: 1, preferably at least 900 consecutive amino acids of SEQ ID NO: 1, preferably at least 1000 consecutive amino acids of SEQ ID NO: 1.

Integrin alpha 10 subunit can also be detected on nucleotide level by analyzing a sample for the presence of e.g. mRNA transcripts which upon translation generates an integrin alpha 10 subunit antigen as defined herein above.

Antibodies Directed Against Integrin Alpha 10 Subunit

In one embodiment the presence of an integrin alpha 10 subunit, typically as part of an integrin alpha 10 beta 1 heterodimer protein, in a biological sample is detected by using an anti-integrin alpha10-specific antibody which binds to the integrin alpha 10 subunit in an immunological reaction. Preferably, the antibody binds to the integrin alpha 10 subunit extracellular domain, but in certain embodiments the anti-integrin alpha 10 subunit antibody has overlapping specificity for the entire integrin alpha 10 beta 1 heterodimeric complex. This may e.g. mean that the antibody of the present invention binds to an epitope covering both the alpha 10 and beta 1 subunits.

The antibodies and functional equivalents thereof may be produced by any suitable method known to the person skilled in the art. In one embodiment the antibody of the invention is produced in a hybridoma cell line (e.g. the mAb 365 hybridoma cell line deposited at the Deutsche Sammlung von Microorganismen and Zellkulturen GmbH under the accession number DSM ACC2583), thus producing an antibody binding to the extracellular alpha10beta1-domain. For production of said hybridoma, a gene knockout mouse of the integrin alpha10beta1 may be used. The knockout mouse is described in WO 03/101497, included herein by reference.

One method of producing an antibody specifically recognising and binding an epitope within the extracellular domain or I-domain of the integrin alpha 10 subunit comprises the step of administering to a mammal the extracellular domain or I-domain of the integrin alpha 10 subunit or a fragment thereof or a functional homologue thereof. Said extracellular domain or I-domain of the integrin alpha 10 subunit or a fragment thereof or a functional homologue thereof may be any of the integrin alpha 10 subunit fragments and peptides described herein. The extracellular domain or I-domain of the integrin alpha 10 subunit or fragment thereof or functional homologue thereof administrated to said mammal is also designated the "integrin alpha 10 subunit antigen" or "integrin alpha 10 antigen" herein.

In one embodiment, the present invention relates to methods of producing an antibody capable of inhibiting the activity of an integrin alpha 10 subunit, wherein said antibody specifically recognises an epitope within the extracellular domain or I-domain of integrin alpha 10 subunit.

The integrin alpha 10 subunit antigen may be administrated to said mammal more than once, such as twice, for example 3 times, such as 3 to 5 times, for example 5 to 10 times, such as 10 to 20 times, for example 20 to 50 times, such as more than 50 times. It is also possible that different integrin alpha 10 subunit antigens are administered to the same mammal, either simultaneously of sequentially in any order.

In general, the integrin alpha 10 subunit antigen will be in an aqueous solution or suspension prior to administration. Furthermore, the integrin alpha 10 subunit antigen may be mixed with one or more other compounds. For example, the integrin alpha 10 subunit antigen may be mixed with one or more suitable adjuvants and/or with one or more carriers.

Adjuvants are any substance whose admixture with an administered antigen increases or otherwise modifies the immune response to said antigen. Suitable adjuvants are well known by those of skill in the art.

Carriers are scaffold structures, e.g. a polypeptide or a polysaccharide, to which an antigen is capable of being associated. A carrier may be present independently of an adjuvant. Suitable carriers are well known by those of skill in the art.

Methods of preparing monoclonal antibodies, mixtures of monoclonal antibodies or polycloncal antibodies are known in the art and are for example described in Antibodies: A Laboratory Manual, By Ed Harlow and David Lane, Cold Spring Harbor Laboratory Press, 1988.

In one embodiment the anti-integrin alpha 10 subunit of the present invention is an antibody capable of inhibiting the biological activity of an integrin alpha 10 subunit.

In one embodiment the antibody of the present invention has an isotype selected from the group consisting of IgA, IgD, IgG and IgM. In a further embodiment the antibody is an IgG isotype, such as an IgG isotype selected from the group consisting of IgG1, IgG2 (e.g. IgG2a), IgG3 and IgG4.

The invention contemplates both monoclonal and polyclonal antibodies and fragments thereof, antigen binding fragments and recombinant proteins thereof which are capable of binding integrin alpha 10 subunit.

In one embodiment the anti-integrin alpha 10 subunit-specific antibody used for detecting the presence of integrin alpha 10 subunit in a biological sample is a polyclonal antibody.

In one embodiment the antibody used for detecting the integrin alpha 10 subunit antigen is an antibody fragment. Antigen binding fragments of antibodies are fragments of antibodies retaining the ability to specifically bind to an antigen. Examples of antibody fragment of the present invention includes antibody fragments selected from the group consisting of a Fab-fragment, a Fab' fragment, a $F(ab')_2$ fragment and an Fv fragment, such as a single-chain variable fragment (scFv) and a single-domain antibody.

The antibody according to the invention may also be a chimeric antibody, i.e. an antibody comprising regions derived from different species. The chimeric antibody may for example comprise variable regions from one species of animal and constant regions from another species of animal. For example, a chimeric antibody can be an antibody having variable regions which derive from a mouse monoclonal antibody and constant regions which are human. Such antibodies may also be referred to as humanised antibodies.

In one embodiment the antibody is a heterospecific antibody such as a bispecific antibody, which is a protein or polypeptide, which comprises two different antigen binding sites with different specificities. For example, the bispecific antibody may recognise and bind to (a) an epitope on integrin alpha 10 subunit and (b) to another epitope on integrin alpha 10 subunit. It may thus recognise and bind to two different epitopes within the same antigen. The term "heterospecific antibody" is intended to include any protein or polypeptide, which has more than two different antigen binding site with different specificities. Accordingly, the invention includes, but is not limited to, bispecific, trispecific, tetraspecific, and other multispecific antibodies which are directed to integrin alpha 10 subunit.

In one embodiment the antibody specific for integrin alpha 10 subunit is:

a) a monoclonal antibody, produced by the hybridoma cell line deposited at the Deutsche Sammlung von Microorganismen und Zellkulturen GmbH under the accession number DSM ACC2583; or
b) an antibody which competes for binding to the same epitope as the epitope bound by the monoclonal antibody produced by the hybridoma deposited at the Deutsche Sammlung von Microorganismen und Zellkulturen GmbH under the accession number DSM ACC2583; or
c) a fragment of a) or b), wherein said fragment is capable of binding specifically to the extracellular I-domain of the integrin alpha 10 subunit chain.

To get a good signal to noise ratio when detecting the anti-integrin alpha 10 subunit antibody it may be necessary to conjugate a moiety to the antibody to facilitate detection.

In one embodiment the antibody is covalently bound to a detectable moiety, such as a detectable moiety selected from the group consisting of a fluorophore, an enzyme or a radioactive tracer. The integrin alpha 10 subunit antigen may also be detected by detecting a peptide, protein or polypeptide other than integrin alpha 10 subunit, wherein said other peptide, protein or polypeptide is capable of specifically binding to an integrin alpha 10 subunit antigen. In one embodiment said peptide, protein or polypeptide is linked to an enzyme, a fluorophore or a radioactive tracer. The radioactive tracer may e.g. be selected from a positron emitter, or a gamma emitter.

The person of skill in the art is capable of selecting the standard laboratory equipment for detection of the anti-integrin alpha 10 subunit antibodies, depending on the situation and physical state of the sample.

In one embodiment the person of skill in the art would conduct the detection step using flow cytometry such as Fluorescence-Activated Cell Sorting (FACS).

Typical immunological methods well known in the art include but are not limited to western blot, enzyme linked immunosorbent assay (ELISA), radioimmunoassay (RIA), immunohistochemistry (IHC), immunofluorescent assay.

Detecting integrin alpha 10 subunit can be achieved using methods well known in the art of detection and imaging, such as clinical imaging, such as conventional fluorescence microscopes, confocal microscope, 2-photon microscopes, Stimulated emission depletion (STED) etc.

Molecular Probes for Detection of Integrin Alpha 10 Subunit

Analysis of the biological sample for the presence of an integrin alpha 10 subunit antigen or an integrin alpha 10 subunit encoding polynucleotide can also be carried out by using a molecular probe (protein or polynucleotide) capable of binding or hybridizing to integrin alpha 10 subunit mRNA, cDNA or protein to detect its expression in the biological sample or by using PCR, preferably Q-PCR.

In one embodiment the integrin alpha 10 subunit specific polynucleotide probes are linked to a detectable moiety optionally capable of emitting photons. By using this embodiment the subject to be diagnosed or investigated may be illuminated using a source of light capable of exciting said detectable moiety e.g. a fluorophore. Methods for detecting photons include but is not limited to PET-scan and SPECT-scan.

In certain embodiments the detectable moiety is selected from the group consisting of a fluorophore, an enzyme or a radioactive tracer.

A polynucleotide transcript may also be detected using PCR, preferably Q-PCR.

In a further embodiment the presence of integrin alpha 10 subunit in a biological sample is detected by using an integrin alpha 10 subunit nucleic acid probe which binds to integrin alpha 10 subunit RNA or cDNA in a hybridizing reaction.

Exemplary nucleic acid integrin-alpha 10-specific targeting components include DNA-probes, antisense RNAs or RNAi, such as microRNAs, short interfering RNAs (siRNA) and short hairpin RNAs (shRNA).

Typical methods for detection of nucleic acids well known in the art include but are not limited to Northern blotting, Southern blotting, polymerase chain reaction (PCR), microarrays, in situ hybridization etc.

In a further embodiment the presence of integrin alpha 10 subunit in a biological sample is detected by using an integrin alpha 10 subunit binding peptide or protein.

Such peptides or proteins can be made recombinant, chemically synthesized, or purified from a natural source.

In a further embodiment the presence of integrin alpha 10 subunit in a biological sample is detected in vivo by using an integrin alpha 10 subunit-specific antibody, or an integrin alpha 10 subunit binding peptide or protein, or an integrin alpha 10 subunit nucleic acid probe which binds to integrin alpha 10 subunit RNA or cDNA in a hybridizing reaction.

Typical methods for detection of cell surface antigens and polynucleotides in vivo are well known in the art include but are not limited to positron emission tomography, x-ray computed tomography (CT), magnetic resonance imaging (MRI) and functional magnetic resonance imaging (fMRI), ultrasound and single-photon emission computed tomography (SPECT). In particular cell surface antigens can be imaged in vivo using immunolabelling with a radioactive tracer bound to an antibody or other specifically binding protein.

Preferably the antibodies used for in vivo imaging are antibody fragments such as Fab fragments, and single chain antibodies due to their smaller size and absence of effector function.

Further steps of the methods may encompass comparing the amount of integrin alpha 10 subunit detected to a positive and/or negative control, thereby detecting the malignant neoplasm of the CNS. This can be done by setting up background levels of a staining in a particular experimental set up to be able to distinguish a positive staining from a negative, to assess that the method has performed accordingly as expected and that a positive staining is a true detection of said neoplasm.

Further, the positive control may comprise a cell line or tissue known to express integrin alpha 10 subunit. Examples of control samples include but are not limited to glioblastoma cell lines.

Further, the negative control may comprise a cell line or tissue known to not express integrin alpha 10 subunit. Examples of control samples include but are not limited to normal cells, tissues or cell lines from brain, such as a human brain.

IV. Markers Co-Expressing with Integrin Alpha 10 Subunit

Malignant tumour cells, also referred to as cancer cells, are the foundation of cancer as a disease. These cells initiate tumours and drive tumour progression forward, carrying the oncogenic and tumour suppressor mutations that define cancer as a genetic disease (Hanahan and Weinberg (2011) Cell 144(5):646-74)).

Specific characteristics for malignant tumour cells are that they invade neighbouring tissues, enter blood vessels, and metastasize to distant sites. In addition to malignant cells, the tumour microenvironment also includes nonmalignant cells (e.g. fibroblasts, myofibroblasts, endothelial cells, pericytes, and inflammatory cells) and secreted proteins that surround and support the growth of the tumour. Crosstalk between tumour cells and the microenvironment changes the composition of the microenvironment in one direction, and conversely, the microenvironment affects how tumour cells grow and spread (Ansel) and Vonderheide (2013) Ansell S M, Vonderheide R H (2013) Cellular composition of the tumour microenvironment. Am Soc Clin Oncol Educ Book).

Tumour microenvironment composition varies depending on the tumour site. The brain in particular, consists of numerous specialized cell types such as microglia, astrocytes, and brain endothelial cells. In addition to brain-resident cells, brain tumours have also been shown to be infiltrated by different populations of hematopoietic cells (Lorger (2012) Cancers 4:218-243).

Many different cell types are possible targets for treatment of cancer. For example blood vessels in the brain have been shown to be important for the expansion and maintenance of cancer stem cell populations in glioma, pericytes and their interaction with the tumour vasculature have been shown to be crucial for intracranial tumour growth in animal models, and inhibiting endothelial progenitor cell recruitment to tumours may also be of therapeutic value.

It is well accepted that blood vessels promote tumour growth by supplying the nutrition and oxygen to cancer cells. In addition, tumour cells use blood vessels to spread through the brain parenchyma by migrating along the abluminal vessel site between endothelial cells and astrocyte end feet processes. The maintenance of the cancer stem cell (CSC) population in primary brain tumours also depends on the presence of the so-called perivascular niche.

Cells of the monocyte lineage are categorised based on their maturation status, and their progeny include macrophages and dendritic cells. Differentiation of these cells is defined by a variety of cell surface markers such as CD11c, CD14, and CD68.

Monocytic cells are essential to the innate immune response, serving as a first line of resistance against pathogens while also activating adaptive immune responses. Depending on the type of stimulation, macrophages may undergo classical M1 activation (stimulated by lipopolysaccharide and IFN-γ) or, alternatively, M2 activation (stimulated by IL-4 and IL-13). The resulting M1 and M2 macrophages produce distinct cytokines and have different functional roles in the innate immune response. For example, M1 macrophages secrete IL-12 and promote TH1 cell development, whereas M2 macrophages produce IL-10 and facilitate the development of TH2 cells (Schmieder et al. (2012) Semin Cancer Biol. 22:289-297). M1 macrophages are recruited to early-stage tumours, infiltrating the tumour microenvironment in response to inflammatory signals. Subsequently, M1 macrophages then release pro-inflammatory cytokines and chemokines to promote the development and differentiation of T and NK cells. In later stages, macrophages differentiate into a subpopulation called tumour associated macrophages (TAMs). TAMs may polarize to M2 cells, releasing cytokines to encourage TH2 differentiation and recruitment. Furthermore, TAMs inhibit antitumour immunity by secreting suppressive cytokines, such as TGF-, leading to an increase in angiogenesis and the expression of growth factors involved in supporting tumour growth. Clinical observations suggest that an increase in the number or density of intratumoural macrophages correlates with both progression and prognosis in the majority of malignancies (Bingle et al. (2002) Bingle L, Brown N J, Lewis C E. (2002). The role of tumour-associated macrophages in tumour progression is described in Bingle et al (2002) J Pathol. 196:254-265.

Figure 8:
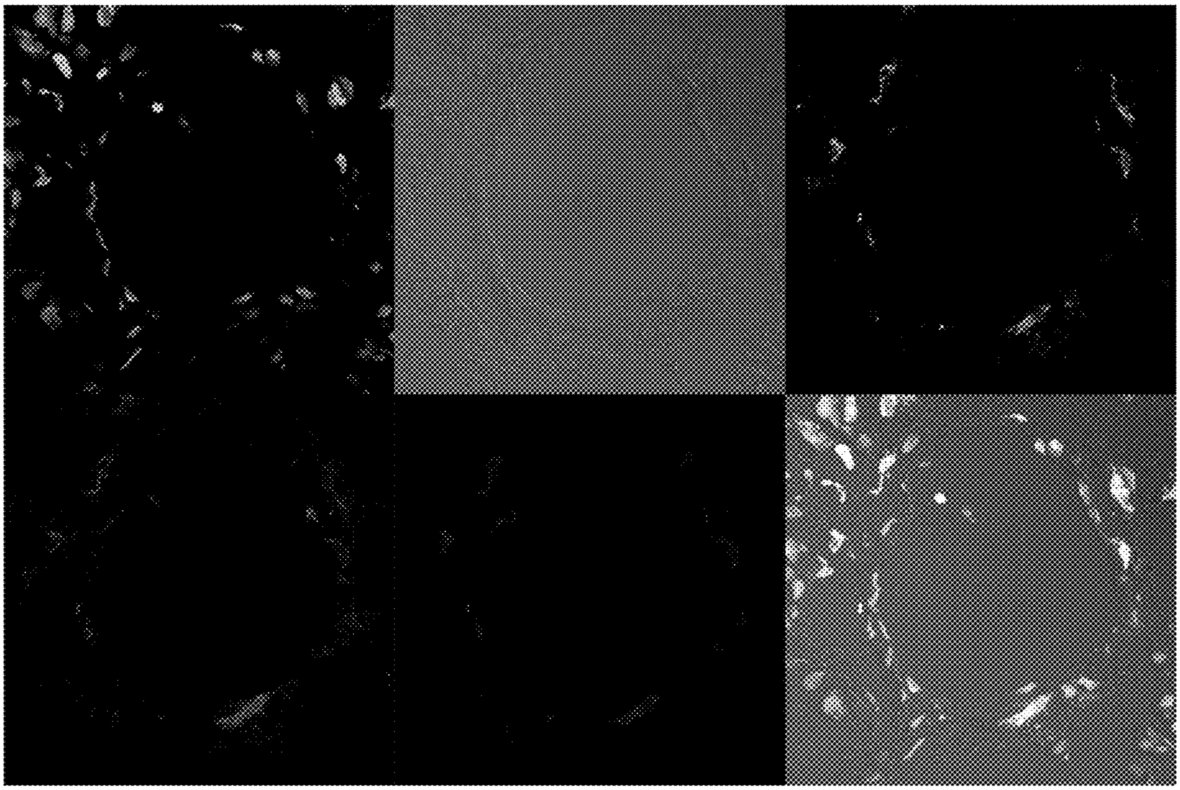
FIG. 8: Co-localisation of integrin α10 with CD163 and CD206 on cells in glioblastoma tissue.
Figure 9:
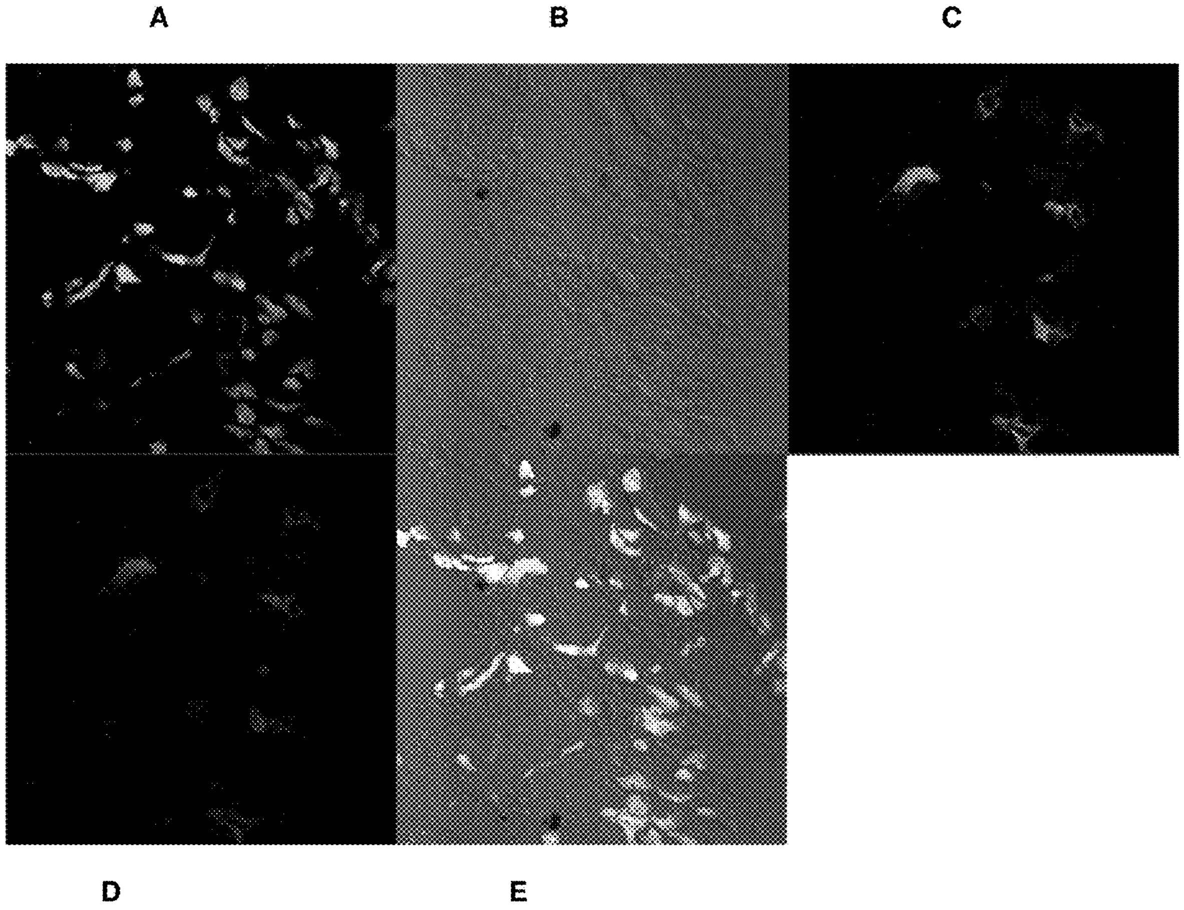
FIG. 9: Co-localisation of integrin α10 with EGFRvIII on cells in glioblastoma tissue.

As demonstrated in example 7 and FIGS. 8-9, the present inventors have found that a number of markers which to various degree co-express with integrin alpha 10 subunit. These markers include EGFRvIII, Nestin, PSA-NCAM, GFAP, PDGFRb (CD140b), PECAM-1 (CD31), CD45, CD68, CD163 and CD206. Based on these findings, the inventors have provided a multi-dimensional method for detecting and treating cells including malignant neoplasms of the central nervous system of a mammal.

Thus, in one aspect, the present invention concerns a method for detecting a malignant or tumour-associated mammalian cell, said method comprising analysing in an isolated sample, the presence or absence of:

a) a first antigen comprising an integrin alpha 10 subunit polypeptide;

and/or b) a first polynucleotide transcript which encodes an integrin alpha 10 subunit polypeptide or a fragment or variant thereof; and c) a second antigen comprising a polypeptide selected from the group consisting of EGFRvIII, Nestin, PSA-NCAM, GFAP, PDGFRb (CD140b), PECAM-1 (CD31), CD45, CD68, CD163 and CD206; and/or d) a second polynucleotide transcript which encodes a polypeptide or a fragment or variant thereof, wherein said polypeptide is selected from the group consisting of EGFRvIII, Nestin, PSA-NCAM, GFAP, PDGFRb (CD140b), PECAM-1 (CD31), CD45, CD68, CD163, and CD206;

wherein presence of the first antigen of a) and/or the first polynucleotide transcript of b); together with and the second antigen of c) and/or the second transcript of d), is indicative of that said mammalian cell is a malignant or a tumour-associated cell.

In one aspect, the present invention concerns a method for detecting a malignant or tumour-associated cell of a mammal, said method comprising the steps of:

a) administering to a subject a first molecular probe capable of binding specifically to an integrin alpha 10 subunit polypeptide; and/or to an integrin alpha 10 subunit polynucleotide transcript, said first probe being covalently bound to a first moiety capable of emitting photons; and b) administering to a subject a second molecular probe capable of binding specifically to a polypeptide selected from the group consisting of wherein said polypeptide is selected from the group consisting of EGFRvIII, Nestin, PSA-NCAM, GFAP, PDGFRb (CD140b), PECAM-1 (CD31), CD45, CD68, CD163, and CD206; and/or to a polynucleotide transcript encoding a polypeptide selected from the group consisting of EGFRvIII, Nestin, PSA-NCAM, GFAP, PDGFRb (CD140b), PECAM-1 (CD31), CD45, CD68, CD163, and CD206, said second probe being covalently bound to a second moiety capable of emitting photons;

c) detecting photons emitted from said first and said second moieties, thus forming an image of the central nervous system or part thereof, wherein localised emission of photons from said first and said second moiety is indicative of a malignant or tumour-associated cell of said mammal.

EGFRvIII

The epidermal growth factor receptor (EGFR) is overexpressed in a variety of human epithelial tumours, often as a consequence of gene amplification. Tumours with EGFR gene amplification frequently contain EGFR gene rearrangements, with the most common extracellular domain mutation being EGFRvIII. Aberrant EGFRvIII signaling has been shown to be important in driving tumour progression and often correlates with poor prognosis. It is clear that EGFRvIII is expressed in a considerable proportion of patients with glioblastoma multiforme (GBM). The presence of EGFRvIII in other tumour types has however remained controversial. (Gan et al (2013) FEBS J 280(21): 5350-5370). The present inventors have found that EGFRvIII co-expresses to a very high degree with integrin alpha 10 subunit in malignant cells. Thus in one embodiment of the present invention, detection of a cell which co-expresses an integrin alpha 10 subunit antigen and an EGFRvIII antigen, is indicative of that said cell is a malignant cell, such as a cell of a malignant neoplasm of the CNS, e.g. a cell of a glioma in a the mammal from which said sample derives. In another embodiment, detection of a cell which comprises a polynucleotide transcript encoding an integrin alpha 10 subunit polypeptide; and a polynucleotide transcript encoding an EGFRvIII polypeptide, is indicative of that said cell is a malignant cell, such as a cell of a malignant neoplasm of the CNS, e.g. a cell of a glioma in a the mammal from which said sample derives.

Nestin

Nestin is a type VI intermediate filament (IF) protein. These intermediate filament proteins are expressed mainly in neurons where they are implicated in the radial growth of the axon. Nestin has been the most extensively used marker to identify CNS stem cells within various areas of the developing nervous system and in cultured cells in vitro. The present inventors have found that nestin co-expresses with integrin alpha 10 subunit in some CNS cells. Thus in one embodiment of the present invention, detection of a cell which co-expresses an integrin alpha 10 subunit antigen and a nestin antigen, is indicative of that said cell is a malignant or tumour-associated cell, such as a cell of a malignant neoplasm of the CNS, e.g. a cell of a glioma, in a the mammal from which said sample derives. In another embodiment, detection of a cell which comprises a polynucleotide transcript encoding an integrin alpha 10 subunit polypeptide; and a polynucleotide transcript encoding a nestin polypeptide, is indicative of that said cell is a malignant or tumour-associated cell, such as a cell of a malignant neoplasm of the CNS, e.g. a cell of a glioma in a the mammal from which said sample derives.

PSA-NCAM

PolySialylated Neuronal Cell Adhesion Molecule (PSA-NCAM) is a marker of developing and migrating neurons and of synaptogenesis in the immature vertebrate nervous system. The present inventors have found that PSA-NCAM co-expresses with integrin alpha 10 subunit in malignant or tumour associated cells. Thus in one embodiment of the present invention, detection of a cell which co-expresses an integrin alpha 10 subunit antigen and a PSA-NCAM antigen, is indicative of that said cell is a malignant or tumour-associated cell, such as a cell of a malignant neoplasm of the CNS, e.g. a cell of a glioma, in a the mammal from which said sample derives.

In another embodiment, detection of a cell which comprises a polynucleotide transcript encoding an integrin alpha 10 subunit polypeptide; and a polynucleotide transcript encoding an PSA-NCAM polypeptide, is indicative of that said cell is a malignant or tumour-associated cell, such as a cell of a malignant neoplasm of the CNS, e.g. a cell of a glioma in a the mammal from which said sample derives.

GFAP

Glial Fibrillary Acidic Protein (GFAP) is an intermediate filament (IF) protein that is expressed by numerous cell types of the central nervous system (CNS) including astrocytes, and ependymal cells. GFAP is thought to help to maintain astrocyte mechanical strength, as well as the shape of cells but its exact function remains poorly understood, despite the number of studies using it as a cell marker. The present inventors have found that GFAP co-expresses with integrin alpha 10 subunit in malignant cells. Thus in one embodiment of the present invention, detection of a cell which co-expresses an integrin alpha 10 subunit antigen and a GFAP antigen, is indicative of that said cell is a malignant or tumour-associated cell, such as a cell of a malignant neoplasm of the CNS, e.g. a cell of a glioma, in a the mammal from which said sample derives. In another embodiment, detection of a cell which comprises a polynucleotide transcript encoding an integrin alpha 10 subunit polypeptide; and a polynucleotide transcript encoding an GFAP polypeptide, is indicative of that said cell is a malignant or tumour-associated cell, such as a cell of a malignant neoplasm of the CNS, e.g. a cell of a glioma in a the mammal from which said sample derives.

PDGFRb (CD140b)

Beta-type platelet-derived growth factor receptor is a protein that in humans is encoded by the PDGFRB gene. This gene encodes a cell surface tyrosine kinase receptor for members of the platelet-derived growth factor family. These growth factors are mitogens for cells of mesenchymal origin. The present inventors have found that PDGFRb/CD140b co-expresses with integrin alpha 10 subunit in malignant cells. Thus in one embodiment of the present invention, detection of a cell which co-expresses an integrin alpha 10 subunit antigen and a PDGFRb/CD140b antigen, is indicative of that said cell is a malignant or tumour associated cell, such as a cell of a malignant neoplasm of the CNS, e.g. a cell of a glioma, in the mammal from which said sample derives. In another embodiment, detection of a cell which comprises a polynucleotide transcript encoding an integrin alpha 10 subunit polypeptide; and a polynucleotide transcript encoding an PDGFRb/CD140b polypeptide, is indicative of that said cell is a malignant or tumour associated cell, such as a cell of a malignant neoplasm of the CNS, e.g. a cell of a glioma in a the mammal from which said sample derives.

PECAM-1 (CD31)

Platelet endothelial cell adhesion molecule (PECAM-1) also known as cluster of differentiation 31 (CD31) plays a key role in removing aged neutrophils from the human body. PECAM-1 is normally found on endothelial cells, platelets, macrophages and Kupffer cells, granulocytes, T/NK cells, lymphocytes, megakaryocytes, osteoclasts, neutrophils. CD31 is also expressed in certain tumours, including epithelioid hemangioendothelioma, epithelioid sarcoma-like hemangioendothelioma, other vascular tumours, histiocytic malignancies, and plasmacytomas. It is rarely found in some sarcomas, such as Kaposi's sarcoma, and carcinomas. The present inventors have found that PECAM-1 (CD31) co-expresses with integrin alpha 10 subunit in malignant cells. Thus in one embodiment of the present invention, detection of a cell which co-expresses an integrin alpha 10 subunit antigen and a PECAM-1 (CD31) antigen, is indicative of that said cell is a malignant or tumour associated cell, such as a cell of a malignant neoplasm of the CNS, e.g. a cell of a glioma, in a the mammal from which said sample derives. In another embodiment, detection of a cell which comprises a polynucleotide transcript encoding an integrin alpha 10 subunit polypeptide; and a polynucleotide transcript encoding an PECAM-1 (CD31) polypeptide, is indicative of that said cell is a malignant or tumour associated cell, such as a cell of a malignant neoplasm of the CNS, e.g. a cell of a glioma in a the mammal from which said sample derives.

CD45

CD45 also known as Protein tyrosine phosphatase, receptor type, C (PTPRC) is an enzyme that, in humans, is encoded by the PTPRC gene. CD45 is a type I transmembrane protein that in various forms is present on all differentiated hematopoietic cells, except erythrocytes and plasma cells that assists in the activation of those cells. CD45 is expressed in lymphomas, B-cell chronic lymphocytic leukemia, hairy cell leukemia, and acute nonlymphocytic leukemia. The present inventors have found that CD45 co-expresses to a high degree with integrin alpha 10 subunit in malignant cells. Thus in one embodiment of the present invention, detection of a cell which co-expresses an integrin alpha 10 subunit antigen and a CD45 antigen, is indicative of that said cell is a malignant or tumour associated cell, such as a cell of a malignant neoplasm of the CNS, e.g. a cell of a glioma, in a the mammal from which said sample derives.

In another embodiment, detection of a cell which comprises a polynucleotide transcript encoding an integrin alpha 10 subunit polypeptide; and a polynucleotide transcript encoding an CD45 polypeptide, is indicative of that said cell is a malignant or tumour associated cell, such as a cell of a malignant neoplasm of the CNS, e.g. a cell of a glioma in a the mammal from which said sample derives.

CD68

CD68 (Cluster of Differentiation 68) is a glycoprotein which binds to low density lipoprotein. CD68 is found in the cytoplasmic granules of a range of different blood cells and myocytes. It is considered as particularly useful as a marker for the various cells of the macrophage lineage, including monocytes, histiocytes, giant cells, Kupffer cells, and osteoclasts. Its presence in macrophages also makes it useful in diagnosing conditions related to proliferation or abnormality of these cells, such as malignant histiocytosis, histiocytic lymphoma, and Gaucher's disease. The present inventors have found that CD68 co-expresses to a very high degree with integrin alpha 10 subunit in malignant cells. Thus in one embodiment of the present invention, detection of a cell which co-expresses an integrin alpha 10 subunit antigen and a CD68 antigen, is indicative of that said cell is a malignant or tumour associated cell, such as a cell of a malignant neoplasm of the CNS, e.g. a cell of a glioma, in a the mammal from which said sample derives. In another embodiment, detection of a cell which comprises a polynucleotide transcript encoding an integrin alpha 10 subunit polypeptide; and a polynucleotide transcript encoding an CD68 polypeptide, is indicative of that said cell is a malignant or tumour associated cell, such as a cell of a malignant neoplasm of the CNS, e.g. a cell of a glioma in a the mammal from which said sample derives.

CD163

CD163 (Cluster of Differentiation 163) is a scavenger receptor for the hemoglobin-haptoglobin complex. It has also been shown to mark cells of monocyte/macrophage lineage. The present inventors have found that CD163 co-expresses with integrin alpha 10 subunit in malignant cells. Thus in one embodiment of the present invention, detection of a cell which co-expresses an integrin alpha 10 subunit antigen and a CD163 antigen, is indicative of that said cell is a malignant or tumour associated cell, such as a cell of a malignant neoplasm of the CNS, e.g. a cell of a glioma, in a the mammal from which said sample derives. In another embodiment, detection of a cell which comprises a polynucleotide transcript encoding an integrin alpha 10 subunit polypeptide; and a polynucleotide transcript encoding an CD163 polypeptide, is indicative of that said cell is a malignant or tumour associated cell, such as a cell of a malignant neoplasm of the CNS, e.g. a cell of a glioma in a the mammal from which said sample derives.

CD206

CD206 (Cluster of Differentiation 206) also referred to as the mannose receptor is primarily present on the surface of macrophages and immature dendritic cells, but is also expressed on the surface of skin cells such as human dermal fibroblasts and keratinocytes. The present inventors have found that CD206 co-expresses with integrin alpha 10 subunit in malignant cells. Thus in one embodiment of the present invention, detection of a cell which co-expresses an integrin alpha 10 subunit antigen and a CD206 antigen, is indicative of that said cell is a malignant or tumour associated cell, such as a cell of a malignant neoplasm of the CNS, e.g. a cell of a glioma, in a the mammal from which said sample derives. In another embodiment, detection of a cell which comprises a polynucleotide transcript encoding an integrin alpha 10 subunit polypeptide; and a polynucleotide transcript encoding an CD206 polypeptide, is indicative of that said cell is a malignant or tumour associated cell, such as a cell of a malignant neoplasm of the CNS, e.g. a cell of a glioma in a the mammal from which said sample derives.

Based on the data of the present invention, and literature evidence, the present inventors have provided a method for identifying cells expressing an integrin alpha 10 subunit polypeptide, and a further polypeptide selected from the group consisting of EGFRvIII, Nestin, PSA-NCAM, GFAP, PDGFRb (CD140b), PECAM-1 (CD31), CD45, CD68, CD163, and CD206. Depending on the expression pattern, the cells can be identified as indicated in table 1.

The samples analysed according to the present invention contain malignant cells or tumour-associated cells. In one embodiment the cells expressing integrin alpha 10 subunit are malignant cells. In one embodiment the cells expressing integrin alpha 10 subunit are tumour-associated cells. In one embodiment the malignant cells or tumour-associated cells comprise cells selected from the group consisting of glial cells; stem cells; progenitor cells; astrocytes; pericytes; endothelial cells; hematopoietic cells; and microglia.

The hematopoietic cells may e.g. be selected from the group consisting of hematopoietic stem cells, T-cells, B-cells, plasma cells, NK-cells, dendritic cells, macrophages and monocytes. In a particular embodiment the macrophage is a tumour-associated macrophage (TAM).

In one embodiment the cell is selected from the group consisting of EGFRvIII$^+$ cells, Nestin$^+$ cells, PSA-NCAM$^+$ cells, GFAP$^+$ cells, PDGFRb$^+$ cells (CD140b$^+$ cells), PECAM-1$^+$ cells (CD31$^+$ cells), CD45$^+$ cells, CD68$^+$ cells, CD163$^+$ cells and CD206$^+$ cells, or any combination thereof.

V. Samples

The sample may be any sample from or deriving from the CNS. Methods for obtaining tissue or blood samples are routine for the person of skill in the art. In certain embodiments the biological sample is a brain tissue sample or a spinal cord tissue sample. In further embodiments the biological sample is a brain tumour tissue sample or spinal cord tumour tissue sample. In further embodiments the biological sample is a blood sample.

Figure 5:
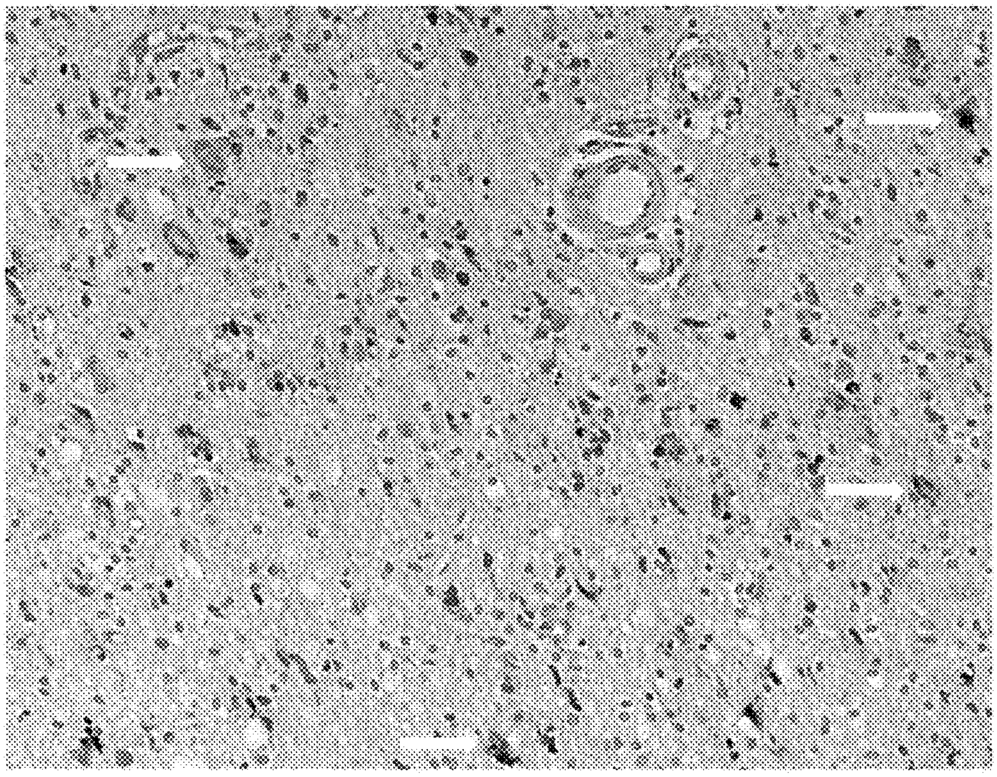
FIG. 5: Expression of Integrin α10 is differentially detected in different grades of glioma. By using an antibody directed against integrin α10 it was shown that integrin α10 is specifically expressed on cells in patient brain tumour tissue samples consisting of astrocytoma grade II (few cells; see arrows) (A), astrocytoma grade III (B), glioblastoma multiforme also known as astrocytoma grade IV (C), visualized by immunohistochemical staining. The expression of integrin α10 is increased with grades and is strongly expressed in astrocytoma grade III and IV. Positive staining of cells in blood vessels can be found in all grades of gliomas (D).
Figure 5:
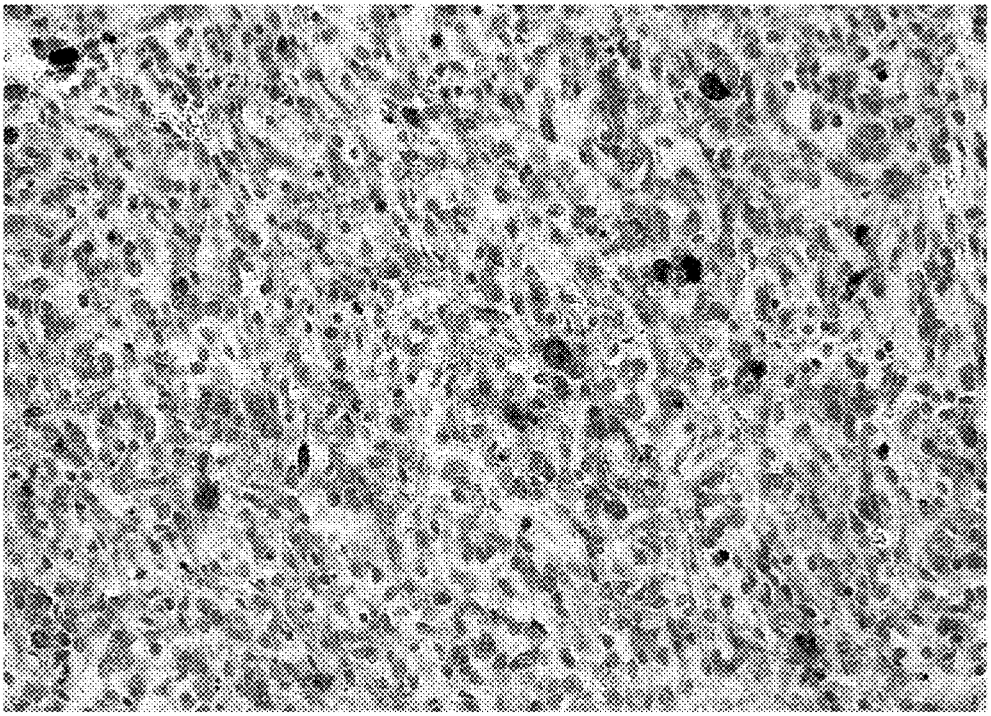

As demonstrated in example 4 and FIG. 5, it is also possible to detect integrin alpha 10 subunit in cells present in blood such as whole blood or blood plasma. Thus in one embodiment the detection or diagnosis of a malignant neoplasm of the CNS is conducted by taking a blood sample and analyzing the presence or absence of integrin alpha 10 subunit or a fragment thereof (e.g. a fragment comprising SEQ ID NO: 2 or 3) on or in cells present in said blood sample.

In further embodiments the biological sample is a subject, i.e. the test for integrin alpha 10 subunit expression is performed in vivo or in situ. After removal of a malignant neoplasm of the CNS from a subject by surgery, an integrin alpha 10 subunit-specific antibody, or an integrin alpha 10 subunit binding peptide or protein, or an integrin alpha 10 subunit nucleic acid probe may be used to detect residual cells from the tumour. This may be done by contacting the space where the brain tumour has been removed from, by applying the integrin alpha 10 subunit-specific antibody, or the integrin alpha 10 subunit binding peptide or protein, or the integrin alpha 10 subunit nucleic acid probe to the cavity appearing after the tumour removal. Thus the applied integrin alpha 10 subunit-specific antibody, or the integrin alpha 10 subunit binding peptide or protein, or the integrin alpha 10 subunit nucleic acid probe will detect any residual cells from the glioma tumour left in the cavity after removal of the tumour.

In further embodiments the integrin alpha 10 subunit-specific antibody, or the integrin alpha 10 subunit binding peptide or protein, or the integrin alpha 10 subunit nucleic acid probe may be applied to the cavity appearing after tumour removal by brushing or spraying.

A number of detection methods for detection of tissues or cells in vivo are known to those skilled in the art. Such imaging methods include positron emission tomography (PET), single photon emission computed tomography (SPECT), X-ray computed tomography (CT), magnetic resonance imaging (MRI), functional magnetic resonance imaging (fMR), and ultrasound.

A further aspect of the present invention is the use of an integrin alpha 10 subunit-specific antibody, or an integrin alpha 10 subunit binding peptide or protein, or an integrin alpha 10 subunit nucleic acid probe to detect a glioma in a biological sample in vitro, in situ or in vivo.

VI. Kits

Further aspects of the disclosure provides a kit for detecting a malignant neoplasm of the CNS such as a glioma, in a biological sample, the kit comprising a) an antibody specific for integrin alpha 10 subunit, a peptide binding to an integrin alpha 10 subunit antigen, a polynucleotide probe capable of hybridizing to an integrin alpha 10 subunit transcript; or
b) a pair of primers for amplification of an integrin alpha 10 subunit transcript; and
c) optionally, instructions for use.

Further, said kit may include positive and/or negative control samples, such as a cell line or tissue known to express or not express integrin alpha 10 subunit. Examples of control samples include but are not limited to glioblastoma cell lines, normal cells, tissues or cell lines from brain, such as a human brain. In further embodiments, the brain cells or cell lines are of adult origin.

In some embodiments, the kit includes instructional materials disclosing, for example, means of use of the anti-integrin alpha 10 subunit-specific antibody, or the peptide binding to an integrin alpha 10 subunit antigen, or the nucleic acid probe encoding integrin alpha 10 subunit or its compliment. The instructions may be written, in an electronic form, or may be visual.

In some embodiments the kit may also include additional components to facilitate the particular application for which the kit is designed. Thus, for example, the kit can include buffers and other reagents routinely used for the practice of the disclosed method. Such kits and appropriate contents are well known to those skilled in the art.

In certain embodiments the kit comprises further reagents, such as antibodies, for detection of one or more further markers known to be co-expressed or co-localised with integrin alpha 10 subunit with as described elsewhere herein.

VII. Detectable Moieties

The anti-integrin alpha 10 subunit antibodies of the present invention may comprise a detectable moiety, e.g. the antibody may be covalently bound to the detectable moiety.

In one embodiment the antibody is covalently bound to a detectable moiety selected from the group consisting of a fluorophore, an enzyme or a radioactive tracer or radioisotope. In one embodiment the detectable moiety is a radioactive tracer selected from a positron emitter and a gamma emitter. In one embodiment the radioisotope is selected from the group consisting of 99mTc, $^{111}$In, $^{67}$Ga, $^{68}$Ga, $^{72}$As, $^{89}$Zr, $^{123}$I and $^{201}$Tl. In one embodiment the antibody comprises a pair of detectable and cytotoxic radionuclides, such as $^{86}$Y/$^{90}$Y or $^{124}$I/$^{211}$At.

In one embodiment the radioisotope is capable of simultaneously acting in a multi-modal manner as a detectable moiety and also as a cytotoxic moiety.

In one embodiment the detectable moiety comprises or consists of a paramagnetic isotope, such as one selected from the group consisting of $^{157}$Gd, $^{55}$Mn, $^{162}$Dy, $^{52}$Cr and $^{56}$Fe. In one embodiment the detectable moiety is detectable by an imaging technique such as SPECT, PET, MRI, optical or ultrasound imaging.

In one embodiment the cytotoxic moiety and/or detectable moiety is joined to the antibody or antigen-binding fragment thereof indirectly, via a linking moiety. The linking moiety may for example be a chelator, such as a chelator selected from the group consisting of derivatives of 1,4,7,10-tetraazacyclododecane-1,4,7,10,tetraacetic acid (DOTA), deferoxamine (DFO), derivatives of diethylenetriaminepentaacetic avid (DTPA), derivatives of S-2-(4-Isothiocyanatobenzyl)-1,4,7-triazacyclononane-1,4,7-triacetic acid (NOTA) and derivatives of 1,4,8,11-tetraazacyclodocedan-1,4,8,11-tetraacetic acid (TETA).

Items

1. A composition for use in the treatment of a malignant neoplasm in the central nervous system, said composition comprising an antibody specifically binding to an integrin alpha 10 subunit.
2. The composition for use according to item 1, wherein the antibody is covalently bound to a cytotoxic moiety.
3. The composition for use according to any one of the preceding items, wherein the cytotoxic moiety is selected from a toxin, a chemotherapeutic agent and a radioactive agent.
4. The composition for use according to any one of the preceding items, wherein the toxin is a ribosome inactivating protein.
5. The composition for use according to any one of the preceding items, wherein the ribosome inactivating protein is selected from the group consisting of shiga and shiga-like toxins; type I ribosome inactivating proteins, such as trichosanthin and luffin; type II ribosome inactivating proteins, such as ricin, agglutinin and abrin; and saporin.
6. The composition for use according to any one of the preceding items, wherein the ribosome inactivating protein is saporin.
7. The composition for use according to any one of the preceding items, wherein the antibody is covalently bound to a biological response modifier.
8. The composition for use according to any one of the preceding items, wherein the biological response modifier is a cytokine, such as a lymphokine, or an interferon.
9. The composition for use according to any one of the preceding items, wherein the composition further comprises one or more chemotherapeutic agents.
10. The composition for use according to any one of the preceding items, wherein the composition further comprises at least one pharmaceutically acceptable diluent, carrier or excipient.
11. The composition for use according to any one of the preceding items, wherein the integrin alpha 10 subunit is a naturally occurring variant of integrin alpha 10 subunit, an isoform of integrin alpha 10 subunit or a splice variant of an integrin alpha 10 subunit.
12. The composition for use according to any of the preceding items, wherein the antibody is capable of inducing cell death and/or inhibiting the growth and/or proliferation of cells expressing an integrin alpha 10 subunit.
13. The composition for use according to any one of the preceding items, wherein the cells are malignant cells or tumour-associated cells.
14. The composition for use according to any one of the preceding items, wherein the malignant cells or tumour-associated cells comprise cells selected from the group consisting of glial cells; pericytes; endothelial cells; hematopoietic cells; microglia and stem cells.
15. The composition for use according to any one of the preceding items, wherein the hematopoietic cells are selected from the group consisting of hematopoietic stem cells, T-cells, B-cells, plasma cells, NK-cells, dendritic cells, macrophages and monocytes.

16. The composition for use according to any one of the preceding items, wherein the macrophage is a tumour-associated macrophage (TAM).
17. The composition for use according to any of the preceding items, wherein the malignant neoplasm in the central nervous system is associated with cells expressing integrin alpha 10 subunit.
18. The composition for use according to any one of the preceding items, wherein the integrin alpha 10 subunit is as part of an integrin alpha 10 beta 1 heterodimer.
19. A method of treatment of a malignant neoplasm in the central nervous system of a subject in need thereof, said method comprising administering to said subject a clinically effective amount of an antibody specifically binding to integrin alpha 10 subunit.
20. The method of treatment according to any one of the preceding items, wherein said treatment is prophylactic, ameliorative or curative.
21. The method of treatment according to any one of the preceding items, wherein said treatment is initiated upon detection of an integrin alpha 10 subunit in said subject.
22. A method for inducing cell death and/or inhibiting the growth and/or proliferation of cells associated with a malignant neoplasm in the central nervous system, wherein the cells express an integrin alpha 10 subunit.
23. An agent comprising or consisting of an antibody with specificity for an integrin alpha 10 subunit for use in detecting cells associated with a malignant neoplasm of the central nervous system of a mammal, wherein the cells express an integrin alpha 10 subunit.
24. A method for detecting a malignant neoplasm in the central nervous system of a mammal, said method comprising the steps of:
    a) administering to the mammal a molecular probe capable of binding specifically to an integrin alpha 10 subunit polypeptide; and/or to an integrin alpha 10 subunit polynucleotide transcript, said probe being covalently bound to a moiety capable of emitting photons,
    b) detecting photons emitted from said moiety and forming an image of the central nervous system or part thereof, wherein localised emission of photons from said moiety is indicative of a malignant neoplasm in the central nervous system of said mammal.

25. A method for detecting a malignant neoplasm in the central nervous system of a mammal, said method comprising analysing in an isolated sample, the presence or absence of:
    a) an antigen comprising an integrin alpha 10 subunit polypeptide; and/or
    b) a polynucleotide transcript which encodes an integrin alpha 10 subunit polypeptide or a fragment or variant thereof, wherein presence of the antigen of a), and/or the polynucleotide transcript of b) is indicative of a malignant neoplasm in the central nervous system of said mammal.

26. An in vitro diagnostic method to diagnose a malignant neoplasm in the central nervous system of a mammal, said method comprising the steps of:
    a) contacting an in vitro sample with a molecular probe capable of binding specifically to an integrin alpha 10 subunit polypeptide, or to an integrin alpha 10 subunit polynucleotide transcript, said probe being covalently bound to a moiety capable of emitting photons,
    b) detecting photons emitted from said moiety and forming an image of the sample, wherein localised emission of photons from said moiety is indicative of a malignant neoplasm in the central nervous system of said mammal.

27. An in vitro method for the detection of an integrin alpha 10 subunit in an isolated sample, said method comprising analysing in said isolated sample, the presence or absence of:
    a) an antigen comprising an integrin alpha 10 subunit polypeptide; and/or
    b) a polynucleotide transcript which encodes an integrin alpha 10 subunit polypeptide or a fragment or variant thereof,
    wherein presence of the antigen of a), and/or the polynucleotide transcript of b) is indicative of a malignant neoplasm in the central nervous system of said mammal.
28. Use of an anti-integrin alpha 10 subunit antibody capable of binding specifically to an integrin alpha 10 subunit polypeptide to detect a malignant neoplasm of the central nervous system in a biological sample in vitro, in situ or in vivo.
29. Use of an integrin alpha 10 subunit nucleic acid probe capable of binding specifically to an integrin alpha 10 subunit mRNA or cDNA in a hybridizing reaction to detect a malignant neoplasm of the central nervous system in a biological sample in vitro, in situ or in vivo.
30. Use of an integrin alpha 10 subunit nucleic acid probe compound in the preparation of a kit for diagnosing a malignant neoplasm of the central nervous system.
31. Use of an anti-integrin alpha 10 subunit-specific antibody, in the preparation of a kit for diagnosing a malignant neoplasm of the central nervous system.
32. Use of an integrin alpha 10 subunit nucleic acid probe compound for the manufacture of a diagnostic agent for diagnosing, monitoring or determining if a mammal has a malignant neoplasm of the central nervous system, wherein said diagnostic agent is manufactured to measure presence of an integrin alpha 10 subunit polynucleotide in a biological sample, wherein presence of said integrin alpha 10 subunit polynucleotide in said sample is indicative of a malignant neoplasm of the central nervous system of said mammal.
33. Use of an anti-integrin alpha 10 subunit-specific antibody for the manufacture of a diagnostic agent for diagnosing, monitoring or determining if a mammal has a malignant neoplasm of the central nervous system, wherein said diagnostic agent is manufactured to measure presence of an integrin alpha 10 subunit polypeptide in a sample, wherein presence of said integrin alpha 10 subunit polypeptide in said sample is indicative of a malignant neoplasm of the central nervous system of said mammal.
34. A method for detecting a malignant or tumour-associated mammalian cell, said method comprising analysing in an isolated sample, the presence or absence of:
    a) a first antigen comprising an integrin alpha 10 subunit polypeptide; and/or
    b) a first polynucleotide transcript which encodes an integrin alpha 10 subunit polypeptide or a fragment or variant thereof;
    and c) a second antigen comprising a polypeptide selected from the group consisting of EGFRvIII, Nestin, PSA-NCAM, GFAP, PDGFRb (CD140b), PECAM-1 (CD31), CD45, CD68, CD163 and CD206;

and/or d) a second polynucleotide transcript which encodes a polypeptide or a fragment or variant thereof, wherein said polypeptide is selected from the group consisting of EGFRvIII, Nestin, PSA-NCAM, GFAP, PDGFRb (CD140b), PECAM-1 (CD31), CD45, CD68, CD163, and CD206;

wherein presence of the first antigen of a) and/or the first polynucleotide transcript of b); together with the second antigen of c) and/or the second transcript of d), indicates that said mammalian cell is a malignant cell or a tumour-associated cell.

35. A method for detecting a malignant or tumour-associated cell of a mammal, said method comprising the steps of:

a) administering to a mammal a first molecular probe capable of binding specifically to an integrin alpha 10 subunit polypeptide; and/or to an integrin alpha 10 subunit polynucleotide transcript, said first probe being covalently bound to a first moiety capable of emitting photons;

and b) administering to a mammal a second molecular probe capable of binding specifically to a polypeptide selected from the group consisting of EGFRvIII, Nestin, PSA-NCAM, GFAP, PDGFRb (CD140b), PECAM-1 (CD31), CD45, CD68, CD163, and CD206; and/or to a polynucleotide transcript encoding a polypeptide selected from the group consisting of EGFRvIII, Nestin, PSA-NCAM, GFAP, PDGFRb (CD140b), PECAM-1 (CD31), CD45, CD68, CD163, and CD206, said second probe being covalently bound to a second moiety capable of emitting photons;

c) detecting photons emitted from said first and said second moieties, thus forming an image of the central nervous system or part thereof, wherein localised emission of photons from said first and said second moiety is indicative of a malignant or tumour-associated cell of said mammal.

36. The agent, method or use according to any one of the preceding items, wherein said sample comprises malignant cells or tumour-associated cells.

37. The agent, method or use according to any of the preceding items, wherein the malignant cells or tumour-associated cells comprise cells selected from the group consisting of glial cells; astrocytes; pericytes; endothelial cells; hematopoietic cells; microglia and stem cells.

38. The agent, method or use according to any one of the preceding items, wherein the hematopoietic cell is selected from the group consisting of hematopoietic stem cells, T-cells, B-cells, plasma cells, NK-cells, dendritic cells, macrophages and monocytes.

39. The agent, method or use according to any one of the preceding items, wherein the macrophage is a tumour-associated macrophage (TAM).

40. The agent, method or use according to any one of the preceding items wherein said cell is selected from the group consisting of $EGFRvIII^+$ cells, $Nestin^+$ cells, $PSA\text{-}NCAM^+$ cells, $GFAP^+$ cells, $PDGFRb^+$ cells ($CD140b^+$ cells), $PECAM\text{-}1^+$ cells ($CD31^+$ cells), $CD45^+$ cells, $CD68^+$ cells, $CD163^+$ cells and $CD206^+$ cells, or any combination thereof.

41. The agent, method or use according to any one of the preceding items wherein said cell is an integrin alpha 10 $subunit^+$ and $EGFRvIII^+$ cell.

42. The agent, method or use according to any one of the preceding items wherein said cell is an integrin alpha 10 $subunit^+$ and $Nestin^+$ cell.

43. The agent, method or use according to any one of the preceding items wherein said cell is an integrin alpha 10 $subunit^+$ and $PSA\text{-}NCAM^+$ cell.

44. The agent, method or use according to any one of the preceding items wherein said cell is an integrin alpha 10 $subunit^+$ and $GFAP^+$ cell.

45. The agent, method or use according to any one of the preceding items wherein said cell is an integrin alpha 10 $subunit^+$ and $PDGFRb^+$ cell ($CD140b^+$ cell).

46. The agent, method or use according to any one of the preceding items wherein said cell is an integrin alpha 10 $subunit^+$ and $PECAM\text{-}1^+$ cell ($CD31^+$ cell).

47. The agent, method or use according to any one of the preceding items wherein said cell is an integrin alpha 10 $subunit^+$ and $CD45^+$ cell.

48. The agent, method or use according to any one of the preceding items wherein said cell is an integrin alpha 10 $subunit^+$ and $CD68^+$ cell.

49. The agent, method or use according to any one of the preceding items wherein said cell is an integrin alpha 10 $subunit^+$ and $CD163^+$ cell.

50. The agent, method or use according to any one of the preceding items wherein said cell is an integrin alpha 10 $subunit^+$ and $CD206^+$ cell.

51. The agent, method or use according to any one of the preceding items, further comprising detecting at least one:

a) an antigen comprising a polypeptide selected from the group consisting of EGFRvIII, Nestin, PSA-NCAM, GFAP, PDGFRb (CD140b), PECAM-1 (CD31), CD45, CD68, CD163 and CD206; and/or b) a polynucleotide transcript which encodes a polypeptide or a fragment or variant thereof, wherein said polypeptide is selected from the group consisting of EGFRvIII, Nestin, PSA-NCAM, GFAP, PDGFRb (CD140b), PECAM-1 (CD31), CD45, CD68, CD163, and CD206.

52. The composition for use, agent, method or use according to any one of the preceding items wherein the malignant neoplasm is selected from the groups consisting of:

a) Tumours of neuroepithelial tissue selected from i) Astrocytic tumours selected from Pilocytic astrocytoma (ICD-O 9421/1, WHO grade I), Pilomyxoid astrocytoma (ICD-O 9425/3, WHO grade II), Subependymal giant cell astrocytoma (ICD-O 9384/1, WHO grade I), Pleomorphic xanthoastrocytoma (ICD-O 9424/3, WHO grade II), Diffuse astrocytoma (ICD-O 9400/3, WHO grade II), Anaplastic astrocytoma (ICD-O 9401/3, WHO grade III), Glioblastoma (ICD-O 9440/3, WHO grade IV), Giant cell glioblastoma (ICD-O 9441/3, WHO grade IV), Gliosarcoma (ICD-O 9442/3, WHO grade IV), Gliomatosis cerebri (ICD-O 9381/3, WHO grade III), and ii) Oligodendroglial tumours selected from Oligodendroglioma (ICD-O 9450/3, WHO grade II) and Anaplastic iii) Oligoastrocytic tumours selected from Oligoastrocytoma (ICD-O 9382/3, WHO grade II) and Anaplastic oligoastrocytoma (ICD-O 9382/3, WHO grade III), and iv) Ependymal tumours selected from Subependymoma (ICD-O 9383/1, WHO grade I), Myxopapillary ependymoma (ICD-O 9394/1, WHO grade I), Ependymoma (ICD-O 9391/3, WHO grade II), Anaplastic ependymoma (ICD-O 9392/3, WHO grade III), and v) Choroid plexus tumours selected from Choroid plexus papilloma (ICD-O 9390/0, WHO grade I), Atypical choroid plexus papilloma (ICD-O 9390/1, WHO grade II), and Choroid plexus carcinoma (ICD-O 9390/3, WHO grade III), and vi) Other neuroepithelial tumours selected from Astroblastoma (ICD-O 9430/3, WHO grade I), Chordoid glioma of the third ventricle (ICD-O 9444/1, WHO grade II), and Angiocentric glioma (ICD-O 9431/1, WHO grade I) and, vii) Neuronal and mixed neuronal-glial tumours selected from Dysplastic gangliocytoma of cerebellum (Lhermitte-Duclos) (ICD-O 9493/0), Desmoplastic infantile astrocytoma/ganglioglioma (ICD-O 9412/1, WHO grade I), Dysembryoplastic neuroepithelial tumour (ICD-O 9413/0, WHO grade I), Gangliocytoma (ICD-O 9492/0, WHO grade I), Ganglioglioma (ICD-O 9505/1, WHO grade I), Anaplastic ganglioglioma (ICD-O 9505/3, WHO grade III), Central neurocytoma (ICD-O 9506/1, WHO grade II), Extraventricular neurocytoma (ICD-O 9506/1, WHO grade II), Cerebellar liponeurocytoma (ICD-O 9506/1, WHO grade II), Papillary glioneuronal tumour (ICD-O 9509/1, WHO grade I), Rosette-forming glioneuronal tumour of the fourth ventricle (ICD-O 9509/1, WHO grade I), and Paraganglioma (ICD-O 8680/1, WHO grade I), and viii) Tumours of the pineal region selected from Pineocytoma (ICD-O 9361/1, WHO grade I), Pineal parenchymal tumour of intermediate differentiation (ICD-O 9362/3, WHO grade II, III), Pineoblastoma (ICD-O 9362/3, WHO grade IV), and Papillary tumours of the pineal region (ICD-O 9395/3, WHO grade II, III), and ix) Embryonal tumours selected from Medulloblastoma (ICD-O 9470/3, WHO grade IV), Medulloblastoma with extensive nodularity (ICD-O 9471/3, WHO grade IV), Anaplastic medulloblastoma (ICD-O 9474/3, WHO grade IV), CNS Primitive neuroectodermal tumour (ICD-O 9473/3, WHO grade IV), CNS Neuroblastoma (ICD-O 9500/3, WHO grade IV), and Atypical teratoid/rhabdoid tumour (ICD-O 9508/3, WHO grade IV), and b) Tumours of cranial and paraspinal nerves selected from i) Schwannoma (ICD-O 9560/0, WHO grade I)

ii) Neurofibroma (ICD-O 9540/0, WHO grade I), iii) Perineurioma (ICD-O 9571/0, 9571/3, WHO grade I, II, III), and iv) Malignant peripheral nerve sheath tumour (MPNST) (ICD-O 9540/3, WHO grade II, III, IV), and c) Tumours of the meninges selected from i) Tumours of meningothelial cells, selected from Meningioma (ICD-O 9530/0, WHO grade I), Atypical meningioma (ICD-O 9539/1, WHO grade II), Anaplastic meningioma (ICD-O 9530/3, WHO grade III), and ii) Mesenchymal tumours selected from Lipoma (ICD-O 8850/0), Angiolipoma (ICD-O 8861/0), Hibernoma (ICD-O 8880/0), Liposarcoma (ICD-O 8850/3), Solitary fibrous tumour (ICD-O 8815/0), Fibrosarcoma (ICD-O 8810/3), Malignant fibrous histiocytoma (ICD-O 8830/3), Leiomyoma (ICD-O 8890/0), Leiomyosarcoma (ICD-O 8890/3), Rhabdomyoma (ICD-O 8900/0), Rhabdomyosarcoma (ICD-O 8900/3), Osteoma (ICD-O 9180/0), Osteosarcoma (ICD-O 9180/3), Osteo-chondroma (ICD-O 9210/0), Haemangioma (ICD-O 9120/0), Epithelioid hemangioendothelioma (ICD-O 9133/1), Haemangiopericytoma (ICD-O 9150/1, WHO grade II), Anaplastic haemangiopericytoma (ICD-O 9150/3, WHO grade III), and Angiosarcoma (ICD-O 9120/3) 3.2.22 Kaposi Sarcoma (ICD-O 9140/3), Ewing Sarcoma—PNET (ICD-O 9364/3), and iii) Primary melanocytic lesions selected from Diffuse melanocytosis (ICD-O 8728/0), Melanocytoma (ICD-O 8728/1) Malignant melanoma (ICD-O 8720/3), Meningeal melanomatosis (ICD-O 8728/3), and iv) Other neoplasms related to the meninges such as Haem-angioblastoma (ICD-O 9161/1, WHO grade I), and d) Tumours of the haematopoietic system selected from i) Malignant Lymphomas (ICD-O 9590/3)4.2 Plasmocytoma (ICD-O 9731/3), and ii) Granulocytic sarcoma (ICD-O 9930/3), and e) Tumours of the sellar region selected from i) Craniopharyngioma (ICD-O 9350/1, WHO grade I)

ii) Granular cell tumour (ICD-O 9582/0, WHO grade I)

iii) Pituicytoma (ICD-O 9432/1, WHO grade I), and iv) Spindle cell oncocytoma of the adenohypophysis (ICD-O 8991/0, WHO grade I).

53. The composition for use, agent, method or use according to any one of the preceding items wherein the malignant neoplasm is selected from the groups consisting of:

a) Tumours of neuroepithelial tissue selected from i) Astrocytic tumours selected from Pilocytic astrocytoma (ICD-O 9421/1, WHO grade I), Pilomyxoid astrocytoma (ICD-O 9425/3, WHO grade II), Subependymal giant cell astrocytoma (ICD-O 9384/1, WHO grade I), Pleomorphic xanthoastrocytoma (ICD-O 9424/3, WHO grade II), Diffuse astrocytoma (ICD-O 9400/3, WHO grade II), Anaplastic astrocytoma (ICD-O 9401/3, WHO grade III), Glioblastoma (ICD-O 9440/3, WHO grade IV), Giant cell glioblastoma (ICD-O 9441/3, WHO grade IV), Gliosarcoma (ICD-O 9442/3, WHO grade IV), Gliomatosis cerebri (ICD-O 9381/3, WHO grade III), and ii) Oligodendroglial tumours selected from Oligodendroglioma (ICD-O 9450/3, WHO grade II) and Anaplastic oligodendroglioma (ICD-O 9451/3, WHO grade III), and iii) Oligoastrocytic tumours selected from Oligoastrocytoma (ICD-O 9382/3, WHO grade II) and Anaplastic oligoastrocytoma (ICD-O 9382/3, WHO grade III), and iv) Ependymal tumours selected from Subependymoma (ICD-O 9383/1, WHO grade I), Myxopapillary ependymoma (ICD-O 9394/1, WHO grade I), Ependymoma (ICD-O 9391/3, WHO grade II), Anaplastic ependymoma (ICD-O 9392/3, WHO grade III), and v) Choroid plexus tumours selected from Choroid plexus papilloma (ICD-O 9390/0, WHO grade I), Atypical choroid plexus papilloma (ICD-O 9390/1, WHO grade II), and Choroid plexus carcinoma (ICD-O 9390/3, WHO grade III), and vi) Other neuroepithelial tumours selected from Astroblastoma (ICD-O 9430/3, WHO grade I), Chordoid glioma of the third ventricle (ICD-O 9444/1, WHO grade II), and Angiocentric glioma (ICD-O 9431/1, WHO grade I) and, vii) Neuronal and mixed neuronal-glial tumours selected from Dysplastic gangliocytoma of cerebellum (Lhermitte-Duclos) (ICD-O 9493/0), Desmoplastic infantile astrocytoma/ganglioglioma (ICD-O 9412/1, WHO grade I), Dysembryoplastic neuroepithelial tumour (ICD-O 9413/0, WHO grade I), Gangliocytoma (ICD-O 9492/0, WHO grade I), Ganglioglioma (ICD-O 9505/1, WHO grade I), Anaplastic ganglioglioma (ICD-O 9505/3, WHO grade III), Central neurocytoma (ICD-O 9506/1, WHO grade II), Extraventricular neurocytoma (ICD-O 9506/1, WHO grade II), Cerebellar liponeurocytoma (ICD-O 9506/1, WHO grade II), Papillary glioneuronal tumour (ICD-O 9509/1, WHO grade I), Rosette-forming glioneuronal tumour of the fourth ventricle (ICD-O 9509/1, WHO grade I), and Paraganglioma (ICD-O 8680/1, WHO grade I), and viii) Tumours of the pineal region selected from Pineocytoma (ICD-O 9361/1, WHO grade I), Pineal parenchymal tumour of intermediate differentiation (ICD-O 9362/3, WHO grade II, III), Pineoblastoma (ICD-O 9362/3, WHO grade IV), and Papillary tumours of the pineal region (ICD-O 9395/3, WHO grade II, III), and ix) Embryonal tumours selected from Medulloblastoma (ICD-O 9470/3, WHO grade IV), Medulloblastoma with extensive nodularity (ICD-O 9471/3, WHO grade IV), Anaplastic medulloblastoma (ICD-O 9474/3, WHO grade IV), CNS Primitive neuroectodermal tumour (ICD-O 9473/3, WHO grade IV), CNS Neuroblastoma (ICD-O 9500/3, WHO grade IV), and Atypical teratoid/rhabdoid tumour (ICD-O 9508/3, WHO grade IV), and b) Tumours of cranial and paraspinal nerves selected from i) Schwannoma (ICD-O 9560/0, WHO grade I)

ii) Neurofibroma (ICD-O 9540/0, WHO grade I), iii) Perineurioma (ICD-O 9571/0, 9571/3, WHO grade I, II, III), and iv) Malignant peripheral nerve sheath tumour (MPNST) (ICD-O 9540/3, WHO grade II, III, IV), and c) Tumours of the meninges selected from i) Tumours of meningothelial cells, selected from Meningioma (ICD-O 9530/0, WHO grade I), Atypical meningioma (ICD-O 9539/1, WHO grade II), Anaplastic meningioma (ICD-O 9530/3, WHO grade III), and ii) Mesenchymal tumours selected from Lipoma (ICD-O 8850/0), Angiolipoma (ICD-O 8861/0), Hibernoma (ICD-O 8880/0), Liposarcoma (ICD-O 8850/3), Solitary fibrous tumour (ICD-O 8815/0), Fibrosarcoma (ICD-O 8810/3), Malignant fibrous histiocytoma (ICD-O 8830/3), Leiomyoma (ICD-O 8890/0), Leiomyosarcoma (ICD-O 8890/3), Rhabdomyoma (ICD-O 8900/0), Rhabdomyosarcoma (ICD-O 8900/3), Chondroma (ICD-O 9220/0), Chondrosarcoma (ICD-O 9220/3), Osteoma (ICD-O 9180/0), Osteosarcoma (ICD-O 9180/3), Osteo-chondroma (ICD-O 9210/0), Haemangioma (ICD-O 9120/0), Epithelioid hemangioendothelioma (ICD-O 9133/1), Haemangiopericytoma (ICD-O 9150/1, WHO grade II), Anaplastic haemangiopericytoma (ICD-O 9150/3, WHO grade III), and Angiosarcoma (ICD-O 9120/3)3.2.22 Kaposi Sarcoma (ICD-O 9140/3), Ewing Sarcoma—PNET (ICD-O 9364/3), and iii) Primary melanocytic lesions selected from Diffuse melanocytosis (ICD-O 8728/0), Melanocytoma (ICD-O 8728/1) Malignant melanoma (ICD-O 8720/3), Meningeal melanomatosis (ICD-O 8728/3), and iv) Other neoplasms related to the meninges such as Haem-angioblastoma (ICD-O 9161/1, WHO grade I).

54. The composition for use, agent, method or use according to any one of the preceding items wherein the malignant neoplasm is selected from the groups consisting of:

a) Tumours of neuroepithelial tissue selected from:

i) Astrocytic tumours selected from:

Pilocytic astrocytoma (ICD-O 9421/1, WHO grade I), Pilomyxoid astrocytoma (ICD-O 9425/3, WHO grade II), Subependymal giant cell astrocytoma (ICD-O 9384/1, WHO grade I), Pleomorphic xanthoastrocytoma (ICD-O 9424/3, WHO grade II), Diffuse astrocytoma (ICD-O 9400/3, WHO grade II), Anaplastic astrocytoma (ICD-O 9401/3, WHO grade III), Glioblastoma (ICD-O 9440/3, WHO grade IV), Giant cell glioblastoma (ICD-O 9441/3, WHO grade IV), Gliosarcoma (ICD-O 9442/3, WHO grade IV), Gliomatosis cerebri (ICD-O 9381/3, WHO grade III), and ii) Embryonal tumours selected from:

Medulloblastoma (ICD-O 9470/3, WHO grade IV), Medulloblastoma with extensive nodularity (ICD-O 9471/3, WHO grade IV), Anaplastic medulloblastoma (ICD-O 9474/3, WHO grade IV), CNS Primitive neuroectodermal tumour (ICD-O 9473/3, WHO grade IV), CNS Neuroblastoma (ICD-O 9500/3, WHO grade IV), and Atypical teratoid/rhabdoid tumour (ICD-O 9508/3, WHO grade IV), and b) Tumours of the meninges selected from:

i) Tumours of meningothelial cells, selected from Meningioma (ICD-O 9530/0, WHO grade I), Atypical meningioma (ICD-O 9539/1, WHO grade II), Anaplastic meningioma (ICD-O 9530/3, WHO grade III), and ii) Mesenchymal tumours selected from Lipoma (ICD-O 8850/0), Angiolipoma (ICD-O 8861/0), Hibernoma (ICD-O 8880/0), Liposarcoma (ICD-O 8850/3), Solitary fibrous tumour (ICD-O 8815/0), Fibrosarcoma (ICD-O 8810/3), Malignant fibrous histiocytoma (ICD-O 8830/3), Leiomyoma (ICD-O 8890/0), Leiomyosarcoma (ICD-O 8890/3), Rhabdomyoma (ICD-O 8900/0), Rhabdomyosarcoma (ICD-O 8900/3), Chondroma (ICD-O 9220/0), Chondrosarcoma (ICD-O 9220/3), Osteoma (ICD-O 9180/0), Osteosarcoma (ICD-O 9180/3), Osteo-chondroma (ICD-O 9210/0), Haemangioma (ICD-O 9120/0), Epithelioid 9150/1, WHO grade II), Anaplastic haemangiopericytoma (ICD-O 9150/3, WHO grade III), and Angiosarcoma (ICD-O 9120/3)3.2.22 Kaposi Sarcoma (ICD-O 9140/3), Ewing Sarcoma—PNET (ICD-O 9364/3), and iii) Primary melanocytic lesions selected from Diffuse melanocytosis (ICD-O 8728/0), Melanocytoma (ICD-O 8728/1) Malignant melanoma (ICD-O 8720/3), Meningeal melanomatosis (ICD-O 8728/3), and iv) Other neoplasms related to the meninges such as Haem-angioblastoma (ICD-O 9161/1, WHO grade I).

55. The composition for use, agent, method or use according to any one of the preceding items, wherein the malignant neoplasm is a glioma.
56. The composition for use, agent, method or use according to any one of the preceding items, wherein the malignant neoplasm is a grade II, III or IV glioma.
57. The composition for use, agent, method or use according to any one of the preceding items, wherein the malignant neoplasm is an astrocytoma.
58. The composition for use, agent, method or use according to any one of the preceding items, wherein the malignant neoplasm is a glioblastoma.
59. The composition for use, agent, method or use according to any one of the preceding items wherein the malignant neoplasm of the brain is selected from the group consisting of glioblastomas, medulloblastomas, neuroblastomas, astrocytomas, anaplastic astrocytomas, hemangiopericytomas of the brain, meningiomas, angiomatous hemangiomas, atypical meningiomas, fibroblastic meningiomas, meningiothelial meningiomas, secretory meningiomas, oligoastrocytomas, anaplastic oligoastrocytomas, oligodendrogliomas, and anaplastic oligodendrogliomas.
60. The composition for use, agent, method or use according to any one of the preceding items wherein the glioblastoma tumours are selected from the group consisting of Astrocytic tumours, Oligodendroglial tumours, Ependymal cell tumours, Mixed gliomas, Neuroepithelial tumours of uncertain origin, Tumours of the choroid plexus, Neuronal and mixed neuronal-glial tumours, Pineal Parenchyma Tumours and Tumours with neuroblastic or glioblastic elements (embryonal tumours), ependymomas, astrocytomas, oligodendrogliomas, oligoastrocytomas, neuroepithelal tumours, and neuronal and mixed neuronal-glial tumours.
61. The composition for use, agent, method or use according to any one of the preceding items, wherein said sample is a brain tissue or spinal cord tissue sample.
62. The composition for use, agent, method or use according to any one of the preceding items, wherein said sample is a brain tumour tissue sample.
63. The composition for use, agent, method or use according to any one of the preceding items, wherein said sample is a blood sample.
64. The composition for use, agent, method or use according to any one of the preceding items, wherein the detection or diagnosis is based on cells present in a blood sample such as a whole blood sample or a blood plasma sample.
65. The composition for use, agent, method or use according to any one of the preceding items, wherein said method or use is carried out by using one or more antibodies specific for an integrin alpha 10 subunit.
66. The composition for use, agent, method or use according to any one of the preceding items, wherein the antigen is an isoform, a splice variant or a naturally occurring variant of an integrin alpha 10 subunit.
67. The composition for use, agent, method or use according to any one of the preceding items, wherein the antigen comprises the integrin alpha 10 subunit (SEQ ID NO: 1).
68. The composition for use, agent, method or use according to any one of the preceding items, wherein the antigen comprises the extracellular domain of an integrin alpha 10 subunit (SEQ ID NO: 2).
69. The composition for use, agent, method or use according to any one of the preceding items, wherein the antigen comprises the I-domain of integrin alpha 10 subunit (SEQ ID NO: 3).
70. The composition for use, agent, method or use according to any one of the preceding items, wherein the antibody is selected from the group consisting of a monoclonal antibody, a polyclonal antibody, an antibody fragment or a single chain antibody.
71. The composition for use, agent, method or use according to any one of the preceding items, wherein said antibody is a monoclonal antibody.
72. The composition for use, agent, method or use according to any one of the preceding items, wherein said antibody is a polyclonal antibody.
73. The composition for use, agent, method or use according to any one of the preceding items, wherein the antibody is a non-human antibody, a chimeric antibody, a bispecific antibody, a humanised antibody or a human antibody.
74. The composition for use, agent, method or use according to any one of the preceding items, wherein the antibody specifically binds to SEQ ID NO: 1 (integrin alpha10 subunit).
75. The composition for use, agent, method or use according to any one of the preceding items, wherein the antibody specifically binds to SEQ ID NO: 2 (the extracellular domain of integrin alpha10).
76. The composition for use, agent, method or use according to any one of the preceding items, wherein the antibody specifically binds to SEQ ID NO: 3 (the extracellular I-domain of integrin alpha10).
77. The composition for use, agent, method or use according to any one of the preceding items, wherein at least one antibody is covalently bound to a detectable moiety.
78. The composition for use, agent, method or use according to any one of the preceding items, wherein at least one antibody is covalently bound to a detectable moiety selected from the group consisting of a fluorophore, an enzyme or a radioactive tracer or radioisotope.

79. The composition for use, agent, method or use according to any one of the preceding items, wherein said antibody is linked to a radioactive tracer selected from a positron emitter, or a gamma emitter.

80. The composition for use, agent, method or use according to any one of the preceding items, wherein the radioisotope is selected from the group consisting of $^{99m}$Tc, $^{111}$In, $^{67}$Ga, $^{68}$Ga, $^{72}$As, $^{89}$Zr, $^{123}$I and $^{201}$Tl.

81. The composition for use, agent, method or use according to any one of the preceding items, wherein the antibody comprises a pair of detectable and cytotoxic radionuclides, such as $^{86}$Y/$^{90}$Y or $^{124}$I/$^{211}$At.

82. The composition for use, agent, method or use according to any one of the preceding items, wherein the radioisotope is capable of simultaneously acting in a multi-modal manner as a detectable moiety and also as a cytotoxic moiety.

83. The composition for use, agent, method or use according to any one of the preceding items, wherein the detectable moiety comprises or consists of a paramagnetic isotope.

84. The composition for use, agent, method or use according to any one of the preceding items, wherein the paramagnetic isotope is selected from the group consisting of $^{157}$Gd, $^{55}$Mn, $^{162}$Dy, $^{52}$Cr and $^{56}$Fe.

85. The composition for use, agent, method or use according to any one of the preceding items, wherein the detectable moiety is detectable by an imaging technique such as SPECT, PET, MRI, optical or ultrasound imaging.

86. The composition for use, agent, method or use according to any one of the preceding items, wherein the cytotoxic moiety and/or detectable moiety is joined to the antibody or antigen-binding fragment thereof indirectly, via a linking moiety.

87. The composition for use, agent, method or use according to item 86 wherein the linking moiety is a chelator.

88. The composition for use, agent, method or use according to any one of the preceding items, wherein the chelator is selected from the group consisting of derivatives of 1,4,7,10-tetraazacyclododecane-1,4,7,10,tetraacetic acid (DOTA), deferoxamine (DFO), derivatives of diethylenetriaminepentaacetic avid (DTPA), derivatives of S-2-(4-Isothiocyanatobenzyl)-1,4,7-triazacyclononane-1,4,7-triacetic acid (NOTA) and derivatives of 1,4,8,11-tetraazacyclodocedan-1,4,8,11-tetraacetic acid (TETA).

89. The composition for use, composition for use, agent, method or use according to any one of the preceding items, wherein the antibody has an isotype selected from the group consisting of IgA, IgD, IgG and IgM.

90. The composition for use, agent, method or use according to any one of the preceding items, wherein the antibody is an IgG isotype, such as an IgG isotype selected from the group consisting of IgG1, IgG2, IgG3, and IgG4.

91. The composition for use, agent, method or use according to any one of the preceding items, wherein the antibody fragment is selected from the group consisting of a Fab-fragment, a Fab' fragment, a $F(ab')_2$ fragment and an Fv fragment, such as a single-chain variable fragment (scFv) and a single-domain antibody.

92. The composition for use, agent, method or use according to any one of the preceding items, wherein said antibody specific for integrin alpha 10 subunit is:

a) a monoclonal antibody, produced by the hybridoma cell line deposited at the Deutsche Sammlung von Microorganismen und Zellkulturen GmbH under the accession number DSM ACC2583; or b) an antibody which competes for binding to the same epitope as the epitope bound by the monoclonal antibody produced by the hybridoma deposited at the Deutsche Sammlung von Microorganismen und Zellkulturen GmbH under the accession number DSM ACC2583; or c) a fragment of a) or b), wherein said fragment is capable of binding specifically to the extracellular I-domain of the integrin alpha 10 subunit chain.

93. The composition for use, agent, method or use according to any one of the preceding items, wherein the antigen is detected by detecting binding of a peptide capable of specifically binding to an integrin alpha 10 subunit antigen.

94. The composition for use, agent, method or use according to any one of the preceding items, wherein said detection is conducted using flow cytometry such as Fluorescence-Activated Cell Sorting (FACS).

95. The composition for use, agent, method or use according to any one of the preceding items, wherein said method is carried out by using one or more integrin alpha 10 subunit specific polynucleotide probes linked to a moiety capable of emitting photons.

96. The composition for use, agent, method or use according to any one of the preceding items, wherein the polynucleotide transcript is detected by PCR, preferably Q-PCR.

97. The composition for use, agent, method or use according to any one of the preceding items, wherein the detectable moiety is selected from the group consisting of a fluorophore, an enzyme or a radioactive tracer.

98. The composition for use, agent, method or use according to any one of the preceding items, wherein the moiety capable of emitting photons is a fluorophore.

99. The composition for use, agent, method or use according to any one of the preceding items, wherein the mammal is illuminated with a source of light capable of exciting said fluorophore.

100. The composition for use, agent, method or use according to any one of the preceding items, wherein the photons are detected using PET-scan or SPECT-scan.

101. The composition for use, agent, method or use according to any one of the preceding items, wherein the mammal is a human being.

102. An antibody-drug conjugate comprising an integrin-alpha 10 specific antibody covalently linked to a radioactive tracer.

103. The antibody-drug conjugate according to any one of the preceding items for use in the diagnosis of a malignant neoplasm of the central nervous system of such as a glioma, a neuroblastoma, or a medulloblastoma.

104. A nanoparticle comprising an integrin alpha-10 specific antibody and a radioactive tracer.

105. A kit for detecting a malignant neoplasm of the central nervous system, such as a glioma, in vitro, in situ or in vivo, the kit comprising an antibody specific for integrin alpha 10 subunit, a peptide capable of binding specifically to an integrin alpha 10 subunit antigen, or a polynucleotide probe capable of hybridizing specifically to an integrin alpha 10 subunit transcript or its complement, and optionally, instructions for use.

106. A method of treating a subject suffering from a malignant neoplasm in the central nervous system, said method comprising:
 a) determining if a subject is suffering from a malignant neoplasm of the central nervous system, according to any one of the preceding items; and
 b) administering to a subject diagnosed with a malignant neoplasm of the central nervous system, a therapeutically effective amount of an antibody specifically binding to an integrin alpha 10 subunit as defined in any one of the preceding items.

107. The method according to any one of the preceding items, wherein the detection of the integrin alpha 10 subunit comprises the steps of:
 a. obtaining a biological sample from said subject,
 b. analysing in said sample, the presence or absence of:
  i) an integrin alpha 10 subunit polypeptide, or
  ii) a polynucleotide transcript which encodes an integrin alpha 10 subunit polypeptide or a fragment or variant thereof,
 wherein presence of the integrin alpha 10 subunit polypeptide or polynucleotide transcript is indicative of a malignant neoplasm in the central nervous system of said mammal, and wherein the absence of the integrin alpha 10 subunit polypeptide or polynucleotide transcript is indicative of absence of a malignant neoplasm of the CNS.

108. The method according to any one of the preceding items, wherein the detection is performed using an antibody specifically binding to an integrin alpha 10 subunit.

109. The method according to any one of the preceding items, wherein the antibody is bound to a detectable moiety.

110. The method according to any one of the preceding items, wherein the detectable moiety is selected from the group consisting of a fluorophore, an enzyme or a radioactive tracer.

111. The method according to any one of the preceding items, wherein the detection of an integrin alpha 10 subunit is achieved by detection of the binding of a molecular probe or antibody to a peptide capable of specifically binding to an integrin alpha 10 subunit polypeptide or polynucleotide.

112. The method according to any one of the preceding items, wherein the sample is a brain tissue sample.

113. The method according to any one of the preceding items, wherein the sample is a brain tumour tissue sample.

114. The method according to any one of the preceding items, wherein the sample is a blood sample.

115. The method according to any one of the preceding items, wherein said detection is conducted as defined in any one of the preceding items.

116. The method, or the composition for use, according to any one of the preceding items, wherein the subject is a mammal such as a human being.

117. Use of a composition comprising an antibody specifically binding to integrin alpha 10 subunit for the manufacture of a medicament for the treatment of a malignant neoplasm in the central nervous system.

118. A method of inhibiting tumour associated vascularization in a mammal, the method comprising administering to said mammal a therapeutically effective amount of an anti-integrin alpha 10 subunit antibody according to any one of the preceding items.

119. An antibody-drug conjugate comprising an integrin-alpha 10 subunit specific antibody covalently linked to a ribosome inactivating protein.

120. The antibody-drug conjugate according to any one of the preceding items, wherein the ribosome inactivating protein is selected from the group consisting of shiga and shiga-like toxins; type I ribosome inactivating proteins, such as trichosanthin and luffin; type II ribosome inactivating proteins, such as ricin, agglutinin and abrin; and saporin.

121. The antibody-drug conjugate according to any one of the preceding items, wherein the ribosome inactivating protein is saporin.

122. The composition, agent, method, use or antibody drug conjugate according to any one of the preceding items, wherein the integrin alpha 10 subunit is as a part of an integrin alpha 10 beta 1 heterodimer.

EXAMPLES

Example 1: Integrin Alpha 10 Subunit Expression on Cells Isolated from Glioblastoma Brain Tumour A cell line deriving from patient material, obtained from brain tumour tissue samples collected as surgical biopsies at Lund University Hospital was cultured at 37 °C with 5% $CO_2$ in DMEM media supplemented with 10% FBS and 1% Pen Strep. Cells were grown to 70-90% confluence. Cells were washed in PBS (0.1 M, pH 7.4) and after trypsin treatment moved to the bottom of specialized microscope slides (Ibidi, Germany). The cells were grown to 50-100% confluence before fixation, followed by immunofluorescence labelling.

Immunofluorescence labelling of cells were made following the protocol:

1. The cell medium was removed/aspirated. The cells were fixated in cold (<10 °C) 4% PFA for 10-20 min.
2. The cells were rinsed in PBS (0.1M, pH 7.4) for 2×5 min.
3. The cells were incubated in blocking solution, PBS containing Triton-X 100 0.02% for 20 min.
4. The cells were incubated in PBS (0.1M, pH 7.4) containing Triton-X 100 0.001% (0.1-0.001%*) and bovine serum albumin (BSA) 1% for 20 min.
5. The cells were incubated in primary antibodies, 1 μg/ml alpha 10 MAb (1-2 μg) diluted in PBS (0.1M, pH 7.4) containing Triton-X 100 0.001% (0.1-0.001%*) and bovine serum albumin (BSA) 1% for 90 min.
6. The cells were rinsed in PBS (pH 7.4) for 2×10 min and then incubated in secondary antibodies, 1:150 (a-mouse AlexaFluor 488 and a-rabbit AlexaFluor 568 made in goat, Invitrogen, USA), diluted in PBS (0.1M, pH 7.4) containing Triton-X 100 0.001% (0.1-0.001%) and bovine serum albumin (BSA) 1% for 30 min.
7. The cells were rinsed in PBS (0.1M, pH 7.4) for 1+2×7 min.
8. The cells were incubated in DAPI (0.1 μM, in PBS) for >10 min.

No mounting required for analyses via inverted microscopes, as used here. For Imaging and analyses confocal microscopy was used.

Figure 2:
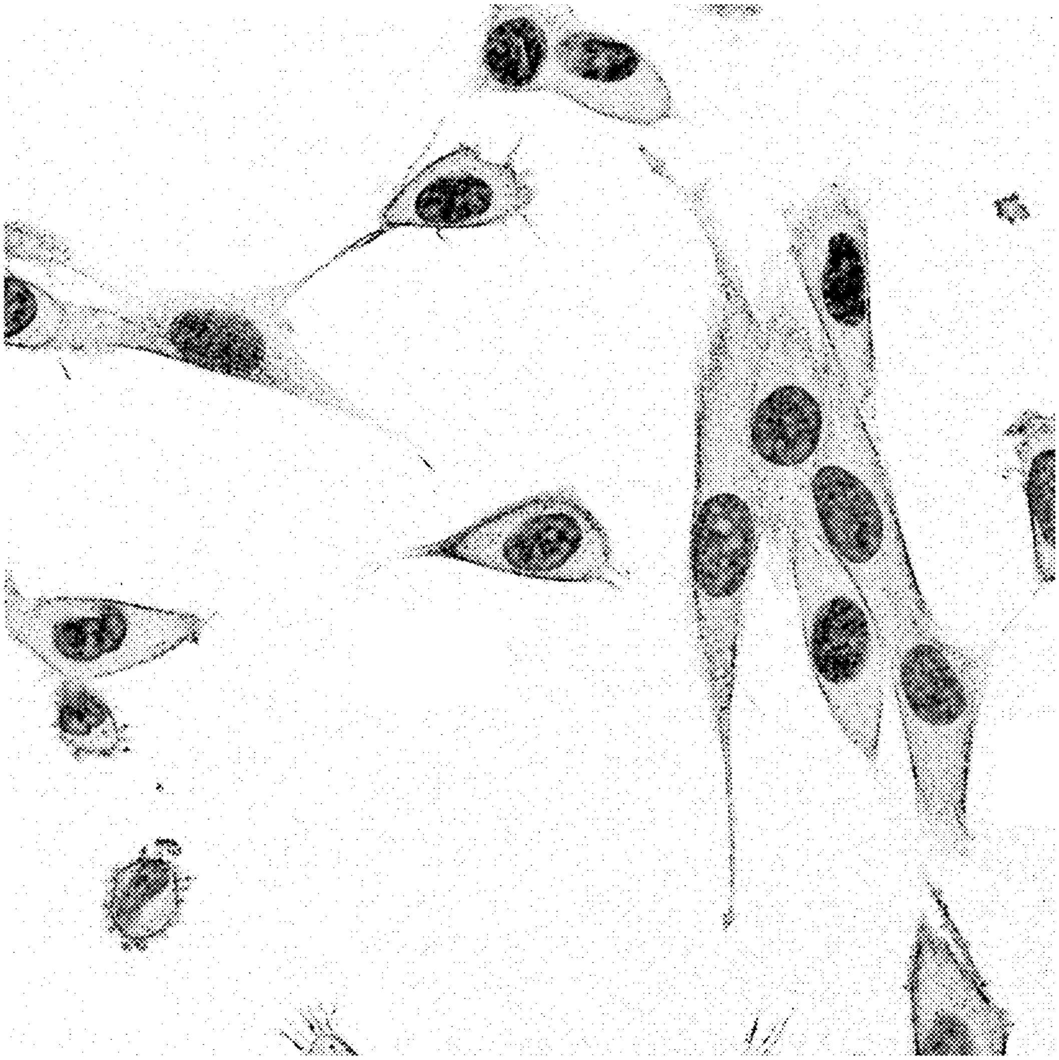
FIG. 2: Integrin $\alpha 10$ is expressed by cells isolated from glioblastoma tumour tissue. By using an antibody directed against integrin $\alpha 10$ it was shown that integrin $\alpha 10$ is specifically and strongly expressed on glioblastoma cells in a glioblastoma cell line visualized by immunofluorescence staining.

In conclusion, by using an antibody directed against integrin α10 (mAb 365, (WO 99/51639)) it was surprisingly shown that integrin α10 is specifically and strongly expressed on glioblastoma cells derived from glioblastoma (glioma grade IV, glioblastoma multiforme), the most aggressive form of glioma (FIG. 2).

Example 2: Integrin Alpha 10 Subunit Expression in Brain Tumour Tissue from Glioblastoma Patients Visualized by Immunofluorescence Brain tumour tissue samples were collected as surgical biopsies from patients at Lund University Hospital.

Tissues were sectioned, 5 μm (MICROM HM 360 microtome), and collected on SuperFrost Plus slides (Menzel-Gläser, GmbH). Sections were used for immunolabelling, directly or after postfixaton with acetone (100% at −20 °C, for 10 min, see below).

Fresh frozen tissues were embedded in TissueTek (Sakura, Jpn). Sections, 10 μm (made in a MICROM HM 500 OM cryostat), were collected on SuperFrost Plus slides. Sections were used for immunolabelling, after post-fixation with acetone (100% at −20 °C, for 10 min, see below).

After antigen retrieval, the following protocol was followed:

1. Rinse/buffer in PBS 5 min, at RT.
2. Block with PBS containing 1% BSA, for 20 min, at RT.
3. Rinse with PBS (PBS-Triton X100) 5 min, at RT.
4. Incubate sections with 0.03% $H_2O_2$ (in PBS), for 10 min, at RT (quench endogenous peroxidase activity)
5. Rinse in PBS, 5 min×2, at RT.
6. Incubate sections with primary antibodies, with alpha 10 PAb 1 μg/ml (0.6-1.2 μg/ml), diluted in PBS containing 1% BSA 0.05% Triton X100).
   over night (ca 16-18 h) at 4 °C.
7. Rinse in PBS 5 min×2 (same temperature as slides/sections!).
8. Apply conjugated secondary antibodies 30 min (a-rabbit), at RT.
   (diluted in PBS containing 1% BSA 0.05% Triton X100).
9. Rinse in PBS, 5 min×2, at RT.
10. Incubate/react in DAB/0.03% $H_2O_2$ solution, 1-10 min, at RT.
11. Rinse in PBS, 5 min×2, at RT.

Counter staining of immunolabeled sections:

1. Incubate with hematoxylin (Mayers), 2 min, at RT.
2. Rinse in PBS 3 min, at RT.
3. Wash with PBS 2 min, at RT.

Mounting:

Dehydrate sections via immersion in

1. In ethanol 70%, 96%, 100%×2, for 2 min in each concentration.
2. Xylene ≥3 min×2.
3. Mount the slides in Pertex® (Histolab, Sweden) and cover slip with glass slide (22× 30-50 mm).

Analysis and documentation: Bright-field microscopy provides good detection of the overall labelling distribution with cellular relation, especially in thin paraffin sections (5 μm).

Instruments: Leica DMRE microscope, using 10×/0.3 and 20×/0.5 Plan Apochromate objectives. Digital images (1360×1024 px) were acquired with a Leica DCF500 CCD-camera and image acquisition software LAS (Leica Application Suite) v4.4.

Figure 3:
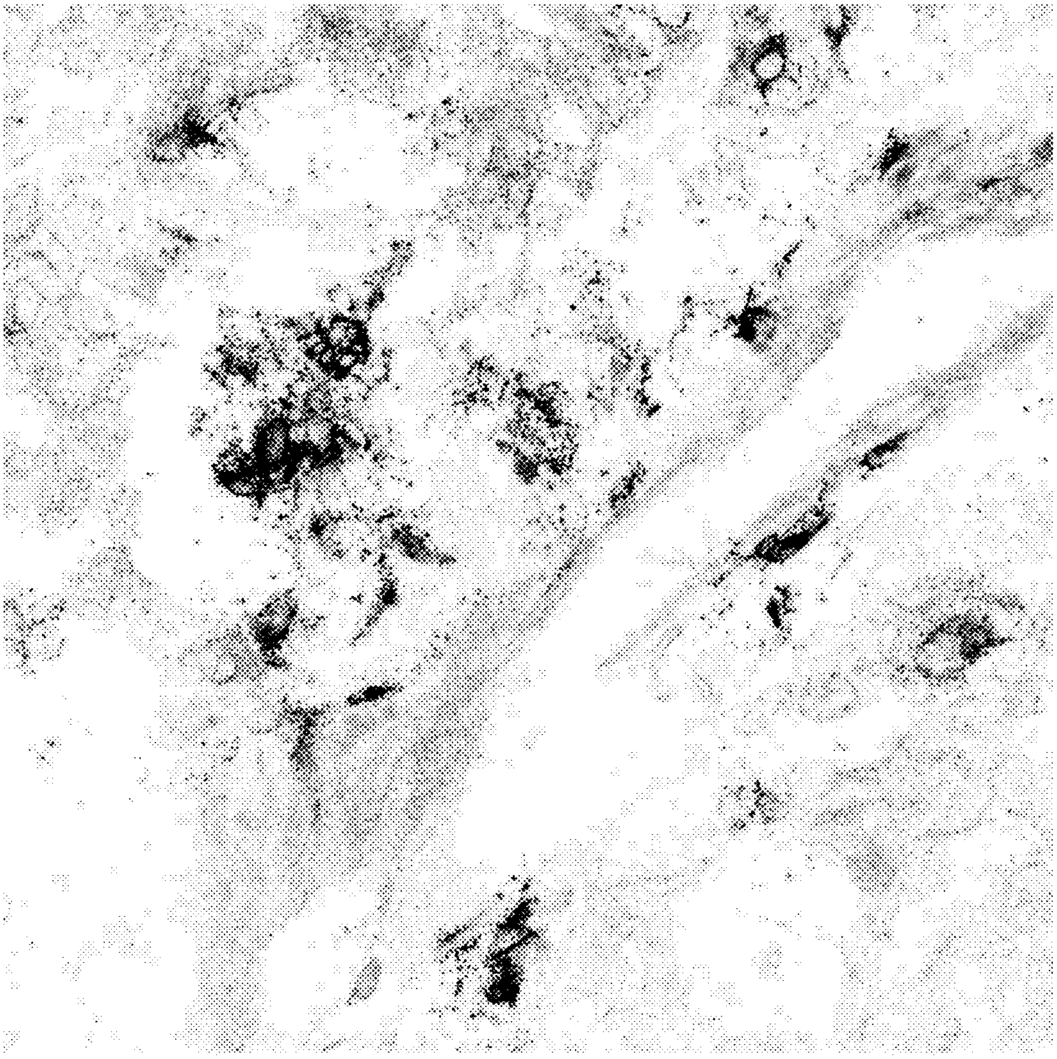
FIG. 3: Integrin $\alpha 10$ is expressed by cells in glioblastoma tissue. By using an antibody directed against integrin $\alpha 10$ it was shown that integrin $\alpha 10$ is specifically and strongly expressed on glioblastoma cells in patient material consisting of glioblastoma tissue samples visualized by immunofluorescence staining.

In conclusion, by using a polyclonal antibody directed against the integrin alpha 10 subunit it was surprisingly shown that the integrin alpha 10 subunit is specifically and strongly expressed on glioblastoma cells in tumour tissue samples collected as surgical biopsies from patients at Lund University Hospital (FIG. 3).

Example 3: Expression of Integrin Alpha 10 Subunit in Brain Tumour Tissue from Glioblastoma Patients Compared to Expression in Unaffected Brain Tissue Visualized by Immunohistochemistry Patient brain tissue samples from seemingly unaffected regions, and from regions with malignant brain tissue (as diagnosed by two independent pathologists), were collected as surgical biopsies from patients at Lund University Hospital.

Paraffin sections were deparaffinized and rehydrated via immersion of slides in xylene followed by an ethanol series and water according to standard protocols.

Paraffin sections were post-fixed in acetone followed by rinse in PBS, 5 min×2.

Paraffin sections were treated for antigen retrieval by immersing slides in an acidic buffered solution—citrate buffer (10 mM Sodium citrate, 0.05% Tween 20, pH 6.0) and heat treatment. After antigen retrieval, the following protocol was followed:

1. Rinse/buffer in PBS 5 min, at RT.
2. Block with PBS containing 1% BSA, for 20 min, at RT.
3. Rinse with PBS (PBS— Triton X100) 5 min, at RT.
4. Incubate sections with 0.03% $H_2O_2$ (in PBS), for 10 min, at RT (quench endogenous peroxidase activity)
5. Rinse in PBS, 5 min×2, at RT.
6. Incubate sections with primary antibodies, with alpha 10 PAb 1 μg/ml (0.6-1.2 μg/ml), diluted in PBS containing 1% BSA 0.05% Triton X100).
   over night (ca 16-18 h) at 4 °C.
7. Rinse in PBS 5 min×2 (same temperature as slides/sections).
8. Apply conjugated secondary antibodies 30 min (anti-rabbit), at RT.
   (diluted in PBS containing 1% BSA 0.05% Triton X100).
9. Rinse in PBS, 5 min×2, at RT.
10. Incubate/react in DAB/0.03% $H_2O_2$ solution, 1-10 min, at RT.
11. Rinse in PBS, 5 min×2, at RT.

Counter staining of immunolabeled sections:

1. Incubate with hematoxylin (Mayers), 2 min, at RT.
2. Rinse in PBS 3 min, at RT.
3. Wash with PBS 2 min, at RT.

Mounting:

Dehydrate sections via immersion in

1. In ethanol 70%, 96%, 100%×2, for 2 min in each concentration.
2. Xylene ≥3 min×2.
3. Mount the slides in Pertex® (Histolab, Sweden) and cover slip with glass slide (22× 30-50 mm).

Analysis and documentation: Bright-field microscopy provides good detection of the overall labelling distribution with cellular relation, especially in thin paraffin sections (5 μm).

Instruments: Leica DMRE microscope, using 10×/0.3 and 20×/0.5 Plan Apochromate objectives. Digital images (1360×1024 px) were acquired with a Leica DCF500 CCD-camera and image acquisition software LAS (Leica Application Suite) v4.4.

Figure 4:
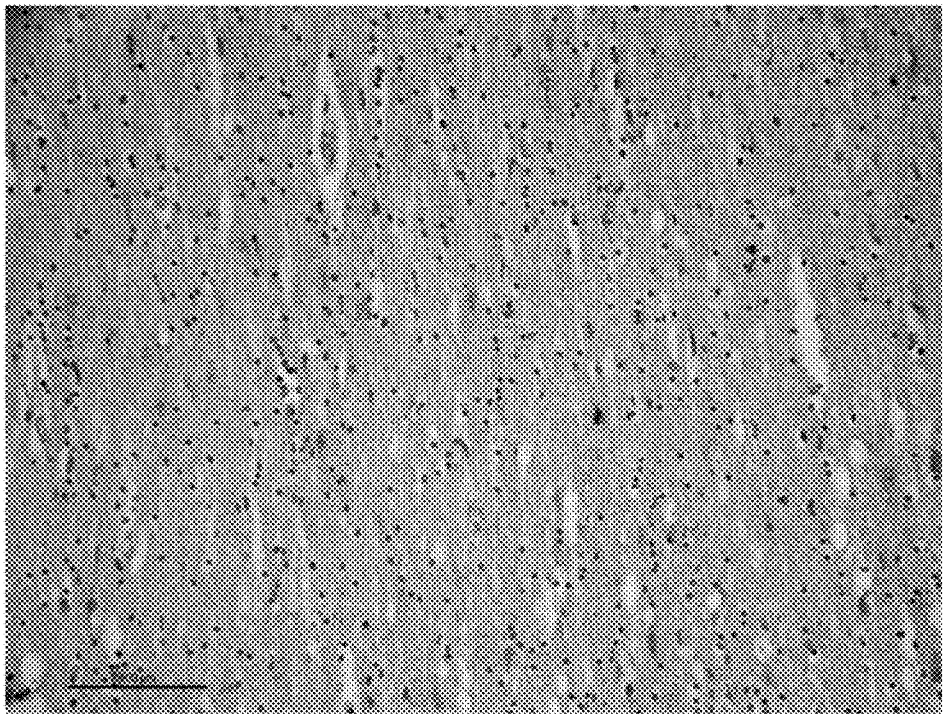
FIG. 4: Integrin α10 is detected in glioblastoma tissue but not in unaffected brain tissue.
Figure 4:
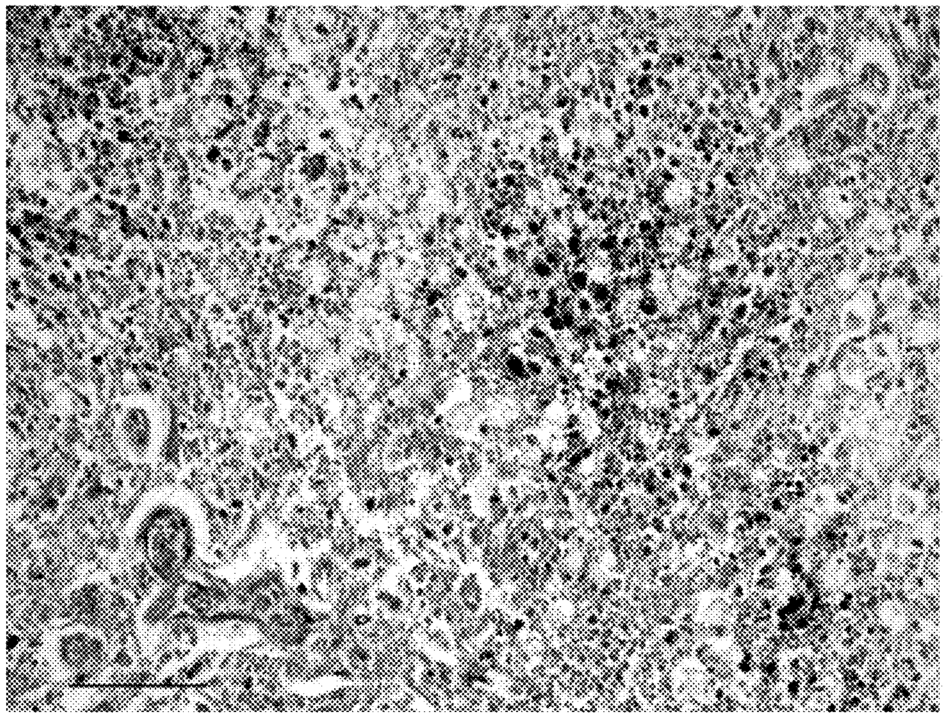

FIG. 4A shows a part of the patient sample with a seemingly unaffected brain morphology while FIG. 4B shows another part of the same sample with malignant brain tissue (glioblastoma multiforme). In conclusion, by using a polyclonal antibody directed against integrin alpha 10 subunit (Camper et al (1998) J Biol Chem. 273(32):20383-9) it was shown that integrin alpha 10 subunit is specifically and strongly expressed on glioblastoma cells, whereas negligible expression of integrin alpha 10 subunit was seen in morphologically unaffected brain tissue.

Example 4: Integrin Alpha 10 Subunit Expression in Brain Tumour Tissues Samples from Patients with Gliomas of Different Grades Patient material consisting of brain tumour tissue samples collected as surgical biopsies or post mortem from Lund University Hospital were used.

Tissues were sectioned, 5 μm (MICROM HM 360 microtome), and collected on SuperFrost Plus slides (Menzel-Glaser, GmbH). Sections were used for immunolabelling, directly or after postfixaton with acetone (100% at −20 °C, for 10 min, see below).

Fresh frozen tissues were embedded in TissueTek (Sakura, Jpn). Sections, 10 μm (made in a MICROM HM 500 OM cryostat), were collected on SuperFrost Plus slides. Sections were used for immunolabelling, after post-fixation with acetone (100% at −20 °C, for 10 min, see below).

1. Cryo-sections (freshly cut or from deep freeze): Air-dry sections in 37 °C, for about 20 min and let sections reach room temperature.
2. Rinse in PBS, >5 min×2
3. Post-fixation of sections in acetone, followed by rinse in PBS, 5 min×2
4. Apply silicone barrier ("PAP pen") around section.
5. Incubate/block in PBS containing 0.05% (0.1-0.001) TritonX-100 and 1% BSA, for 30 min, at RT.
6. Rinse in PBS 1×2 min
7. Incubate with primary antibodies mixed (as a "cocktail") with antibodies made against other antigens (firstly individually evaluated for the specificity and optimal working dilution) 16-18 hours at 4-8 °C, with α10 PAb 1.2 μg/ml (0.6-1.2 μg/ml) (diluted in PBS containing 0.05% TritonX-100 and 1% BSA).
8. For simultaneous fluorescence visualization two epitopes the primary and secondary antibodies, respectively, are applied as a mixture, a "cocktail".
9. Rinse in PBS, 1 min followed by 2×5 min.
10. Incubate sections with fluorophore conjugated secondary Ab/Abs (see below), in a mixture (against the different host animals of the primary antibodies) diluted 1:150, for 30-45 min, at RT.

Secondary antibodies for multiple labelling (highly affinity purified, mainly Fab2 fragments) were made in donkey or in goat against rabbit, mouse, or goat IgG's or against chicken IgY (Jackson, USA or Invitrogen, USA). Diluted in PBS containing 1% BSA. For simultaneous fluorescence visualization two epitopes the primary and secondary are applied as a mixture, a "cocktail".

11. Rinse in PBS— TritonX-100 for 2 min.
12. Rinse in PBS 1×5 min.
13. Incubate in organelle (nuclear) stain DAPI, 0.1 μM, diluted in PBS, for 15 min.
14. Rinse in PBS, 2×5 min.
15. Mount and coverslip in "anti-fade solution": ProLong Gold (Invitrogen, USA).

Analyses—Immunofluorescence-Confocal Laser Scanning Microscopy:

Confocal microscopy provided high resolution, signal-to-noise ratio of the labelling, and specific wave-length signal detection. Only analysis of confocal microscopic images can resolve the structural localization, extra/intracellular localization, and co-localization of labelling (via Z-stack optical sectioning and 3-D reconstructions).

Equipment:

The specimens were examined in a Zeiss LSM 510 META confocal microscope, utilizing lasers for excitation between 305-633 nm and detection of emission between 420-650 nm. Images were acquired with a 20×/0.8 Plan Apochromate and a 40Δ/1.3 oil immersion Plan Apochromate objective, with three immunofluorescence channels, one DAPI channels and one bright-field DIC channel.

Z-stacks (no DIC) of consecutive confocal planes were obtained with the 40×/1.3 objective, either with 1024×1024 px frame size (pixel width 0.22 μm), or with "zoom" (scanning a smaller area) and Nyquist optimal sampling frequency (pixel width 0.115 μm) for maximal resolution. Step size between consecutive confocal planes were according to Nyquist optimal sampling frequency (0.48 μm).

In conclusion, by using an antibody directed against integrin α10 (Camper et al (1998) J Biol Chem. 273(32): 20383-9) it was surprisingly shown that integrin α10 is specifically expressed on cells in patient material consisting of astrocytoma grade II (on few cells), astrocytoma grade III, glioblastoma multiforme also known as astrocytoma grade IV, brain tumour tissue samples (FIG. 5A-C). Interestingly, the expression of integrin α10 is increased with grades and is strongly expressed in astrocytoma grade III and IV. Note positive staining of cells in blood vessels or blood filled areas in all grades of astrocytoma (FIG. 5D).

Example 5: Expression of Integrin Alpha 10 Subunit in Patient Tumour Tissue Samples from Neuroblastoma and Medulloblastoma as Visualized by Immunohistochemistry Patient material consisting of neuroblastoma and medulloblastoma tissue specimens collected as surgical samples from Lund University and from Uppsala University Hospital were used. Paraffin sections were deparaffinized and rehydrated via immersion of slides in xylene followed by an ethanol series and water according to standard protocols. Paraffin sections were post-fixed in acetone followed by rinse in PBS, 5 min×2. Paraffin sections were treated for antigen retrieval by immersing slides in an acidic buffered solution—citrate buffer (10 mM Sodium citrate, 0.05% Tween 20, pH 6.0) and heat treatment. After antigen retrieval, the following protocol was followed:

1. Rinse/buffer in PBS 5 min, at RT.
2. Block with PBS containing 1% BSA, for 20 min, at RT.
3. Rinse with PBS (PBS— Triton X100) 5 min, at RT.
4. Incubate sections with 0.03% $H_2O_2$ (in PBS), for 10 min, at RT (quench endogenous peroxidase activity)
5. Rinse in PBS, 5 min×2, at RT.
6. Incubate sections with primary antibodies, with alpha 10 PAb 1 μg/ml (0.6-1.2 μg/ml), diluted in PBS containing 1% BSA 0.05% Triton X100), overnight (ca 16-18 h) at 4 °C.
7. Rinse in PBS 5 min×2 (same temperature as slides/sections!).
8. Apply conjugated secondary antibodies 30 min (anti-rabbit), at RT (diluted in PBS containing 1% BSA 0.05% Triton X100).
9. Rinse in PBS, 5 min×2, at RT.
10. Incubate/react in DAB/0.03% $H_2O_2$ solution, 1-10 min, at RT.
11. Rinse in PBS, 5 min×2, at RT.

Counter staining of immunolabeled sections:

1. Incubate with hematoxylin (Mayers), 2 min, at RT.
2. Rinse in PBS 3 min, at RT.
3. Wash with PBS 2 min, at RT.

Mounting:

Dehydrate sections via immersion in

1. In ethanol 70%, 96%, 100%×2, for 2 min in each concentration.
2. Xylene ≥3 min×2.
3. Mount the slides in Pertex® (Histolab, Sweden) and cover slip with glass slide (22× 30-50 mm).

Instruments: Leica DMRE microscope, using 10×/0.3 and 20×/0.5 Plan Apochromate objectives. Digital images (1360×1024 px) were acquired with a Leica DCF500 CCD-camera and image acquisition software LAS (Leica Application Suite) v4.4.

Analysis and documentation: Bright-field microscopy provides good detection of the overall labelling distribution with cellular relation, especially in thin paraffin sections (5 μm).

Figure 6:
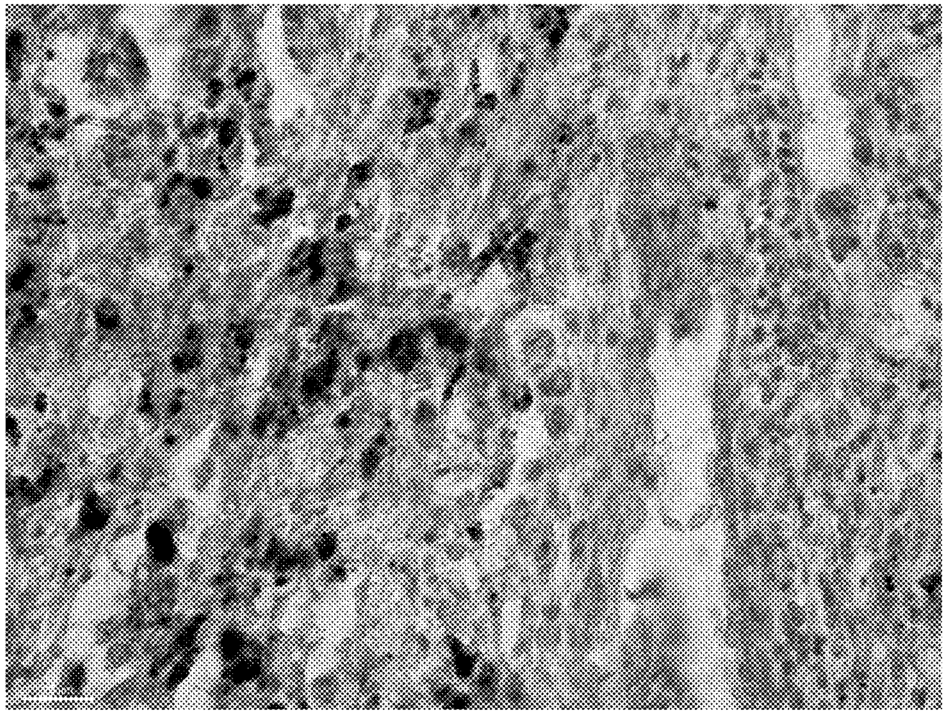
FIG. 6: Expression of integrin α10 in neuroblastoma and medulloblastoma. By using an antibody directed against integrin α10 it was shown that integrin α10 is specifically and strongly expressed on cells in neuroblastoma tumour tissue (A) and medulloblastoma tumour tissue (B) from patients as visualized by immunohistochemistry.
Figure 6:
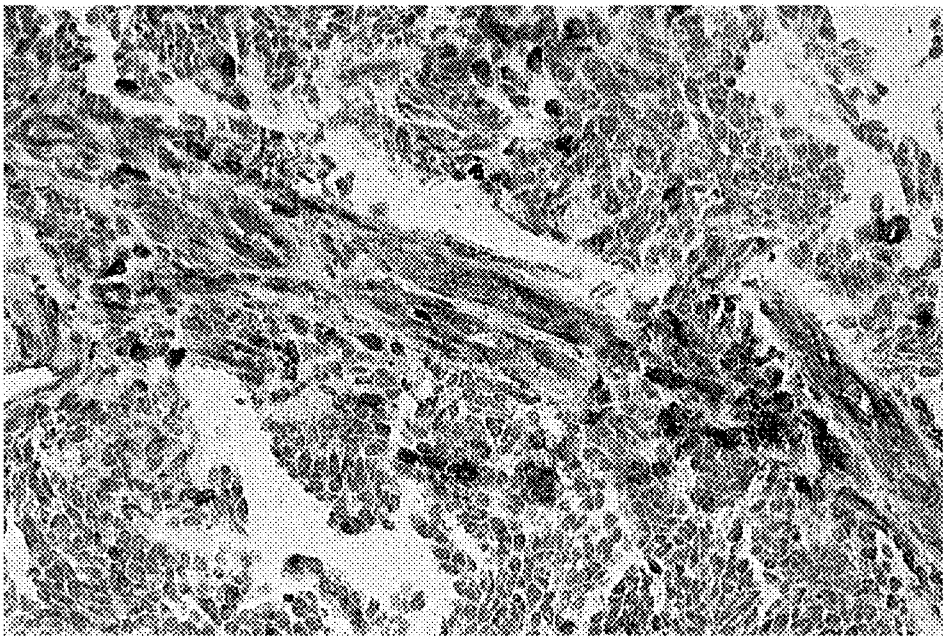

In conclusion, we find that integrin alpha 10 subunit is specifically and strongly expressed on cells in patient tumour tissue samples from malignant neuroblastoma and medulloblastoma (FIG. 6).

Figure 7:
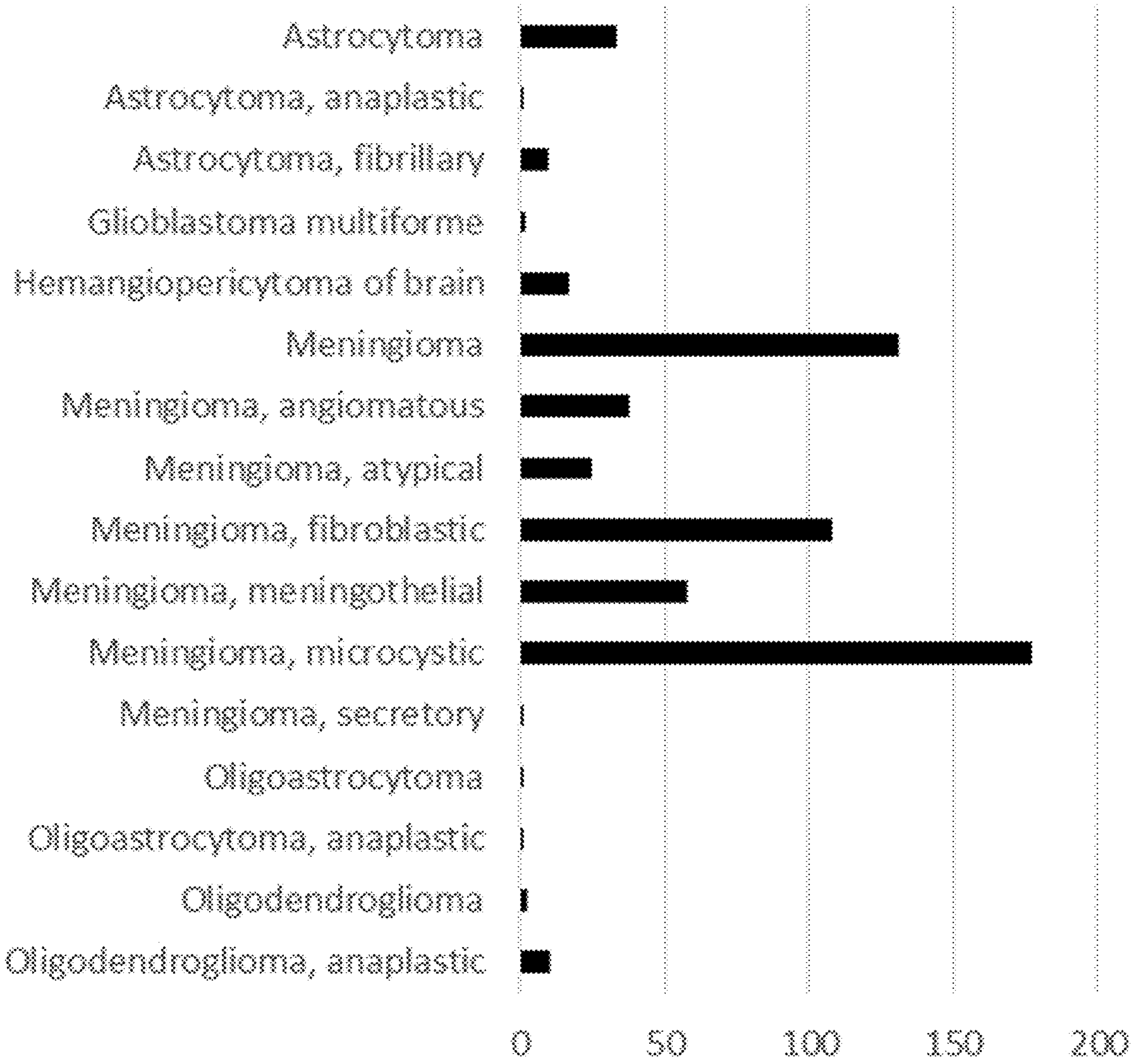
FIG. 7: Integrin α10 is detected in several brain tumour tissues. Brain Cancer cDNA Arrays were used for differential gene expression analysis and validation of gene expression in patient brain tumour tissue material. cDNAs of each array were synthesized from high quality total RNAs of pathologist-verified tissues, normalized and validated with beta-actin in two sequential qPCR analyses, and analysed together with clinical information. The figure shows mean relative quantification (RQ) values for two runs. As can be seen in the figure, mRNA for the integrin alpha 10 subunit can be detected in astrocytomas, anaplastic astrocytomas, fibrillary astrocytomas, glioblastoma multiforme, hemangiopericytomas of the brain, meningiomas, angiomatous hemangiomas, atypical meningiomas, fibroblastic meningiomas, meningiothelial meningiomas, microcystic meningiomas, secretory meningiomas, oligoastrocytomas, anaplastic oligoastrocytomas, oligodendrogliomas, and anaplastic oligodendrogliomas.

Example 6: Analysis of Alpha 10 RNA Expression in Brain Tumour from Patients by Quantitative PCR Quantitative PCR of brain tumour tissue samples collected as surgical biopsies from patients at Lund University Hospital was performed using primers for detection of integrin alpha 10 subunit. Brain Cancer cDNA Arrays (OriGene Technologies Inc.) were used for differential gene expression analysis and validation of gene expression in patient tissue material from different brain tumours. cDNAs of each array were synthesized from high quality total RNAs of pathologist-verified tissues, normalized and validated with beta-actin in two sequential qPCR analyses, and analysed together with clinical information. The real-time PCR detection of integrin alpha 10 subunit were conducted using gene specific primer and TaqMan probe (gene expression assay HS00174623_m1, Life Technology) and run as recommended by the manufactures. The detection system used were ICycler (Bio-Rad). Brain cancer tissue integrin alpha 10 subunit expression were normalized against healthy brain tissue and relative quantification values (RQ) of integrin alpha 10 subunit were calculated. FIG. 7 shows mean relative quantification values for two runs. RQ is defined as $2^{-\Delta\Delta Ct}$ where $\Delta\Delta Ct = \Delta Ct_{tumor\ sample} - \Delta Ct_{normal\ brain\ tissue}$ and $\Delta Ct$ is obtained from $Ct_{ITGA10} - Ct_{beta\text{-}actin}$.

As can be seen in FIG. 7, integrin alpha 10 subunit was surprisingly detected in several brain tumors including astrocytomas, anaplastic astrocytomas, fibrillary astrocytomas, glioblastoma multiforme, hemangiopericytomas of the brain, meningiomas, angiomatous hemangiomas, atypical meningiomas, fibroblastic meningiomas, meningiothelial meningiomas, microcystic meningiomas, secretory meningiomas, oligoastrocytomas, anaplastic oligoastrocytomas, oligodendrogliomas, and anaplastic oligodendrogliomas.

Example 7: Analysis of Co-Expression of Integrin Alpha 10 Subunit and Other Markers A tumour is heterogenous and consists of many different cell types. To show different types of cells positive for integrin alpha 10 subunit expression in gliomas (GBM), several markers that typically and specifically immunolabel different cell types were used in brain tumour glioblastoma tissue samples collected as surgical biopsies or post mortem from Lund University Hospital.

Sample Preparation:

Fresh frozen tissues were embedded in TissueTek (Sakura, Jpn). Sections, 10 μm (made in a MICROM HM 500 OM cryostat), were collected on SuperFrost Plus slides. Sections were used for immunolabeling, after post-fixation with acetone (100% at −20 °C, for 10 min).

Cryo-sections (freshly cut or from deep freeze) were air-dried in 37 °C, for about 20 min. When the sections have reached room temperature they were rinsed twice in PBS for 5 min. Sections were post-fixated in acetone followed by yet two rounds of rinse in PBS, (5 min×2). A silicone barrier ("PAP pen") was applied around the sections. The sections were incubated in PBS containing 0.05% (0.1-0.001) Triton X-100 and 1% BSA, for 30 min, at RT and then rinsed in PBS 1×2 min. The sections were incubated with primary antibodies mixed with antibodies made against other antigens (first individually evaluated for the specificity and optimal working dilution) for 16-18 hours at 4-8 °C, with α10 PAb 1.2 μg/ml (0.6-1.2 μg/ml) (diluted in PBS containing 0.05% Triton X-100 and 1% BSA). For simultaneous fluorescence visualization two epitopes, the primary and secondary antibodies respectively, were applied as a mixture ("cocktail"). The sections were rinsed in PBS, 1 min followed by 2×5 min and incubated with fluorophore conjugated secondary Ab/Abs in a mixture, diluted 1:150, for 30-45 min, at RT.

Secondary antibodies for multiple labelling (highly affinity purified, mainly Fab2 fragments) were made in donkey or in goat against rabbit, mouse, or goat IgG's or against chicken IgY (Jackson, USA or Invitrogen, USA). Diluted in PBS containing 1% BSA. For simultaneous fluorescence visualization of two epitopes the primary and secondary were applied as a mixture, a "cocktail". The sections were rinsed in PBS-Triton X100 for 2 min, and rinsed in PBS 1×5 min. The sections were incubated in organelle (nuclear) stain DAPI, 0.1 μM, diluted in PBS, for 15 min and rinsed in PBS, 2×5 min. The sections were mounted and coverslipped in "anti-fade solution": ProLong Gold (Invitrogen, USA).

Antibodies used in the present study:

| IGT # | Antigen | Host species | Supplier | Product no. |
|---|---|---|---|---|
| #EXT28 | EGFRvIII monoclonal | Mouse mAb | Biorbyt | orb47907 |
| #524 | Nestin | Goat pAb | R&D Systems | |
| #384b | Nestin | Mouse mAb | Chemicon | MAB5326 |
| #521 | PSA-NCAM | Mouse IgM | Millipore | #MAB5324 |
| #526 | GFAP | Goat pAb IgG | Abcam | ab53554 |
| #EXT16 | CD140b (PDGFRB) | Mouse mAb | Abcam | ab69506 |
| #EXT13 | CD31 (PECAM-1) | Goat pAb | Santa Cruz biotechnology | sc-1505 |
| #540 | CD45 | Mouse mAb | BD Pharmingen | 555480 |
| #EXT18 | CD68 | Mouse mAb | Dako | M0718 |
| #EXT26 | CD163 monoclonal | Mouse mAb | Abcam | ab17051 |
| #EXT27 | hMMR/CD206 polyclonal | Goat IgG | R&D systems | AF2534 |

Analysis:

Analysis was conducted by confocal laser scanning microscopy. Confocal microscopy provided high resolution, signal-to-noise ratio of the labelling, and specific wavelength signal detection. Only analysis of confocal microscopic images can resolve the structural localization, extra/intracellular localization, and co-localization of labelling (via Z-stack optical sectioning and 3-D reconstructions).

The specimens were examined in a Zeiss LSM 510 META confocal microscope, utilizing lasers for excitation between 305-633 nm and detection of emission between 420-650 nm. Images were acquired with a 20×/0.8 Plan Apochromate and a 40Δ/1.3 oil immersion Plan Apochromate objective, with three immunofluorescence channels, one DAPI channels and one bright-field DIC channel.

Z-stacks (no DIC) of consecutive confocal planes were obtained with the 40Δ/1.3 objective, either with 1024×1024 px frame size (pixel width 0.22 μm), or with "zoom" (scanning a smaller area) and Nyquist optimal sampling frequency (pixel width 0.115 μm) for maximal resolution. Step size between consecutive confocal planes were according to Nyquist optimal sampling frequency (0.48 μm).

Quantitative analysis of integrin alpha 10 co-existence with the different markers was made using digitalized image data. Data was analyzed from single channels, representing different labelings. Regions of interest (ROI) were first identified through identification of cell nuclei. An area 1 micrometer around the nuclei was used for analysis of co-expression of markers. Threshold values for positive staining were determined by visual inspection by an experienced microscopy operator and set at 5%.

Results: Table 1 below shows the expression pattern for markers co-expressing with the integrin alpha 10 subunit. Antibodies used directed against the antigens are indicated in the left column hand. The different cell types expected to express the antigens (immuno phenotypes) are indicated in the middle column. Degree of co-expression of each marker with integrin α10 is indicated in the right column.

TABLE 1

| Marker matrix | | |
|---|---|---|
| Cellular markers | Cells expected to express this marker | Degree of overlapping labelling with integrin α10 |
| EGFRvIII | Malignant cells | 71-100% |
| Nestin | Stem cells/Progenitor cells<br>Neural progenitor cells<br>Malignant cells | 1-10% |
| PSA-NCAM | Malignant cells | 1-10% |
| GFAP | Astrocytes<br>Progenitor cells<br>Malignant cells | 11-30 |
| PDGFRb (CD140b) | Pericytes<br>Progenitor cells<br>Malignant cells | 1-10% |
| PECAM-1 (CD31) | Endothelial cells<br>Progenitor cells<br>Malignant cells | 1-10% |
| CD45 | Hematopoietic cells including; T-cells, B-cells, NK-cells, Dendritic cells, Macrophages, Monocytes<br>Malignant cells | 31-70% |
| CD68 | Macrophages<br>Microglia<br>Malignant cells | 71-100% |
| CD163 | Macrophages<br>Microglia<br>Malignant cells | 11-30% |

TABLE 1-continued

| Marker matrix | | |
|---|---|---|
| Cellular markers | Cells expected to express this marker | Degree of overlapping labelling with integrin α10 |
| CD206 | Macrophages<br>Microglia<br>Malignant cells | 11-30% |

Co-expression and co-localisation CD163, CD206 and the integrin alpha 10 subunit is shown in FIG. 8 and co-expression and co-localisation of EGFRvIII and the integrin alpha 10 subunit is shown in FIG. 9.

Example 8: Migration Assay

Malignant cells are dependent on migration to spread and metastasize. In order to elucidate if integrin alphal 0 is important for this cellular process, migration assays are performed.

The migration assay is performed using CytoSelect Cell Migration Assay kit (Cell Biolabs', US). This is a two-chamber system where cell are allowed to migrate from the upper chamber to the lower compartment, which is filled with chemoattractant medium. The chambers are separated with a membrane that only allows actively migrating cells to pass. Glioma cells (GBM) obtained e.g. from primary cultures or established cell lines, are harvested using accutase, resuspended in medium without fetal calf serum (FCS) and transferred to the upper compartment of the CytoSelect insert. The migration assays are performed using monoclonal unconjugated and/or antibody-drug-conjugate (ADC) antibodies against integrin alpha 10 subunit, or IgG control antibodies. After incubation at 37 °C for 24-48 h, the inserts are collected and the cells adhering to the lower surface are fixed, stained and quantified.

Glioma cells incubated with an antibody against integrin alpha 10 subunit show reduced migration capacity.

Example 9: Analysis of Apoptosis—Cell Morphology and Flow Cytometry

Cells are dependent on integrin adhesion to the extracellular matrix in order to survive. If these integrin-matrix bonds are broken, cells may go into apoptosis. In order to elucidate whether induction of apoptosis occurs in glioma (GBM) cells when integrin α10 bonds are broken, apoptosis assays are performed.

Glioma cells (GBM) are cultured in 6-well plates and incubated overnight for determination of apoptosis. Unconjugated or ADC monoclonal antibodies against integrin alpha 10 subunit, or IgG control antibodies are added the day after. Morphological changes are observed using an inverted microscope, and cells are harvested for flow cytometry analysis after 72 h treatments to observe early and late apoptosis. The degree of apoptosis induced by integrin alpha 10 subunit antibody is determined by a commercially available apoptosis detection kit such as FITC annexin V Apoptosis detection kit with 7-AAD (Biolegend) and the data is analyzed by flow cytometry. In flow cytometry analysis, Annexin V-FITC single positive cells represent early apoptotic cells. Annexin V-FITC and 7-AAD (7-amino-actinomycin D) double positive staining cells represent late apoptotic cells. Positive staining for 7-AAD only represents the necrotic population of cells.

Glioma cells incubated with an antibody against integrin alpha 10 subunit show enhanced apoptosis.

Example 10: Sphere Formation Capacity of Glioma Cells (GBM) Treated with Monoclonal Antibody Against Integrin Alpha 10 Subunit A common in vitro assay to determine self-renewal capacity of a cell population, and thus their capacity to induce tumors in vivo upon xenograft transplantation, is the sphere formation assay.

Glioma cell lines (GBM) from the Human Glioma Cell Culture (HGCC) biobank, Uppsala University were used in this assay and these cells are derived from patient material obtained from brain tumour tissue samples collected as surgical biopsies as described by Xie et al. 2015 (EBioMedicine. 15; 2(10):1351-63). The cells were cultured in DMEM/F12 w/Glutamax and Neurobasal media (1:1) supplemented with 50× B27, 100× N2, 1% Pen Strep, bFGF (10 ng/ml) and EGF (10 ng/ml) at 37 °C with 5% $CO_2$. To evaluate the sphere formation capacity, cells were treated with accutase, collected and centrifuged for 4 min at 300 xg and then resuspended in media. The assay was performed in 96-well plates and 5000 cells were seeded per well. The cells were treated with varying concentrations of the monoclonal antibody against integrin alpha 10 subunit or an IgG control antibody. All treatments were done in triplicate. After 7 days of incubation at 37 °C with 5% $CO_2$, microscopy images of each well were taken and spheres that had reached a diameter of 100 μm were counted.

Figure 10:
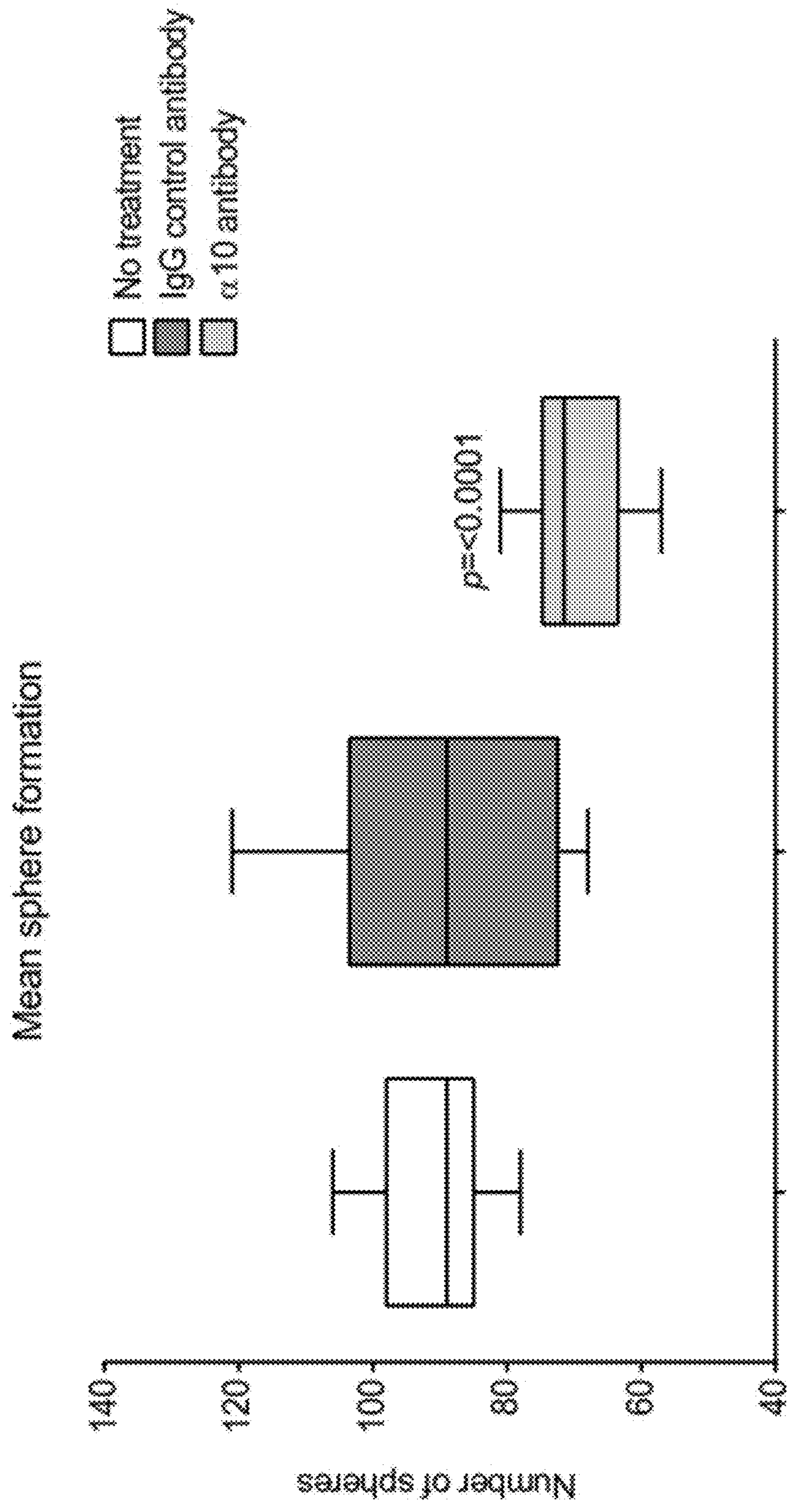
FIG. 10: Antibodies to integrin alpha 10 subunit inhibit sphere formation of glioblastoma cells. The figure shows that a monoclonal antibody binding to integrin alpha 10 subunit on the glioblastoma cells were able to reduce the sphere formation capacity compared to untreated cells. This effect was not seen in cells treated with IgG control antibody.

In conclusion, by using a monoclonal antibody against integrin alpha 10 subunit glioma cells show reduced sphere formation capacity compared to untreated cells. This effect was not seen in cells treated with IgG control antibody (FIG. 10).

Example 11: Viability and Growth of Glioma Cells (GBM) Treated with Antibody Against Integrin Alpha 10 Subunit One of the hallmarks of cancer is the sustained proliferative signals in malignant cells. In order to elucidate if anti-integrin alpha 10 subunit antibodies are capable of inhibiting glioma cell viability and proliferation, Colorimetric Cell Viability assays such as WST-1 (Roche, DE) and XTT were performed. The colorimetric cell viability assays comprise tetrazolium salt, which is reduced into a coloured formazan compound in metabolically active cells. Thus, the amount of formazan dye is correlated to number of viable cells.

For cell viability assays, glioma cells obtained from primary cultures were treated with accutase, collected and centrifuged for 4 min at 300 xg and then resuspended in media. Several glioma (GBM) cell lines were used. The one from Lund University was cultured in DMEM media supplemented with 10% FBS and 1% Pen Strep whereas the HGCC cell lines were cultured in in DMEM/F12 w/Glutamax and Neurobasal media (1:1) supplemented with 50× B27, 100× N2, 1% Pen Strep, bFGF (10 ng/ml) and EGF (10 ng/ml) at 37 °C with 5% $CO_2$. A density of 5000 cells per well were used and the 96-well plates were coated with laminin (Cultrex® Mouse Laminin I, R&D systems) for good plastic adherence of the HGCC cells. The following day, varying concentrations of the unconjugated monoclonal antibody against integrin alpha 10 subunit was added. Cells were also treated with a combination of the unconjugated monoclonal antibody against integrin alpha 10 subunit and a secondary antibody conjugated with saporin (ATSbio, US), which is a good in vitro model system. As control, untreated cells as well as a control antibody were used. All treatments were done in triplicate. The cells were further cultured at 37 °C with 5% $CO_2$ for 72 h. Cell viability was assessed by adding 10-50 μl tetrazolium salt reagent into each well followed by incubation at 37 °C for 1-4 h. The plates were gently shaken and the absorbance of the samples was measured using a spectrophotometer (SpectraMax i3) at a wavelength of 450-500 nanometer.

Figure 11:
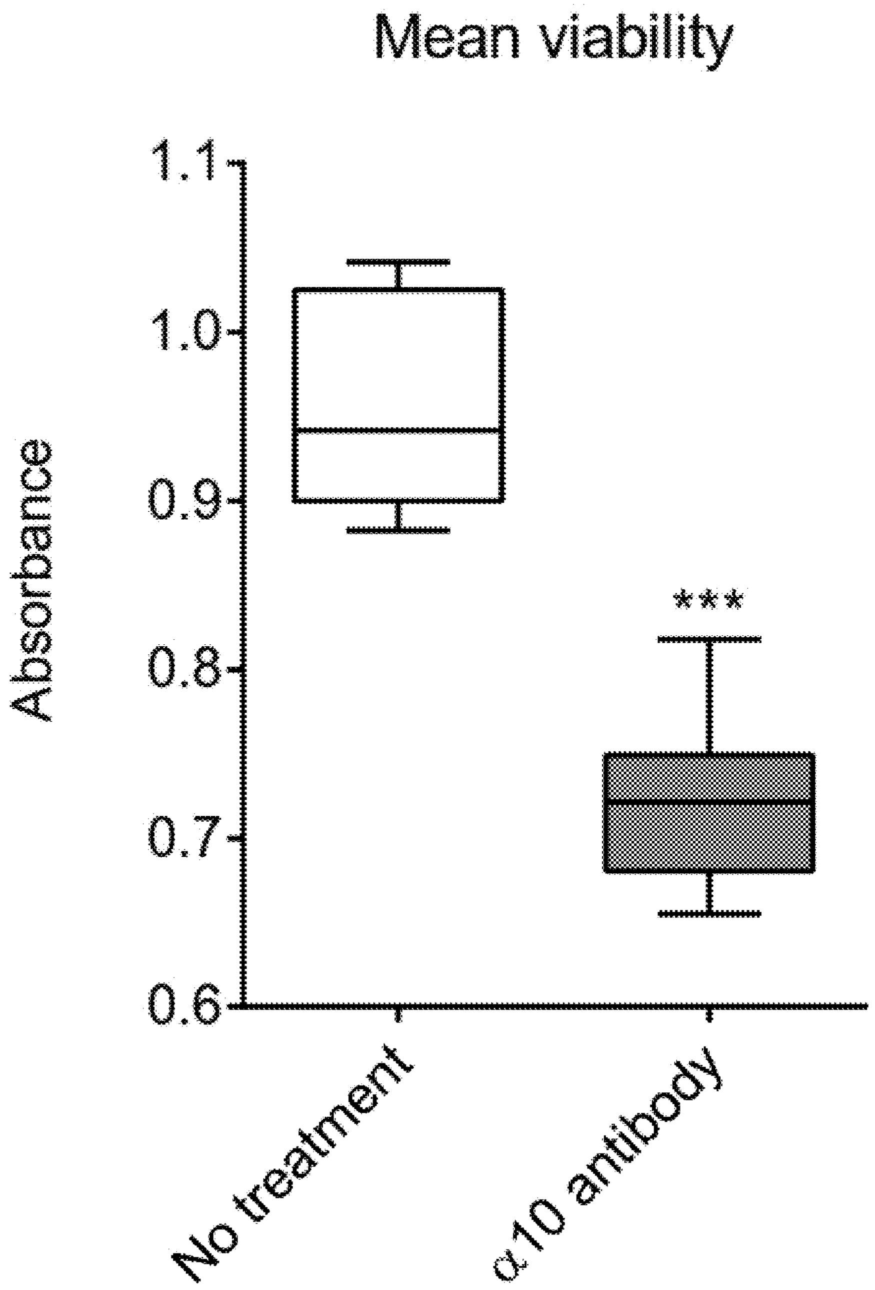
FIG. 11: Antibodies to integrin alpha 10 subunit decrease viability and/or growth of glioblastoma cells. The figure shows that glioma (GBM) cells are sensitive to treatment with unconjugated monoclonal antibody against integrin alpha 10 subunit using WST-1 assay. Treatment with anti-integrin alpha 10 antibody decreased cell viability and/or growth of glioblastoma cells compared to untreated cells.
Figure 12:
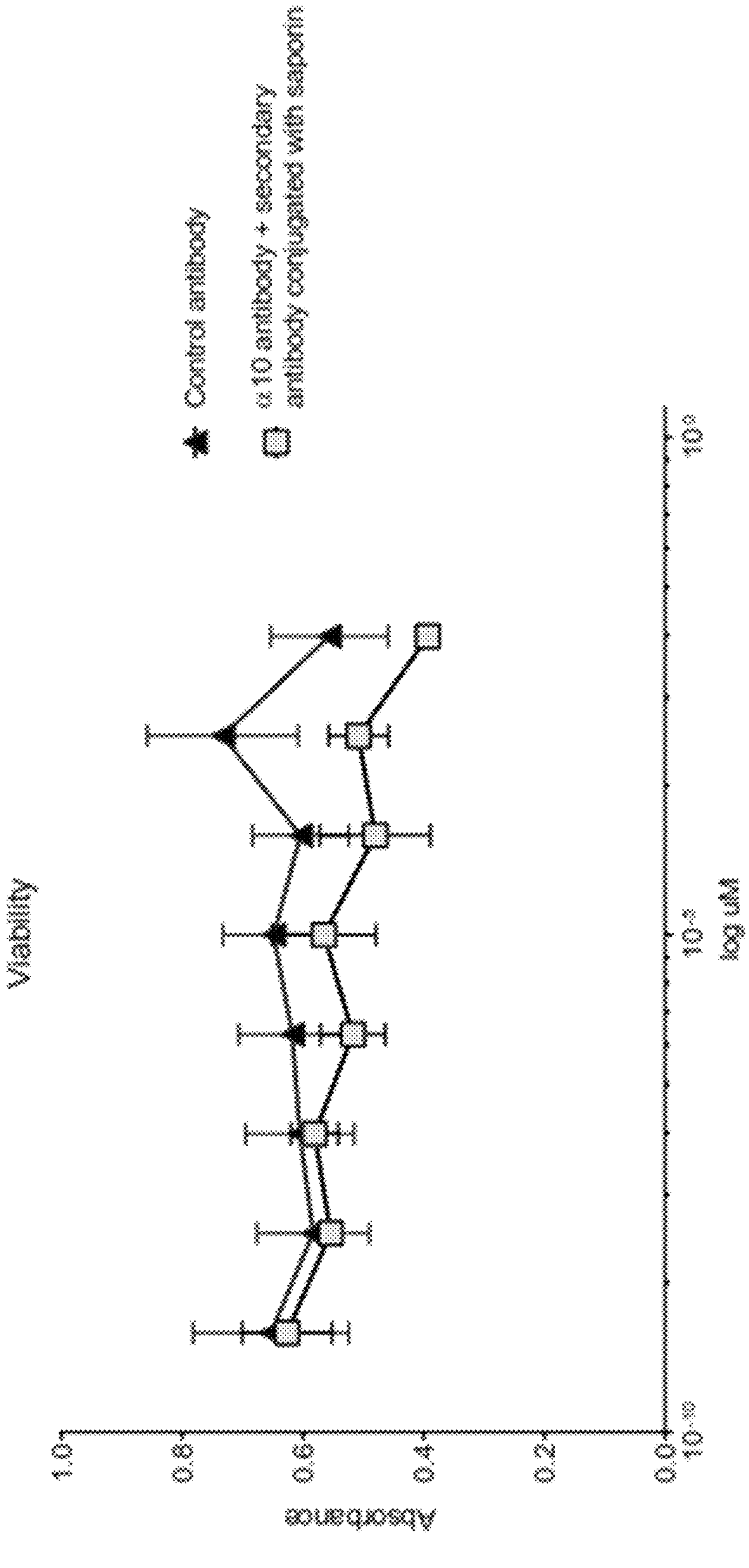
FIG. 12: Antibodies to integrin alpha 10 subunit decrease cell survival and/or proliferation of glioblastoma cells. The figure shows that treatment of glioblastoma cells with monoclonal antibodies to alpha10, followed by addition of a secondary antibody (binding to the alpha10 antibody) conjugated with saporin, reduced survival and/or proliferation of the glioblastoma cells in comparison to treatment with a control antibody.

As can been seen in FIG. 11, treatment with the unconjugated monoclonal antibody against integrin alpha 10 subunit alone significantly decreased cell viability and/or proliferation compared to untreated glioma (GBM) cells. FIG. 12 shows reduced survival and/or growth of glioma (GBM) cells treated with a monoclonal antibody against integrin alpha 10 subunit in combination with a secondary antibody conjugated with saporin, in comparison to a control antibody.

Example 12: In Vivo Murine Model for Functional Assessment of Integrin alpha10beta1 as a Candidate Target for Treatment of Malignancies in the Central Nervous System (CNS)

In order to demonstrate antitumour effect of the unconjugated integrin alpha10 antibody or conjugated integrin alpha10 antibody (Antibody Drug Conjugate, ADC) comprising anti-integrin alpha10 antibody as an anti-cancer agent a stereotactic orthotopic brain tumour xenograft model of immunocompromised mice is used. Human tumour cells are transplanted into the brains of immune-compromised mice. The method for injecting the cancer cells orthotopically is performed essentially as described by Joo K M et al. 2013 (Cell Rep. 3, 260-73).

Different doses of the unconjugated/ADC monoclonal antibody against integrin alpha10 or control antibody are administered to model animals upon malignant cell transplantation and at different time points following induction of the neoplasms. The antibody is introduced by intravenous-, intratumoural-, or intraventricular injections. The therapeutic effect of the integrin alpha10 specific antibody is assessed by comparing anti-integrin alpha10 treated animals with animals treated with control antibody.

The assessment of the therapeutic value of the reagent is performed by multiple pathological comparisons based on organ, cellular and molecular analyses as well as survival. Examples of pathological traits and markers are:

- Tumour size
- Tumour growth rate
- Morphological, molecular and histopathological features
- Invasiveness
- Gene expression of malignant markers
- Cell cycle status
- Apoptosis One goal of the present experiment is to determine the most effective dose of reagent without causing or eliciting a toxic reaction. The main and general steps of the in vivo strategic set-up, containing a more detailed experimental plan, are introduced below:

Detailed Experimental Plan

In general, the development of glioma from initiation day (day 0), i.e. from injection of neoplastic cells into the normal graft host, to a totally developed tumour in the host animal is about 2-20 weeks depending on the chosen xenograft model. The study is divided into three different stages:

1. Initiation
2. Progression
3. Termination

Stage 1, Initiation:

Before the injection of malignant cells, the following steps are performed at day 0.

Preparation of Cells for Transplantation:

a) Tumour cell lines, or
b) Tumour dissociation in order to obtain primary malignant cell suspensions For orthotopic transplantation into mouse brain, the stereotactic apparatus is prepared according to the manufacturer's instruction.

Surgical Procedure:

At least five animals are used for each injection condition and each time point.

a) Pre-operative animal preparation (anesthetize, clean, fixation of animal)
b) Pre-operative cell preparation (cell wash and count)
c) Procedural care (maintenance of anaesthesia and surgical procedure)
d) Injection of cells
e) Care and monitoring of animal Stage 2, Progression:

The experimental animals are divided into four groups based on treatment regimes. The groups are:

1. Group 1: untreated group. No treatment with antibody.
2. Group 2: control group. Treatment with control antibody.
3. Group 3: ITGA10 group. Treatment with unconjugated/ADC antibody against integrin alpha 10 subunit.

Stage 3, Termination:

The animals are sacrificed according to established protocols and the brain tumours are isolated in order to acquire all the necessary information regarding morphological, molecular and histopathological features, invasiveness, gene expression data of malignant markers, cell cycle status and apoptosis.

Example 13: Overview of Sequences

SEQ ID NO 1: Human integrin alpha 10 subunit
SEQ ID NO 2: Extracellular domain of human integrin alpha 10 subunit
SEQ ID NO 3: I-domain of human integrin alpha 10 subunit
SEQ ID NO: 4 *Homo sapiens* integrin subunit alpha 10 precursor, mRNA, complete cds

The invention claimed is:

1. A method for detecting a malignant neoplasm in the central nervous system of a mammal characterized by integrin alpha 10 subunit expression, said method comprising (1) obtaining an isolated sample comprising cells from the central nervous system from the mammal; and (2) detecting in the isolated sample the presence of:

a) an antigen comprising an integrin alpha 10 subunit polypeptide; and/or b) a polynucleotide transcript which encodes an integrin alpha 10 subunit polypeptide or a fragment or variant thereof, by contacting the sample with a reagent comprising an antibody with specificity for integrin alpha 10 subunit, or an integrin alpha 10 subunit nucleic acid probe that binds to an integrin alpha 10 subunit mRNA or cDNA, and detecting binding between the antibody with specificity for integrin alpha 10 subunit and the antigen comprising an integrin alpha 10 subunit polypeptide, or between the integrin alpha 10 subunit nucleic acid probe and the polynucleotide transcript which encodes an integrin alpha 10 subunit polypeptide or a fragment or variant thereof, wherein the antibody is covalently bound to a detectable moiety, wherein the malignant neoplasm comprises malignant cells or tumour-associated cells of the central nervous system expressing an integrin alpha 10 subunit, and wherein the presence of the antigen of a) and/or the polynucleotide transcript of b) is indicative of a malignant neoplasm in the central nervous system of said mammal, said method further comprising administering to the mammal a therapeutically effective amount of an antibody specifically binding to an integrin alpha 10 subunit.

2. The method according to claim 1, said method further comprising detecting in the isolated sample, the presence of:

c) a second antigen comprising a polypeptide selected from the group consisting of EGFRvIII, Nestin, PSA-NCAM, GFAP, PDGFRb (CD140b), PECAM-1 (CD31), CD45, CD68, CD163, and CD206; and/or d) a second polynucleotide transcript which encodes a polypeptide or a fragment or variant thereof, wherein said polypeptide is selected from the group consisting of EGFRVIII, Nestin, PSA-NCAM, GFAP, PDGFRb (CD140b), PECAM-1 (CD31), CD45, CD68, CD163, and CD206;

wherein the presence of the first antigen of a) and/or the first polynucleotide transcript of b); together with the second antigen of c) and/or the second transcript of d), indicates that said mammalian cell is a malignant cell or a tumour-associated cell.

3. The method according to claim 1, wherein the malignant cells or tumour-associated cells are selected from glial cells, pericytes, endothelial cells, hematopoietic cells, stem cells, microglia, T-cells, B-cells, plasma cells, NK-cells, dendritic cells, macrophages and monocytes.

4. The method according to claim 1, wherein said cell is selected from EGFRVIII+ cells, Nestin+ cells, PSA-NCAM+ cells, GFAP+ cells, PDGFRb+ cells (CD140b+ cells), PECAM-1+ cells (CD31+ cells), CD45+ cells, CD68+ cells, CD163+ cells and CD206+ cells, or any combination thereof.

5. The method according to claim 1, wherein the malignant neoplasm is selected from tumours of neuroepithelial tissue, astrocytic tumours, oligodendroglial tumours, oligoastrocytic tumours, ependymal tumours, choroid plexus tumours, neuronal and mixed neuronal-glial tumours, tumours of the pineal region, embryonal tumours, tumours of cranial and paraspinal nerves, tumours of the meninges, tumours of the haematopoietic system, tumours of the sellar region, a glioma, an astrocytoma, a glioblastoma, a medulloblastoma, and a neuroblastoma.

6. The method according to claim 1, wherein the malignant neoplasm is selected from grade II glioma, grade III glioma or grade IV glioma.

7. The method according to claim 1, wherein the malignant neoplasm is an astrocytic tumour selected from astrocytoma grade III and astrocytoma grade IV.

8. The method according to claim 1, wherein the malignant neoplasm is a glioblastoma.

9. The method according to claim 1, wherein the malignant neoplasm is a primary or secondary glioblastoma.

10. The method according to claim 1, wherein said sample is a brain tissue, a spinal cord tissue sample, or a blood sample.

11. The method according to claim 1, wherein the detectable moiety is a fluorophore, an enzyme, a radioactive tracer or radioisotope.

12. The method according to claim 1, wherein said sample is a sample of cells obtained from tissue or blood from the mammal.

13. A method for detecting elevated integrin alpha 10 subunit expression in cells associated with the central nervous system, said method comprising (1) obtaining an isolated sample comprising cells from the central nervous system from the mammal; and (2) detecting in the isolated sample the presence of:

a) an antigen comprising an integrin alpha 10 subunit polypeptide; and/or b) a polynucleotide transcript which encodes an integrin alpha 10 subunit polypeptide or a fragment or variant thereof, by contacting the sample with a reagent comprising an antibody with specificity for integrin alpha 10 subunit, or an integrin alpha 10 subunit nucleic acid probe that binds to an integrin alpha 10 subunit mRNA or cDNA, and detecting binding between the antibody with specificity for integrin alpha 10 subunit and the antigen comprising an integrin alpha 10 subunit polypeptide, or between the integrin alpha 10 subunit nucleic acid probe and the polynucleotide transcript which encodes an integrin alpha 10 subunit polypeptide or a fragment or variant thereof.

* * * * *

SEQUENCE LISTING

```
<160> NUMBER OF SEQ ID NOS: 4

<210> SEQ ID NO 1
<211> LENGTH: 1167
<212> TYPE: PRT
<213> ORGANISM: Homo sapiens
<220> FEATURE:
<221> NAME/KEY: MISC_FEATURE
<222> LOCATION: (1)..(1167)
<223> OTHER INFORMATION: Human integrin alpha 10 full length polypeptide

<400> SEQUENCE: 1

Met Glu Leu Pro Phe Val Thr His Leu Phe Leu Pro Leu Val Phe Leu
1               5                   10                  15

Thr Gly Leu Cys Ser Pro Phe Asn Leu Asp Glu His His Pro Arg Leu
            20                  25                  30

Phe Pro Gly Pro Pro Glu Ala Glu Phe Gly Tyr Ser Val Leu Gln His
        35                  40                  45

Val Gly Gly Gly Gln Arg Trp Met Leu Val Gly Ala Pro Trp Asp Gly
    50                  55                  60

Pro Ser Gly Asp Arg Arg Gly Asp Val Tyr Arg Cys Pro Val Gly Gly
65                  70                  75                  80

Ala His Asn Ala Pro Cys Ala Lys Gly His Leu Gly Asp Tyr Gln Leu
                85                  90                  95

Gly Asn Ser Ser His Pro Ala Val Asn Met His Leu Gly Met Ser Leu
            100                 105                 110

Leu Glu Thr Asp Gly Asp Gly Gly Phe Met Ala Cys Ala Pro Leu Trp
        115                 120                 125

Ser Arg Ala Cys Gly Ser Ser Val Phe Ser Ser Gly Ile Cys Ala Arg
    130                 135                 140

Val Asp Ala Ser Phe Gln Pro Gln Gly Ser Leu Ala Pro Thr Ala Gln
145                 150                 155                 160

Arg Cys Pro Thr Tyr Met Asp Val Val Ile Val Leu Asp Gly Ser Asn
                165                 170                 175

Ser Ile Tyr Pro Trp Ser Glu Val Gln Thr Phe Leu Arg Arg Leu Val
```

```
            180                 185                 190

Gly Lys Leu Phe Ile Asp Pro Glu Gln Ile Gln Val Gly Leu Val Gln
        195                 200                 205

Tyr Gly Glu Ser Pro Val His Glu Trp Ser Leu Gly Asp Phe Arg Thr
    210                 215                 220

Lys Glu Glu Val Val Arg Ala Ala Lys Asn Leu Ser Arg Arg Glu Gly
225                 230                 235                 240

Arg Glu Thr Lys Thr Ala Gln Ala Ile Met Val Ala Cys Thr Glu Gly
                245                 250                 255

Phe Ser Gln Ser His Gly Gly Arg Pro Glu Ala Ala Arg Leu Leu Val
            260                 265                 270

Val Val Thr Asp Gly Glu Ser His Asp Gly Glu Glu Leu Pro Ala Ala
        275                 280                 285

Leu Lys Ala Cys Glu Ala Gly Arg Val Thr Arg Tyr Gly Ile Ala Val
    290                 295                 300

Leu Gly His Tyr Leu Arg Arg Gln Arg Asp Pro Ser Ser Phe Leu Arg
305                 310                 315                 320

Glu Ile Arg Thr Ile Ala Ser Asp Pro Asp Glu Arg Phe Phe Phe Asn
                325                 330                 335

Val Thr Asp Glu Ala Ala Leu Thr Asp Ile Val Asp Ala Leu Gly Asp
            340                 345                 350

Arg Ile Phe Gly Leu Glu Gly Ser His Ala Glu Asn Glu Ser Ser Phe
        355                 360                 365

Gly Leu Glu Met Ser Gln Ile Gly Phe Ser Thr His Arg Leu Lys Asp
    370                 375                 380

Gly Ile Leu Phe Gly Met Val Gly Ala Tyr Asp Trp Gly Gly Ser Val
385                 390                 395                 400

Leu Trp Leu Glu Gly Gly His Arg Leu Phe Pro Pro Arg Met Ala Leu
                405                 410                 415

Glu Asp Glu Phe Pro Pro Ala Leu Gln Asn His Ala Ala Tyr Leu Gly
            420                 425                 430

Tyr Ser Val Ser Ser Met Leu Leu Arg Gly Gly Arg Arg Leu Phe Leu
        435                 440                 445

Ser Gly Ala Pro Arg Phe Arg His Arg Gly Lys Val Ile Ala Phe Gln
    450                 455                 460

Leu Lys Lys Asp Gly Ala Val Arg Val Ala Gln Ser Leu Gln Gly Glu
465                 470                 475                 480

Gln Ile Gly Ser Tyr Phe Gly Ser Glu Leu Cys Pro Leu Asp Thr Asp
                485                 490                 495

Arg Asp Gly Thr Thr Asp Val Leu Leu Val Ala Ala Pro Met Phe Leu
            500                 505                 510

Gly Pro Gln Asn Lys Glu Thr Gly Arg Val Tyr Val Tyr Leu Val Gly
        515                 520                 525

Gln Gln Ser Leu Leu Thr Leu Gln Gly Thr Leu Gln Pro Glu Pro Pro
    530                 535                 540

Gln Asp Ala Arg Phe Gly Phe Ala Met Gly Ala Leu Pro Asp Leu Asn
545                 550                 555                 560

Gln Asp Gly Phe Ala Asp Val Ala Val Gly Ala Pro Leu Glu Asp Gly
                565                 570                 575

His Gln Gly Ala Leu Tyr Leu Tyr His Gly Thr Gln Ser Gly Val Arg
            580                 585                 590

Pro His Pro Ala Gln Arg Ile Ala Ala Ala Ser Met Pro His Ala Leu
        595                 600                 605
```

```
Ser Tyr Phe Gly Arg Ser Val Asp Gly Arg Leu Asp Leu Asp Gly Asp
    610                 615                 620

Asp Leu Val Asp Val Ala Val Gly Ala Gln Gly Ala Ala Ile Leu Leu
625                 630                 635                 640

Ser Ser Arg Pro Ile Val His Leu Thr Pro Ser Leu Glu Val Thr Pro
                645                 650                 655

Gln Ala Ile Ser Val Val Gln Arg Asp Cys Arg Arg Arg Gly Gln Glu
            660                 665                 670

Ala Val Cys Leu Thr Ala Ala Leu Cys Phe Gln Val Thr Ser Arg Thr
        675                 680                 685

Pro Gly Arg Trp Asp His Gln Phe Tyr Met Arg Phe Thr Ala Ser Leu
    690                 695                 700

Asp Glu Trp Thr Ala Gly Ala Arg Ala Ala Phe Asp Gly Ser Gly Gln
705                 710                 715                 720

Arg Leu Ser Pro Arg Arg Leu Arg Leu Ser Val Gly Asn Val Thr Cys
                725                 730                 735

Glu Gln Leu His Phe His Val Leu Asp Thr Ser Asp Tyr Leu Arg Pro
            740                 745                 750

Val Ala Leu Thr Val Thr Phe Ala Leu Asp Asn Thr Thr Lys Pro Gly
        755                 760                 765

Pro Val Leu Asn Glu Gly Ser Pro Thr Ser Ile Gln Lys Leu Val Pro
    770                 775                 780

Phe Ser Lys Asp Cys Gly Pro Asp Asn Glu Cys Val Thr Asp Leu Val
785                 790                 795                 800

Leu Gln Val Asn Met Asp Ile Arg Gly Ser Arg Lys Ala Pro Phe Val
                805                 810                 815

Val Arg Gly Gly Arg Arg Lys Val Leu Val Ser Thr Thr Leu Glu Asn
            820                 825                 830

Arg Lys Glu Asn Ala Tyr Asn Thr Ser Leu Ser Ile Ile Phe Ser Arg
        835                 840                 845

Asn Leu His Leu Ala Ser Leu Thr Pro Gln Arg Glu Ser Pro Ile Lys
    850                 855                 860

Val Glu Cys Ala Ala Pro Ser Ala His Ala Arg Leu Cys Ser Val Gly
865                 870                 875                 880

His Pro Val Phe Gln Thr Gly Ala Lys Val Thr Phe Leu Leu Glu Phe
                885                 890                 895

Glu Phe Ser Cys Ser Ser Leu Leu Ser Gln Val Phe Gly Lys Leu Thr
            900                 905                 910

Ala Ser Ser Asp Ser Leu Glu Arg Asn Gly Thr Leu Gln Glu Asn Thr
        915                 920                 925

Ala Gln Thr Ser Ala Tyr Ile Gln Tyr Glu Pro His Leu Leu Phe Ser
    930                 935                 940

Ser Glu Ser Thr Leu His Arg Tyr Glu Val His Pro Tyr Gly Thr Leu
945                 950                 955                 960

Pro Val Gly Pro Gly Pro Glu Phe Lys Thr Thr Leu Arg Val Gln Asn
                965                 970                 975

Leu Gly Cys Tyr Val Val Ser Gly Leu Ile Ile Ser Ala Leu Leu Pro
            980                 985                 990

Ala Val Ala His Gly Gly Asn Tyr  Phe Leu Ser Leu Ser  Gln Val Ile
        995                 1000                 1005

Thr Asn  Asn Ala Ser Cys Ile  Val Gln Asn Leu Thr  Glu Pro Pro
    1010                 1015                 1020
```

```
Gly Pro  Pro Val His Pro Glu  Glu Leu Gln His Thr  Asn Arg Leu
    1025                 1030                 1035

Asn Gly  Ser Asn Thr Gln Cys  Gln Val Val Arg Cys  His Leu Gly
    1040                 1045                 1050

Gln Leu  Ala Lys Gly Thr Glu  Val Ser Val Gly Leu  Leu Arg Leu
    1055                 1060                 1065

Val His  Asn Glu Phe Phe Arg  Arg Ala Lys Phe Lys  Ser Leu Thr
    1070                 1075                 1080

Val Val  Ser Thr Phe Glu Leu  Gly Thr Glu Glu Gly  Ser Val Leu
    1085                 1090                 1095

Gln Leu  Thr Glu Ala Ser Arg  Trp Ser Glu Ser Leu  Leu Glu Val
    1100                 1105                 1110

Val Gln  Thr Arg Pro Ile Leu  Ile Ser Leu Trp Ile  Leu Ile Gly
    1115                 1120                 1125

Ser Val  Leu Gly Gly Leu Leu  Leu Leu Ala Leu Leu  Val Phe Cys
    1130                 1135                 1140

Leu Trp  Lys Leu Gly Phe Phe  Ala His Lys Lys Ile  Pro Glu Glu
    1145                 1150                 1155

Glu Lys  Arg Glu Glu Lys Leu  Glu Gln
    1160                 1165


<210> SEQ ID NO 2
<211> LENGTH: 1100
<212> TYPE: PRT
<213> ORGANISM: Homo sapiens
<220> FEATURE:
<221> NAME/KEY: MISC_FEATURE
<222> LOCATION: (1)..(1100)
<223> OTHER INFORMATION: Extracellular domain of human integrin alpha 10

<400> SEQUENCE: 2

Phe Asn Leu Asp Glu His His Pro Arg Leu Phe Pro Gly Pro Pro Glu
1               5                   10                  15

Ala Glu Phe Gly Tyr Ser Val Leu Gln His Val Gly Gly Gly Gln Arg
            20                  25                  30

Trp Met Leu Val Gly Ala Pro Trp Asp Gly Pro Ser Gly Asp Arg Arg
        35                  40                  45

Gly Asp Val Tyr Arg Cys Pro Val Gly Gly Ala His Asn Ala Pro Cys
    50                  55                  60

Ala Lys Gly His Leu Gly Asp Tyr Gln Leu Gly Asn Ser Ser His Pro
65                  70                  75                  80

Ala Val Asn Met His Leu Gly Met Ser Leu Leu Glu Thr Asp Gly Asp
                85                  90                  95

Gly Gly Phe Met Ala Cys Ala Pro Leu Trp Ser Arg Ala Cys Gly Ser
            100                 105                 110

Ser Val Phe Ser Ser Gly Ile Cys Ala Arg Val Asp Ala Ser Phe Gln
        115                 120                 125

Pro Gln Gly Ser Leu Ala Pro Thr Ala Gln Arg Cys Pro Thr Tyr Met
    130                 135                 140

Asp Val Val Ile Val Leu Asp Gly Ser Asn Ser Ile Tyr Pro Trp Ser
145                 150                 155                 160

Glu Val Gln Thr Phe Leu Arg Arg Leu Val Gly Lys Leu Phe Ile Asp
                165                 170                 175

Pro Glu Gln Ile Gln Val Gly Leu Val Gln Tyr Gly Glu Ser Pro Val
            180                 185                 190

His Glu Trp Ser Leu Gly Asp Phe Arg Thr Lys Glu Glu Val Val Arg
```

-continued

```
        195                 200                 205

Ala Ala Lys Asn Leu Ser Arg Arg Glu Gly Arg Glu Thr Lys Thr Ala
    210                 215                 220

Gln Ala Ile Met Val Ala Cys Thr Glu Gly Phe Ser Gln Ser His Gly
225                 230                 235                 240

Gly Arg Pro Glu Ala Ala Arg Leu Leu Val Val Val Thr Asp Gly Glu
                245                 250                 255

Ser His Asp Gly Glu Glu Leu Pro Ala Ala Leu Lys Ala Cys Glu Ala
            260                 265                 270

Gly Arg Val Thr Arg Tyr Gly Ile Ala Val Leu Gly His Tyr Leu Arg
        275                 280                 285

Arg Gln Arg Asp Pro Ser Ser Phe Leu Arg Glu Ile Arg Thr Ile Ala
    290                 295                 300

Ser Asp Pro Asp Glu Arg Phe Phe Phe Asn Val Thr Asp Glu Ala Ala
305                 310                 315                 320

Leu Thr Asp Ile Val Asp Ala Leu Gly Asp Arg Ile Phe Gly Leu Glu
                325                 330                 335

Gly Ser His Ala Glu Asn Glu Ser Ser Phe Gly Leu Glu Met Ser Gln
            340                 345                 350

Ile Gly Phe Ser Thr His Arg Leu Lys Asp Gly Ile Leu Phe Gly Met
        355                 360                 365

Val Gly Ala Tyr Asp Trp Gly Gly Ser Val Leu Trp Leu Glu Gly Gly
    370                 375                 380

His Arg Leu Phe Pro Pro Arg Met Ala Leu Glu Asp Glu Phe Pro Pro
385                 390                 395                 400

Ala Leu Gln Asn His Ala Ala Tyr Leu Gly Tyr Ser Val Ser Ser Met
                405                 410                 415

Leu Leu Arg Gly Gly Arg Arg Leu Phe Leu Ser Gly Ala Pro Arg Phe
            420                 425                 430

Arg His Arg Gly Lys Val Ile Ala Phe Gln Leu Lys Lys Asp Gly Ala
        435                 440                 445

Val Arg Val Ala Gln Ser Leu Gln Gly Glu Gln Ile Gly Ser Tyr Phe
    450                 455                 460

Gly Ser Glu Leu Cys Pro Leu Asp Thr Asp Arg Asp Gly Thr Thr Asp
465                 470                 475                 480

Val Leu Leu Val Ala Ala Pro Met Phe Leu Gly Pro Gln Asn Lys Glu
                485                 490                 495

Thr Gly Arg Val Tyr Val Tyr Leu Val Gly Gln Gln Ser Leu Leu Thr
            500                 505                 510

Leu Gln Gly Thr Leu Gln Pro Glu Pro Pro Gln Asp Ala Arg Phe Gly
        515                 520                 525

Phe Ala Met Gly Ala Leu Pro Asp Leu Asn Gln Asp Gly Phe Ala Asp
    530                 535                 540

Val Ala Val Gly Ala Pro Leu Glu Asp Gly His Gln Gly Ala Leu Tyr
545                 550                 555                 560

Leu Tyr His Gly Thr Gln Ser Gly Val Arg Pro His Pro Ala Gln Arg
                565                 570                 575

Ile Ala Ala Ala Ser Met Pro His Ala Leu Ser Tyr Phe Gly Arg Ser
            580                 585                 590

Val Asp Gly Arg Leu Asp Leu Asp Gly Asp Asp Leu Val Asp Val Ala
        595                 600                 605

Val Gly Ala Gln Gly Ala Ala Ile Leu Leu Ser Ser Arg Pro Ile Val
    610                 615                 620
```

-continued

His Leu Thr Pro Ser Leu Glu Val Thr Pro Gln Ala Ile Ser Val Val
625 630 635 640

Gln Arg Asp Cys Arg Arg Arg Gly Gln Glu Ala Val Cys Leu Thr Ala
645 650 655

Ala Leu Cys Phe Gln Val Thr Ser Arg Thr Pro Gly Arg Trp Asp His
660 665 670

Gln Phe Tyr Met Arg Phe Thr Ala Ser Leu Asp Glu Trp Thr Ala Gly
675 680 685

Ala Arg Ala Ala Phe Asp Gly Ser Gly Gln Arg Leu Ser Pro Arg Arg
690 695 700

Leu Arg Leu Ser Val Gly Asn Val Thr Cys Glu Gln Leu His Phe His
705 710 715 720

Val Leu Asp Thr Ser Asp Tyr Leu Arg Pro Val Ala Leu Thr Val Thr
725 730 735

Phe Ala Leu Asp Asn Thr Thr Lys Pro Gly Pro Val Leu Asn Glu Gly
740 745 750

Ser Pro Thr Ser Ile Gln Lys Leu Val Pro Phe Ser Lys Asp Cys Gly
755 760 765

Pro Asp Asn Glu Cys Val Thr Asp Leu Val Leu Gln Val Asn Met Asp
770 775 780

Ile Arg Gly Ser Arg Lys Ala Pro Phe Val Val Arg Gly Gly Arg Arg
785 790 795 800

Lys Val Leu Val Ser Thr Thr Leu Glu Asn Arg Lys Glu Asn Ala Tyr
805 810 815

Asn Thr Ser Leu Ser Leu Ile Phe Ser Arg Asn Leu His Leu Ala Ser
820 825 830

Leu Thr Pro Gln Arg Glu Ser Pro Ile Lys Val Glu Cys Ala Ala Pro
835 840 845

Ser Ala His Ala Arg Leu Cys Ser Val Gly His Pro Val Phe Gln Thr
850 855 860

Gly Ala Lys Val Thr Phe Leu Leu Glu Phe Glu Phe Ser Cys Ser Ser
865 870 875 880

Leu Leu Ser Gln Val Phe Val Lys Leu Thr Ala Ser Ser Asp Ser Leu
885 890 895

Glu Arg Asn Gly Thr Leu Gln Asp Asn Thr Ala Gln Thr Ser Ala Tyr
900 905 910

Ile Gln Tyr Glu Pro His Leu Leu Phe Ser Ser Glu Ser Thr Leu His
915 920 925

Arg Tyr Glu Val His Pro Tyr Gly Thr Leu Pro Val Gly Pro Gly Pro
930 935 940

Glu Phe Lys Thr Thr Leu Arg Val Gln Asn Leu Gly Cys Tyr Val Val
945 950 955 960

Ser Gly Leu Ile Ile Ser Ala Leu Leu Pro Ala Val Ala His Gly Gly
965 970 975

Asn Tyr Phe Leu Ser Leu Ser Gln Val Ile Thr Asn Asn Ala Ser Cys
980 985 990

Ile Val Gln Asn Leu Thr Glu Pro Pro Gly Pro Pro Val His Pro Glu
995 1000 1005

Glu Leu Gln His Thr Asn Arg Leu Asn Gly Ser Asn Thr Gln Cys
1010 1015 1020

Gln Val Val Arg Cys His Leu Gly Gln Leu Ala Lys Gly Thr Glu
1025 1030 1035

Val Ser Val Gly Leu Leu Arg Leu Val His Asn Glu Phe Phe Arg
    1040                1045                1050

Arg Ala Lys Phe Lys Ser Leu Thr Val Val Ser Thr Phe Glu Leu
    1055                1060                1065

Gly Thr Glu Glu Gly Ser Val Leu Gln Leu Thr Glu Ala Ser Arg
    1070                1075                1080

Trp Ser Glu Ser Leu Leu Glu Val Val Gln Thr Arg Pro Ile Leu
    1085                1090                1095

Ile Ser
    1100

<210> SEQ ID NO 3
<211> LENGTH: 198
<212> TYPE: PRT
<213> ORGANISM: Homo sapiens
<220> FEATURE:
<221> NAME/KEY: MISC_FEATURE
<222> LOCATION: (1)..(198)
<223> OTHER INFORMATION: I-domain of human integrin alpha 10

<400> SEQUENCE: 3

Cys Pro Thr Tyr Met Asp Val Val Ile Val Leu Asp Gly Ser Asn Ser
1               5                   10                  15

Ile Tyr Pro Trp Ser Glu Val Gln Thr Phe Leu Arg Arg Leu Val Gly
            20                  25                  30

Lys Leu Phe Ile Asp Pro Glu Gln Ile Gln Val Gly Leu Val Gln Tyr
        35                  40                  45

Gly Glu Ser Pro Val His Glu Trp Ser Leu Gly Asp Phe Arg Thr Lys
    50                  55                  60

Glu Glu Val Val Arg Ala Ala Lys Asn Leu Ser Arg Arg Glu Gly Arg
65                  70                  75                  80

Glu Thr Lys Thr Ala Gln Ala Ile Met Val Ala Cys Thr Glu Gly Phe
                85                  90                  95

Ser Gln Ser His Gly Gly Arg Pro Glu Ala Ala Arg Leu Leu Val Val
            100                 105                 110

Val Thr Asp Gly Glu Ser His Asp Gly Glu Glu Leu Pro Ala Ala Leu
        115                 120                 125

Lys Ala Cys Glu Ala Gly Arg Val Thr Arg Tyr Gly Ile Ala Val Leu
    130                 135                 140

Gly His Tyr Leu Arg Arg Gln Arg Asp Pro Ser Ser Phe Leu Arg Glu
145                 150                 155                 160

Ile Arg Thr Ile Ala Ser Asp Pro Asp Glu Arg Phe Phe Phe Asn Val
                165                 170                 175

Thr Asp Glu Ala Ala Leu Thr Asp Ile Val Asp Ala Leu Gly Asp Arg
            180                 185                 190

Ile Phe Gly Leu Glu Gly
        195

<210> SEQ ID NO 4
<211> LENGTH: 4644
<212> TYPE: DNA
<213> ORGANISM: Homo sapiens
<220> FEATURE:
<221> NAME/KEY: misc_feature
<222> LOCATION: (1)..(4644)
<223> OTHER INFORMATION: Homo sapiens integrin subunit alpha 10
      precursor, mRNA, complete cds

<400> SEQUENCE: 4

```
atggaactcc ccttcgtcac tcacctgttc ttgcccctgg tgttcctgac aggtctctgc     60
tccccccttta acctggatga acatcaccca cgcctattcc cagggccacc agaagctgaa   120
tttggataca gtgtcttaca acatgttggg ggtggacagc gatggatgct ggtgggcgcc   180
ccctgggatg ggccttcagg cgaccggagg ggggacgttt atcgctgccc tgtagggggg   240
gcccacaatg ccccatgtgc caagggccac ttaggtgact accaactggg aaattcatct   300
catcctgctg tgaatatgca cctggggatg tctctgttag agacagatgg tgatgggggga   360
ttcatggcct gtgcccctct ctggtctcgt gcttgtggca gctctgtctt cagttctggg   420
atatgtgccc gtgtggatgc ttcattccag cctcagggaa gcctggcacc cactgcccaa   480
cgctgcccaa catacatgga tgttgtcatt gtcttggatg gctccaacag catctacccc   540
tggtctgaag ttcagacctt cctacgaaga ctggtaggga aactgtttat tgacccagaa   600
cagatacagg tgggactggt acagtatggg gagagccctg tacatgagtg gtccctggga   660
gatttccgaa cgaaggaaga agtggtgaga gcagcaaaga acctcagtcg gcgggaggga   720
cgagaaacaa agactgccca agcaataatg gtggcctgca cagaagggtt cagtcagtcc   780
catgggggcc gacccgaggc tgccaggcta ctggtggttg tcactgatgg agagtcccat   840
gatggagagg agcttcctgc agcactaaag gcctgtgagg ctggaagagt gacacgctat   900
gggattgcag tccttggtca ctacctccgg cggcagcgag atcccagctc tttcctgaga   960
gaaattagaa ctattgccag tgatccagat gagcgattct tcttcaatgt cacagatgag  1020
gctgctctga ctgacattgt ggatgcacta ggagatcgga tttttggcct tgaagggtcc  1080
catgcagaaa acgaaagctc ctttgggctg gaaatgtctc agattggttt ctccactcat  1140
cggctaaagg atgggattct ttttgggatg gtgggggcct atgactgggg aggctctgtg  1200
ctatggcttg aaggaggcca ccgccttttc cccccacgaa tggcactgga agacgagttc  1260
ccccctgcac tgcagaacca tgcagcctac ctgggttact ctgtttcttc catgcttttg  1320
cggggtggac gccgcctgtt tctctctggg gctcctcgat ttagacatcg aggaaaagtc  1380
atcgccttcc agcttaagaa agatggggct gtgagggttg cccagagcct ccagggggag  1440
cagattggtt catactttgg cagtgagctc tgcccattgg atacagatag ggatggaaca  1500
actgatgtct tacttgtggc tgccccccatg ttcctgggac cccagaacaa ggaaacagga  1560
cgtgtttatg tgtatctggt aggccagcag tccttgctga ccctccaagg aacacttcag  1620
ccagaacccc cccaggatgc tcggtttggc tttgccatgg gagctcttcc tgatctgaac  1680
caagatggtt ttgctgatgt ggctgtgggg gcgcctctgg aagatgggca ccagggagca  1740
ctgtacctgt accatggaac ccagagtgga gtcaggcccc atcctgccca gaggattgct  1800
gctgcctcca tgccacatgc cctcagctac tttggccgaa gtgtggatgg tcggctagat  1860
ctggatggag atgatctggt cgatgtggct gtgggtgccc agggggcagc catcctgctc  1920
agctcccggc ccattgtcca tctgacccca tcactggagg tgaccccaca ggccatcagt  1980
gtggttcaga gggactgtag gcggcgaggc caagaagcag tctgtctgac tgcagccctt  2040
tgcttccaag tgacctcccg tactcctggt cgctgggatc accaattcta catgaggttc  2100
accgcatcac tggatgaatg gactgctggg gcacgtgcag catttgatgg ctctggccag  2160
aggttgtccc ctcggaggct ccggctcagt gtggggaatg tcacttgtga gcagctacac  2220
ttccatgtgc tggatacatc agattacctc cggccagtgg ccttgactgt gacctttgcc  2280
ttggacaata ctacaaagcc agggcctgtg ctgaatgagg gctcacccac ctctatacaa  2340
aagctggtcc ccttctcaaa ggattgtggc cctgacaatg aatgtgtcac agacctggtg  2400
```

-continued

```
cttcaagtga atatggacat cagaggctcc aggaaggccc catttgtggt tcgaggtggc   2460
cggcggaaag tgctggtatc tacaactctg gagaacagaa aggaaaatgc ttacaatacg   2520
agcctgagta tcatcttctc tagaaacctc cacctggcca gtctcactcc tcagagagag   2580
agcccaataa aggtggaatg tgccgcccct tctgctcatg cccggctctg cagtgtgggg   2640
catcctgtct tccagactgg agccaaggtg acctttctgc tagagtttga gtttagctgc   2700
tcctctctcc tgagccaggt ctttgggaag ctgactgcca gcagtgacag cctggagaga   2760
aatggcaccc ttcaagaaaa cacagcccag acctcagcct acatccaata tgagccccac   2820
ctcctgttct ctagtgagtc taccctgcac cgctatgagg ttcacccata tgggaccctc   2880
ccagtgggtc ctggcccaga attcaaaacc actctcaggg ttcagaacct aggctgctat   2940
gtggtcagtg gcctcatcat ctcagccctc cttccagctg tggcccatgg gggcaattac   3000
ttcctatcac tgtctcaagt catcactaac aatgcaagct gcatagtgca gaacctgact   3060
gaacccccag gcccacctgt gcatccagag gagcttcaac acacaaacag actgaatggg   3120
agcaatactc agtgtcaggt ggtgaggtgc caccttgggc agctggcaaa ggggactgag   3180
gtctctgttg gactattgag gctggttcac aatgaatttt tccgaagagc caagttcaag   3240
tccctgacgg tggtcagcac ctttgagctg ggaaccgaag agggcagtgt cctacagctg   3300
actgaagcct cccgttggag tgagagcctc ttggaggtgg ttcagacccg gcctatcctc   3360
atctccctgt ggatcctcat aggcagtgtc ctgggagggt tgctcctgct tgctctcctt   3420
gtcttctgcc tgtggaagct tggcttcttt gcccataaga aaatccctga ggaagaaaaa   3480
agagaagaga agttggagca atgatgtggc cctgacaatg aatgtgtcac agacctggtg   3540
cttcaagtga atatggacat cagaggctcc aggaaggccc catttgtggt tcgaggtggc   3600
cggcggaaag tgctggtatc tacaactctg gagaacagaa aggaaaatgc ttacaatacg   3660
agcctgagta tcatcttctc tagaaacctc cacctggcca gtctcactcc tcagagagag   3720
agcccaataa aggtggaatg tgccgcccct tctgctcatg cccggctctg cagtgtgggg   3780
catcctgtct tccagactgg agccaaggtg acctttctgc tagagtttga gtttagctgc   3840
tcctctctcc tgagccaggt ctttgggaag ctgactgcca gcagtgacag cctggagaga   3900
aatggcaccc ttcaagaaaa cacagcccag acctcagcct acatccaata tgagccccac   3960
ctcctgttct ctagtgagtc taccctgcac cgctatgagg ttcacccata tgggaccctc   4020
ccagtgggtc ctggcccaga attcaaaacc actctcaggg ttcagaacct aggctgctat   4080
gtggtcagtg gcctcatcat ctcagccctc cttccagctg tggcccatgg gggcaattac   4140
ttcctatcac tgtctcaagt catcactaac aatgcaagct gcatagtgca gaacctgact   4200
gaacccccag gcccacctgt gcatccagag gagcttcaac acacaaacag actgaatggg   4260
agcaatactc agtgtcaggt ggtgaggtgc caccttgggc agctggcaaa ggggactgag   4320
gtctctgttg gactattgag gctggttcac aatgaatttt tccgaagagc caagttcaag   4380
tccctgacgg tggtcagcac ctttgagctg ggaaccgaag agggcagtgt cctacagctg   4440
actgaagcct cccgttggag tgagagcctc ttggaggtgg ttcagacccg gcctatcctc   4500
atctccctgt ggatcctcat aggcagtgtc ctgggagggt tgctcctgct tgctctcctt   4560
gtcttctgcc tgtggaagct tggcttcttt gcccataaga aaatccctga ggaagaaaaa   4620
agagaagaga agttggagca atga                                          4644
```